US010677785B2

(12) United States Patent
Armstrong et al.

(10) Patent No.: US 10,677,785 B2
(45) Date of Patent: *Jun. 9, 2020

(54) REPORTER CONSTRUCTS FOR COMPOUND SCREENING

(71) Applicant: Koch Biological Solutions LLC, Hayward, CA (US)

(72) Inventors: Joshua I. Armstrong, San Mateo, CA (US); Hans E. Holtan, Emeryville, GA (US); Masa-aki Ohto, Davis, CA (US); Adina M. Bailey, Oakland, CA (US); Robert A. Creelman, Castro Valley, CA (US)

(73) Assignee: Plant Response, Inc., Durham, NC (US)

( * ) Notice: Subject to any disclaimer, the term of this patent is extended or adjusted under 35 U.S.C. 154(b) by 80 days.

This patent is subject to a terminal disclaimer.

(21) Appl. No.: 15/097,339

(22) Filed: Apr. 13, 2016

(65) Prior Publication Data

US 2016/0349243 A1 Dec. 1, 2016

Related U.S. Application Data

(60) Continuation-in-part of application No. 15/084,800, filed on Mar. 30, 2016, now abandoned, which is a division of application No. 13/699,527, filed as application No. PCT/US2011/037573 on May 23, 2011, now Pat. No. 9,322,070, which is a continuation of application No. PCT/US2010/045941, filed on Aug. 18, 2010.

(60) Provisional application No. 61/347,516, filed on May 24, 2010.

(51) Int. Cl.
C12Q 1/68 (2018.01)
C12N 15/82 (2006.01)
G01N 33/50 (2006.01)
C12Q 1/6897 (2018.01)
C12Q 1/6876 (2018.01)

(52) U.S. Cl.
CPC ..... G01N 33/5097 (2013.01); C12N 15/8237 (2013.01); C12N 15/8261 (2013.01); C12N 15/8273 (2013.01); C12Q 1/6876 (2013.01); C12Q 1/6897 (2013.01); Y02A 40/146 (2018.01)

(58) Field of Classification Search
None
See application file for complete search history.

(56) References Cited

U.S. PATENT DOCUMENTS 4,833,080 A 5/1989 Brent
6,784,340 B1* 8/2004 Aoyama ............ C12N 15/8209 435/320.1
6,946,586 B1 9/2005 Fromm
2007/0031390 A1 2/2007 Weeks
2008/0301836 A1* 12/2008 Century ............... C07K 14/415 800/279
2010/0071086 A1 3/2010 Repetti et al.

FOREIGN PATENT DOCUMENTS

| EP | 11787193.9 A1 | 10/2013 |
| EP | 11787193.9 A1 | 4/2015 |
| WO | WO9730164 A1 | 8/1997 |
| WO | WO0134820 A2 | 5/2001 |
| WO | WO02074917 A2 | 9/2002 |
| WO | WO02079500 A1 | 10/2002 |
| WO | WO2009158591 A1 | 12/2009 |
| WO | WO2011149843 A1 | 12/2011 |
| WO | PCT/US2011/037573 A1 | 11/2012 |

OTHER PUBLICATIONS

Tester and Bacic, 2005, Plant Physiology 137: 791-793.*
Golemis and Brent, 1992, Molecular and Cellular Biology 12: 3006-3014.*
Karimi et al., 2009, European Journal of Human Genetics 17: 1454-1462.*
Porto et al., 2014, Mol. Biotechnol. 56: 38-49.*
Zuo et al., 2000, The Plant Journal 24: 265-273.*
Ichikawa et al., 2006, J. Biochem. 139: 105-112.*
Mignone et al., 2011, In: eLS, John Wiley & Sons, Ltd: Chichester, pp. 1-5.*
Hicks and Raikhel, 2009, Nature Chemical Biology 5: 268-272.*
Moore, I. et al. 1998, "A Transcription Activation System for Regulated Gene Expression in Transgenic Plants"; Proc. Natl. Acad. Sci. USA 95: 376-381.
Aoyama, T. et al. 1995, "Ectopic Expression of the Arabidopsis Transcriptional Activator Athb-1 Alters Leaf Cell Fate in Tobacco"; The Plant Cell, 7: 1773-1785.
Ichikawa, K., and Eki, T. 2006, "A Novel Yeast-Based Reporter Assay System for the Sensitive Detection of Genotoxic Agents Mediated by a DNA Damage- . . . " J. Biochem.139:105-112.
Keeley, M. B., et al., 2005, "TetR hybrid transcription factors report cell signaling and are inhibited by doxycycline", Biotechniques: 39:529-536.
Levinson, N. et al. 2006, "Use of transcriptional synergy to augment sensitivity of a splicing reporter assay", RNA 12:925-930.

(Continued)

Primary Examiner — Bratislav Stankovic
(74) Attorney, Agent, or Firm — Myers Bigel, P.A.

(57) ABSTRACT

The instant description provides reporter constructs, transgenic cells, and transgenic organisms and methods for identifying agents that can regulate gene expression and improve plant performance and yield. Compounds that increase plant performance or yield are identified by contacting a test compound with a plant cell that comprises a target promoter sequence operably linked to a polynucleotide sequence encoding a DNA sequence-specific transactivator, and a reporter polynucleotide that is operably linked to a promoter sequence that is recognized by the DNA sequence-specific transactivator. The target promoter sequence can be recognized by a transcriptional regulatory polypeptide capable of modulating specific signaling pathways that enhance plant performance or yield.

20 Claims, 16 Drawing Sheets

Figure 1:
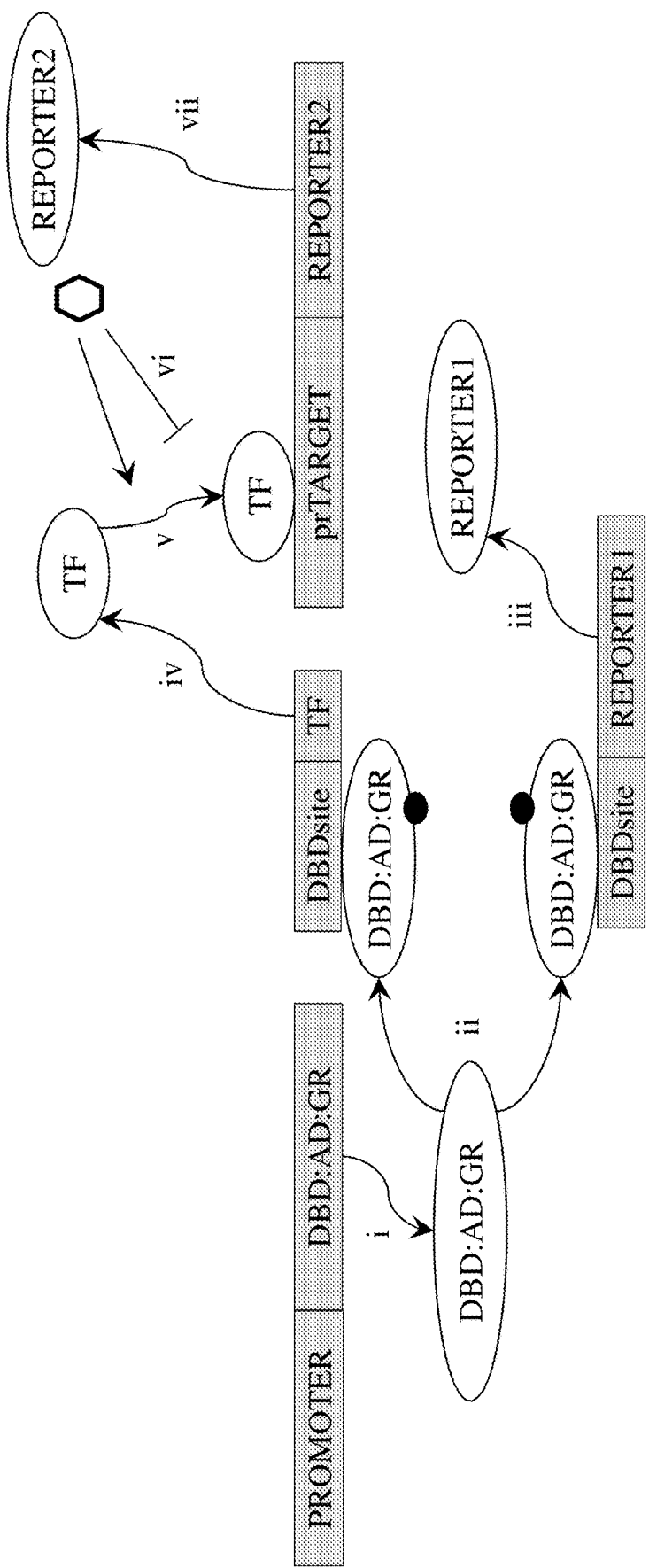

Specification includes a Sequence Listing.

(56) References Cited

OTHER PUBLICATIONS

Aoyama et al. 1997, "A glucocorticoid-mediated transcriptional induction system in transgenic plants", Plant J. 11(3):605-612.
Elliott, D. A., et al. 2008, "The GAL4 system—A versatile system for the expression of genes", Methods Malec. Biol. 420:79-95.
Hexdall, L. et al. 2001 "Product Application Focus, Stable Luciferase Reporter Cell Lines for Signal Transduction Pathway Readout Using GAL4 Fusion . . . " Biotechniq. 30:1134-1140.
Zhao, S-Q. 2004, "Expression of the Pathogenesis-related Gene Promoter-GUS Reporter Fusion in Arabidopsis" Acta Botanica Sinica 46:982-987.

* cited by examiner

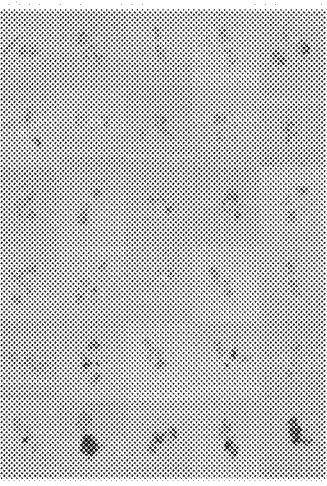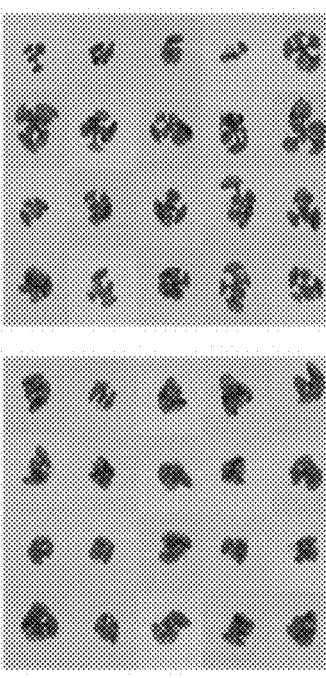
FIG. 8A  FIG. 8B  FIG. 8C  FIG. 8D  FIG. 8E

SEQUENCE LISTING

```
<160> NUMBER OF SEQ ID NOS: 48

<210> SEQ ID NO 1
<211> LENGTH: 1839
<212> TYPE: DNA
<213> ORGANISM: artificial sequence
<220> FEATURE:
<223> OTHER INFORMATION: a DNA sequence encoding E. coli LexA DNA
      binding domain, Yeast GAL4 activation domain and the ligand
      binding domain of GR

<400> SEQUENCE: 1
atggaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcaa gaagaggaag aagggttgcc gctggtaggt     240
cgtgtggctg ccggtgaacc acttctggcg caacagcata ttgaaggtca ttatcaggtc     300
gatccttcct tattcaagcc gaatgctgat ttcctgctgc gcgtcagcgg gatgtcgatg     360
aaagatatcg gcattatgga tggtgacttg ctggcagtgc ataaaactca ggatgtacgt     420
aacggtcagg tcgttgtcgc acgtattgat gacgaggtta ccgttaagcg cctgaaaaaa     480
cagggcaata aagtcgaact gttgccagaa aatagcgagt ttaaaccaat tgtcgtagat     540
cttcgtcagc agagcttcac cattgaaggg ctggcggttg gggttattcg caacggcgac     600
tggctggaat tccccaattt taatcaaagt gggaatattg ctgatagcgc attgtccttc     660
actttcacta acagtagcaa cggtccgaac ctcataacaa ctcaaacaaa ttctcaagcg     720
ctttcacaac caattgcctc ctctaacgtt catgataact tcatgaataa tgaaatcacg     780
gctagtaaaa ttgatgatgg taataattca aaaccactgt cacctggttg gacggaccaa     840
actgcgtata acgcgtttgg aatcactaca gggatgttta ataccactac aatggatgat     900
gtatataact atctattcga tgatgaagat accccaccaa acccaaaaaa agctgctgct     960
gctgaggatc ctgaagctcg aaaaacaaag aaaaaaatca aagggattca gcaagccact    1020
gcaggagtct cacaagacac ttcggaaaat cctaacaaaa caatagttcc tgcagcatta    1080
ccacagctca cccctacctt ggtgtcactg ctggaggtga ttgaacccga ggtgttgtat    1140
gcaggatatg atagctctgt tccagattca gcatggagaa ttatgaccac actcaacatg    1200
ttaggtgggc gtcaagtgat tgcagcagtg aaatgggcaa aggcgatacc aggcttcaga    1260
aacttacacc tggatgacca aatgaccctg ctacagtact catggatgtt tctcatggca    1320
tttgccctgg gttggagatc atacagacaa tcaagtggaa acctgctctg ctttgctcct    1380
gatctgatta ttaatgagca gaagatgtct ctaccctgca tgtatgacca atgtaaacac    1440
atgctgtttt tctcctctga attacaaaga ttgcaggtat cctatgaaga gtatctctgt    1500
atgaaaacct tactgcttct ctcctcagtt cctaaggaag gtctgaagag ccaagagtta    1560
```

```
tttgatgaga ttcgaatgac ttatatcaaa gagctaggaa aagccatcgt caaaagggaa    1620
gggaactcca gtcagaactg gcaacggttt taccaactga caaagcttct ggactccatg    1680
catgaggtgg ttgagaatct ccttacctac tgcttccaga cattttttgga taagaccatg   1740 agtattgaat tcccagagat gttagctgaa atcatcacta atcagatacc aaaatattca    1800
aatggaaata ccaaaaagct tctgtttcat caaaaatga                           1839
```

<210> SEQ ID NO 2
<211> LENGTH: 612
<212> TYPE: PRT
<213> ORGANISM: artificial sequence
<220> FEATURE:
<223> OTHER INFORMATION: a translational fusion of the E. coli LexA DNA
      binding domain, Yeast GAL4 activation domain and the ligand
      binding domain of GR

<400> SEQUENCE: 2

```
Met Glu Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Asn Phe Asn
        195                 200                 205

Gln Ser Gly Asn Ile Ala Asp Ser Ala Leu Ser Phe Thr Phe Thr Asn
    210                 215                 220

Ser Ser Asn Gly Pro Asn Leu Ile Thr Thr Gln Thr Asn Ser Gln Ala
225                 230                 235                 240

Leu Ser Gln Pro Ile Ala Ser Ser Asn Val His Asp Asn Phe Met Asn
                245                 250                 255

Asn Glu Ile Thr Ala Ser Lys Ile Asp Asp Gly Asn Asn Ser Lys Pro
            260                 265                 270

Leu Ser Pro Gly Trp Thr Asp Gln Thr Ala Tyr Asn Ala Phe Gly Ile
        275                 280                 285

Thr Thr Gly Met Phe Asn Thr Thr Thr Met Asp Asp Val Tyr Asn Tyr
    290                 295                 300
```

Leu Phe Asp Asp Glu Asp Thr Pro Pro Asn Pro Lys Lys Ala Ala Ala
305                 310                 315                 320

Ala Glu Asp Pro Glu Ala Arg Lys Thr Lys Lys Ile Lys Gly Ile
            325                 330                 335

Gln Gln Ala Thr Ala Gly Val Ser Gln Asp Thr Ser Glu Asn Pro Asn
            340                 345                 350

Lys Thr Ile Val Pro Ala Ala Leu Pro Gln Leu Thr Pro Thr Leu Val
        355                 360                 365

Ser Leu Leu Glu Val Ile Glu Pro Glu Val Leu Tyr Ala Gly Tyr Asp
    370                 375                 380

Ser Ser Val Pro Asp Ser Ala Trp Arg Ile Met Thr Thr Leu Asn Met
385                 390                 395                 400

Leu Gly Gly Arg Gln Val Ile Ala Ala Val Lys Trp Ala Lys Ala Ile
            405                 410                 415

Pro Gly Phe Arg Asn Leu His Leu Asp Asp Gln Met Thr Leu Leu Gln
            420                 425                 430

Tyr Ser Trp Met Phe Leu Met Ala Phe Ala Leu Gly Trp Arg Ser Tyr
        435                 440                 445

Arg Gln Ser Ser Gly Asn Leu Leu Cys Phe Ala Pro Asp Leu Ile Ile
    450                 455                 460

Asn Glu Gln Arg Met Ser Leu Pro Cys Met Tyr Asp Gln Cys Lys His
465                 470                 475                 480

Met Leu Phe Val Ser Ser Glu Leu Gln Arg Leu Gln Val Ser Tyr Glu
            485                 490                 495

Glu Tyr Leu Cys Met Lys Thr Leu Leu Leu Ser Ser Val Pro Lys
        500                 505                 510

Glu Gly Leu Lys Ser Gln Glu Leu Phe Asp Glu Ile Arg Met Thr Tyr
        515                 520                 525

Ile Lys Glu Leu Gly Lys Ala Ile Val Lys Arg Glu Gly Asn Ser Ser
    530                 535                 540

Gln Asn Trp Gln Arg Phe Tyr Gln Leu Thr Lys Leu Leu Asp Ser Met
545                 550                 555                 560

His Glu Val Val Glu Asn Leu Leu Thr Tyr Cys Phe Gln Thr Phe Leu
            565                 570                 575

Asp Lys Thr Met Ser Ile Glu Phe Pro Glu Met Leu Ala Glu Ile Ile
        580                 585                 590

Thr Asn Gln Ile Pro Lys Tyr Ser Asn Gly Asn Thr Lys Lys Leu Leu
        595                 600                 605

Phe His Gln Lys
    610

<210> SEQ ID NO 3
<211> LENGTH: 954
<212> TYPE: DNA
<213> ORGANISM: artificial sequence
<220> FEATURE:
<223> OTHER INFORMATION: a DNA sequence encoding the E. coli LexA DNA
      binding domain and the yeast GAL4 activation domain

<400> SEQUENCE: 3
atggaagcgt taacggccag caacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg cacgcaaag gcgttattga aattgtttcc     180
ggcgcatcac gcgggattcg tctgttgcaa gaagaggaag aagggttgcc gctggtaggt     240

```
cgtgtggctg ccggtgaacc acttctggcg caacagcata ttgaaggtca ttatcaggtc      300
gatccttcct tattcaagcc gaatgctgat ttcctgctgc gcgtcagcgg gatgtcgatg      360
aaagatatcg gcattatgga tggtgacttg ctggcagtgc ataaaactca ggatgtacgt      420
aacggtcagg tcgttgtcgc acgtattgat gacgaggtta ccgttaagcg cctgaaaaaa      480
cagggcaata agtcgaact gttgccagaa aatagcgagt ttaaaccaat tgtcgtagat        540
cttcgtcagc agagcttcac cattgaaggg ctggcggttg ggttattcg caacggcgac        600 tggctggaat tccccaattt taatcaaagt gggaatattg ctgatagcgc attgtccttc      660
actttcacta acagtagcaa cggtccgaac ctcataacaa ctcaaacaaa ttctcaagcg      720
ctttcacaac caattgcctc ctctaacgtt catgataact tcatgaataa tgaaatcacg      780
gctagtaaaa ttgatgatgg taataattca aaaccactgt cacctggttg gacggaccaa      840
actgcgtata acgcgtttgg aatcactaca gggatgttta ataccactac aatggatgat      900
gtatataact atctattcga tgatgaagat accccaccaa acccaaaaaa atga              954
```

<210> SEQ ID NO 4
<211> LENGTH: 317
<212> TYPE: PRT
<213> ORGANISM: artificial sequence
<220> FEATURE:
<223> OTHER INFORMATION: a translational fusion of the E. coli LexA DNA binding domain and the yeast GAL4 activation domain

<400> SEQUENCE: 4

```
Met Glu Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Asn Phe Asn
        195                 200                 205

Gln Ser Gly Asn Ile Ala Asp Ser Ala Leu Ser Phe Thr Phe Thr Asn
    210                 215                 220

Ser Ser Asn Gly Pro Asn Leu Ile Thr Thr Gln Thr Asn Ser Gln Ala
```

```
                225                 230                 235                 240
Leu Ser Gln Pro Ile Ala Ser Ser Asn Val His Asp Asn Phe Met Asn
                    245                 250                 255
Asn Glu Ile Thr Ala Ser Lys Ile Asp Asp Gly Asn Asn Ser Lys Pro
                260                 265                 270
Leu Ser Pro Gly Trp Thr Asp Gln Thr Ala Tyr Asn Ala Phe Gly Ile
            275                 280                 285
Thr Thr Gly Met Phe Asn Thr Thr Thr Met Asp Asp Val Tyr Asn Tyr
        290                 295                 300
Leu Phe Asp Asp Glu Asp Thr Pro Pro Asn Pro Lys Lys
305                 310                 315

<210> SEQ ID NO 5
<211> LENGTH: 272
<212> TYPE: DNA
<213> ORGANISM: Escherichia coli

<400> SEQUENCE: 5
acatatccat atctaatctt acctcgactg ctgtatataa aaccagtggt tatatgtcca    60
gtactgctgt atataaaacc agtggttata tgtacagtac gtcgatcgat cgacgactgc   120
tgtatataaa accagtggtt atatgtacag tactgctgta tataaaacca gtggttatat   180
gtacagtacg tcgaggggat gatcaagacc cttcctctat ataaggaagt tcatttcatt   240
tggagaggac acgctgacaa gctgactcta gc                                272

<210> SEQ ID NO 6
<211> LENGTH: 1563
<212> TYPE: DNA
<213> ORGANISM: artificial sequence
<220> FEATURE:
<223> OTHER INFORMATION: a DNA sequence encoding the yeast GAL4 DNA
      binding domain and the herpes simplex virus VP16 protein and the
      ligand binding domain of GR

<400> SEQUENCE: 6
atggggctac tgtcttctat cgaacaagca tgcgatattt gccgacttaa aaagctcaag    60
tgctccaaag aaaaaccgaa gtgcgccaag tgtctgaaga caactgggga gtgtcgctac   120
tctcccaaaa ccaaaaggtc tccgctgact agggcacatc tgacagaagt ggaatcaagg   180
ctagaaagac tggaacagct atttctactg atttttcctc gagaagacct tgacatgatt   240
ttgaaaatgg attctttaca ggatataaaa gcattgttaa caggattatt tgtacaagat   300
aatgtgaata agatgccgt cacagataga ttggcttcag tggagactga tatgcctcta   360
acattgagac agcatagaat aagtgcgaca tcatcatcgg aagagagtag taacaaaggt   420
caaagacagt tgactgtatc gccggaattc ccggggatct gggccccccc gaccgatgtc   480
agcctggggg acgagctcca cttagacggc gaggacgtgg cgatggcgca tgccgacgcg   540
ctagacgatt tcgatctgga catgttgggg gacggggatt ccccgggtcc gggatttacc   600
ccccacgact ccgccccta cggcgctctg gatatggccg acttcgagtt tgagcagatg   660
tttaccgatg cccttggaat tgacgagtac ggtggggaag ctcgaaaaac aaagaaaaaa   720
atcaaaggga ttcagcaagc cactgcagga gtctcacaag acacttcgga aaatcctaac   780
aaaacaatag ttcctgcagc attaccacag ctcacccct ccttggtgtc actgctggag   840
gtgattgaac ccgaggtgtt gtatgcagga tatgatagct ctgttccaga ttcagcatgg   900
agaattatga ccacactcaa catgttaggt gggcgtcaag tgattgcagc agtgaaatgg   960
```

-continued

```
gcaaaggcga taccaggctt cagaaactta cacctggatg accaaatgac cctgctacag    1020
tactcatgga tgtttctcat ggcatttgcc ctgggttgga gatcatacag acaatcaagt    1080
ggaaacctgc tctgctttgc tcctgatctg attattaatg agcagagaat gtctctaccc    1140
tgcatgtatg accaatgtaa acacatgctg tttgtctcct ctgaattaca aagattgcag    1200
gtatcctatg aagagtatct ctgtatgaaa accttactgc ttctctcctc agttcctaag    1260
gaaggtctga agagccaaga gttatttgat gagattcgaa tgacttatat caaagagcta    1320
ggaaaagcca tcgtcaaaag ggaagggaac tccagtcaga actggcaacg gttttaccaa    1380
ctgacaaagc ttctggactc catgcatgag gtggttgaga atctccttac ctactgcttc    1440
cagacatttt tggataagac catgagtatt gaattcccag agatgttagc tgaaatcatc    1500
actaatcaga taccaaaata ttcaaatgga aataccaaaa agcttctgtt tcatcaaaaa    1560
tga                                                                  1563
```

<210> SEQ ID NO 7
<211> LENGTH: 520
<212> TYPE: PRT
<213> ORGANISM: artificial sequence
<220> FEATURE:
<223> OTHER INFORMATION: a translational fusion of the yeast GAL4 DNA
      binding domain and the herpes simplex virus VP16 protein and the
      ligand binding domain of GR

<400> SEQUENCE: 7

```
Met Gly Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Trp Ala Pro Pro Thr Asp Val
145                 150                 155                 160

Ser Leu Gly Asp Glu Leu His Leu Asp Gly Glu Asp Val Ala Met Ala
                165                 170                 175

His Ala Asp Ala Leu Asp Asp Phe Asp Leu Asp Met Leu Gly Asp Gly
            180                 185                 190

Asp Ser Pro Gly Pro Gly Phe Thr Pro His Asp Ser Ala Pro Tyr Gly
        195                 200                 205

Ala Leu Asp Met Ala Asp Phe Glu Phe Glu Gln Met Phe Thr Asp Ala
    210                 215                 220

Leu Gly Ile Asp Glu Tyr Gly Gly Glu Ala Arg Lys Thr Lys Lys Lys
225                 230                 235                 240
```

```
Ile Lys Gly Ile Gln Gln Ala Thr Ala Gly Val Ser Gln Asp Thr Ser
            245                 250                 255

Glu Asn Pro Asn Lys Thr Ile Val Pro Ala Ala Leu Pro Gln Leu Thr
        260                 265                 270

Pro Thr Leu Val Ser Leu Leu Glu Val Ile Glu Pro Glu Val Leu Tyr
    275                 280                 285

Ala Gly Tyr Asp Ser Ser Val Pro Asp Ser Ala Trp Arg Ile Met Thr
290                 295                 300

Thr Leu Asn Met Leu Gly Gly Arg Gln Val Ile Ala Ala Val Lys Trp
305                 310                 315                 320

Ala Lys Ala Ile Pro Gly Phe Arg Asn Leu His Leu Asp Asp Gln Met
                325                 330                 335

Thr Leu Leu Gln Tyr Ser Trp Met Phe Leu Met Ala Phe Ala Leu Gly
            340                 345                 350

Trp Arg Ser Tyr Arg Gln Ser Ser Gly Asn Leu Leu Cys Phe Ala Pro
        355                 360                 365

Asp Leu Ile Ile Asn Glu Gln Arg Met Ser Leu Pro Cys Met Tyr Asp
    370                 375                 380

Gln Cys Lys His Met Leu Phe Val Ser Ser Glu Leu Gln Arg Leu Gln
385                 390                 395                 400

Val Ser Tyr Glu Glu Tyr Leu Cys Met Lys Thr Leu Leu Leu Leu Ser
                405                 410                 415

Ser Val Pro Lys Glu Gly Leu Lys Ser Gln Glu Leu Phe Asp Glu Ile
            420                 425                 430

Arg Met Thr Tyr Ile Lys Glu Leu Gly Lys Ala Ile Val Lys Arg Glu
        435                 440                 445

Gly Asn Ser Ser Gln Asn Trp Gln Arg Phe Tyr Gln Leu Thr Lys Leu
    450                 455                 460

Leu Asp Ser Met His Glu Val Val Glu Asn Leu Leu Thr Tyr Cys Phe
465                 470                 475                 480

Gln Thr Phe Leu Asp Lys Thr Met Ser Ile Glu Phe Pro Glu Met Leu
                485                 490                 495

Ala Glu Ile Ile Thr Asn Gln Ile Pro Lys Tyr Ser Asn Gly Asn Thr
            500                 505                 510

Lys Lys Leu Leu Phe His Gln Lys
                515                 520

<210> SEQ ID NO 8
<211> LENGTH: 244
<212> TYPE: PRT
<213> ORGANISM: Aequorea victoria
<220> FEATURE:
<223> OTHER INFORMATION: GFP

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Gly Ile Leu

<210> SEQ ID NO 9
<211> LENGTH: 603
<212> TYPE: PRT
<213> ORGANISM: Escherichia coli
<220> FEATURE:
<223> OTHER INFORMATION: GUS

<400> SEQUENCE: 9

Met Val Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
                20                  25                  30

Arg Trp Trp Glu Ser Ala Leu Gln Glu Ser Arg Ala Ile Ala Val Pro
            35                  40                  45

Gly Ser Phe Asn Asp Gln Phe Ala Asp Ala Asp Ile Arg Asn Tyr Ala
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
```

```
            195                 200                 205
Asn Gly Asp Val Ser Val Glu Leu Arg Asp Ala Asp Gln Gln Val Val
            210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
            245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
            275                 280                 285
Tyr Phe Thr Gly Phe Gly Arg His Glu Asp Ala Asp Leu Arg Gly Lys
            290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
            325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
            355                 360                 365
Asn Lys Pro Lys Glu Leu Tyr Ser Glu Ala Val Asn Gly Glu Thr
            370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
            405                 410                 415
Arg Pro Gln Gly Ala Arg Glu Tyr Phe Ala Pro Leu Ala Glu Ala Thr
            420                 425                 430
Arg Lys Leu Asp Pro Thr Arg Pro Ile Thr Cys Val Asn Val Met Phe
            435                 440                 445
Cys Asp Ala His Thr Asp Thr Ile Ser Asp Leu Phe Asp Val Leu Cys
450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
            485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Glu Tyr Gln Cys Ala
            515                 520                 525
Trp Leu Asp Met Tyr His Arg Val Phe Asp Arg Val Ser Ala Val Val
            530                 535                 540
Gly Glu Gln Val Trp Asn Phe Ala Asp Phe Ala Thr Ser Gln Gly Ile
545                 550                 555                 560
Leu Arg Val Gly Gly Asn Lys Lys Gly Ile Phe Thr Arg Asp Arg Lys
            565                 570                 575
Pro Lys Ser Ala Ala Phe Leu Leu Gln Lys Arg Trp Thr Gly Met Asn
            580                 585                 590
Phe Gly Glu Lys Pro Gln Gln Gly Gly Lys Gln
            595                 600
```

<210> SEQ ID NO 10

<211> LENGTH: 535
<212> TYPE: PRT
<213> ORGANISM: Photinus pyralis
<220> FEATURE:
<223> OTHER INFORMATION: LUC

<400> SEQUENCE: 10

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

```
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Lys Ser Leu Ile Lys Tyr Lys Gly Tyr
            420                 425                 430

Gln Val Ala Pro Ala Glu Leu Glu Ser Ile Leu Leu Gln His Pro Asn
        435                 440                 445

Ile Phe Asp Ala Gly Val Ala Gly Leu Pro Asp Asp Ala Gly Glu
    450                 455                 460

Leu Pro Ala Ala Val Val Val Leu Glu His Gly Lys Thr Met Thr Glu
465                 470                 475                 480

Lys Glu Ile Val Asp Tyr Val Ala Ser Gln Val Thr Thr Ala Lys Lys
                485                 490                 495

Leu Arg Gly Gly Val Val Phe Val Asp Glu Val Pro Lys Gly Leu Thr
            500                 505                 510

Gly Lys Leu Asp Ala Arg Lys Ile Arg Glu Ile Leu Ile Lys Ala Lys
        515                 520                 525

Lys Gly Gly Lys Ile Ala Val
    530                 535
```

<210> SEQ ID NO 11
<211> LENGTH: 699
<212> TYPE: DNA
<213> ORGANISM: artificial sequence
<220> FEATURE:
<223> OTHER INFORMATION: a DNA sequence encoding the yeast GAL4 DNA binding domain and the herpes simplex virus VP16 protein

<400> SEQUENCE: 11

```
atggggctac tgtcttctat cgaacaagca tgcgatattt gccgacttaa aaagctcaag    60
tgctccaaag aaaaaccgaa gtgcgccaag tgtctgaaga caactgggag gtgtcgctac   120
tctcccaaaa ccaaaaggtc tccgctgact agggcacatc tgacagaagt ggaatcaagg   180
ctagaaaagac tggaacagct atttctactg attttttcctc gagaagacct tgacatgatt   240
ttgaaaatgg attcttttaca ggatataaaa gcattgttaa caggattatt tgtacaagat   300
aatgtgaata agatgccgt cacagataga ttggcttcag tggagactga tatgcctcta   360
acattgagac agcatagaat aagtgcgaca tcatcatcgg aagagagtag taacaaaggt   420
caaagacagt tgactgtatc gccggaattc ccggggatct gggccccccc gaccgatgtc   480
agcctggggg acgagctcca cttagacggc gaggacgtgg cgatggcgca tgccgacgcg   540
ctagacgatt tcgatctgga catgttgggg gacggggatt ccccgggtcc gggatttacc   600
ccccacgact ccgcccccta cggcgctctg gatatggccg acttcgagtt tgagcagatg   660
tttaccgatg cccttggaat tgacgagtac ggtgggtga                          699
```

<210> SEQ ID NO 12
<211> LENGTH: 232
<212> TYPE: PRT
<213> ORGANISM: artificial sequence
<220> FEATURE:
<223> OTHER INFORMATION: a translational fusion of the yeast GAL4 DNA binding domain and the herpes simplex virus VP16 protein

<400> SEQUENCE: 12

```
Met Gly Leu Leu Ser Ser Ile Glu Gln Ala Cys Asp Ile Cys Arg Leu
1               5                   10                  15
```

```
Lys Lys Leu Lys Cys Ser Lys Glu Lys Pro Lys Cys Ala Lys Cys Leu
             20                  25                  30
Lys Asn Asn Trp Glu Cys Arg Tyr Ser Pro Lys Thr Lys Arg Ser Pro
         35                  40                  45
Leu Thr Arg Ala His Leu Thr Glu Val Glu Ser Arg Leu Glu Arg Leu
 50                  55                  60
Glu Gln Leu Phe Leu Leu Ile Phe Pro Arg Glu Asp Leu Asp Met Ile
 65                  70                  75                  80
Leu Lys Met Asp Ser Leu Gln Asp Ile Lys Ala Leu Leu Thr Gly Leu
                 85                  90                  95
Phe Val Gln Asp Asn Val Asn Lys Asp Ala Val Thr Asp Arg Leu Ala
                100                 105                 110
Ser Val Glu Thr Asp Met Pro Leu Thr Leu Arg Gln His Arg Ile Ser
             115                 120                 125
Ala Thr Ser Ser Ser Glu Glu Ser Ser Asn Lys Gly Gln Arg Gln Leu
130                 135                 140
Thr Val Ser Pro Glu Phe Pro Gly Ile Trp Ala Pro Pro Thr Asp Val
145                 150                 155                 160
Ser Leu Gly Asp Glu Leu His Leu Asp Gly Glu Asp Val Ala Met Ala
                 165                 170                 175
His Ala Asp Ala Leu Asp Asp Phe Asp Leu Asp Met Leu Gly Asp Gly
             180                 185                 190
Asp Ser Pro Gly Pro Gly Phe Thr Pro His Asp Ser Ala Pro Tyr Gly
             195                 200                 205
Ala Leu Asp Met Ala Asp Phe Glu Phe Glu Gln Met Phe Thr Asp Ala
 210                 215                 220
Leu Gly Ile Asp Glu Tyr Gly Gly
225                 230
```

<210> SEQ ID NO 13
<211> LENGTH: 864
<212> TYPE: DNA
<213> ORGANISM: Rattus norvegicus
<220> FEATURE:
<223> OTHER INFORMATION: the DNA sequence encoding the ligand binding domain of GR

<400> SEQUENCE: 13

```
gaagctcgaa aaacaaagaa aaaaatcaaa gggattcagc aagccactgc aggagtctca      60
caagacactt cggaaaatcc taacaaaaca atagttcctg cagcattacc acagctcacc     120
cctaccttgg tgtcactgct ggaggtgatt gaacccgagg tgttgtatgc aggatatgat     180
agctctgttc cagattcagc atggagaatt atgaccacac tcaacatgtt aggtgggcgt     240
caagtgattg cagcagtgaa atgggcaaag gcgataccag gcttcagaaa cttacacctg     300
gatgaccaaa tgaccctgct acagtactca tggatgtttc tcatggcatt tgccctgggt     360
tggagatcat acagacaatc aagtggaaac ctgctctgct tgctcctga tctgattatt     420
aatgagcaga gaatgtctct accctgcatg tatgaccaat gtaaacacat gctgtttgtc     480
tcctctgaat acaaagatt gcaggtatcc tatgaagagt atctctgtat gaaaaccta     540
ctgcttctct cctcagttcc taaggaaggt ctgaagagcc aagagttatt tgatgagatt     600
cgaatgactt atatcaaaga gctaggaaaa gccatcgtca aagggaagg gaactccagt     660
cagaactggc aacggtttta ccaactgaca aagcttctgg actccatgca tgaggtggtt     720
gagaatctcc ttacctactg cttccagaca ttttttggata agaccatgag tattgaattc     780
```

```
ccagagatgt tagctgaaat catcactaat cagataccaa atattcaaa tggaaatacc    840 aaaaagcttc tgtttcatca aaaa                                          864
```

<210> SEQ ID NO 14
<211> LENGTH: 252
<212> TYPE: PRT
<213> ORGANISM: Rattus norvegicus
<220> FEATURE:
<223> OTHER INFORMATION: the ligand binding domain of GR

<400> SEQUENCE: 14

```
Pro Gln Leu Thr Pro Thr Leu Val Ser Leu Leu Glu Val Ile Glu Pro
1               5                   10                  15

Glu Val Leu Tyr Ala Gly Tyr Asp Ser Ser Val Pro Asp Ser Ala Trp
            20                  25                  30

Arg Ile Met Thr Thr Leu Asn Met Leu Gly Gly Arg Gln Val Ile Ala
        35                  40                  45

Ala Val Lys Trp Ala Lys Ala Ile Pro Gly Phe Arg Asn Leu His Leu
    50                  55                  60

Asp Asp Gln Met Thr Leu Leu Gln Tyr Ser Trp Met Phe Leu Met Ala
65                  70                  75                  80

Phe Ala Leu Gly Trp Arg Ser Tyr Arg Gln Ser Ser Gly Asn Leu Leu
                85                  90                  95

Cys Phe Ala Pro Asp Leu Ile Ile Asn Glu Gln Arg Met Ser Leu Pro
            100                 105                 110

Cys Met Tyr Asp Gln Cys Lys His Met Leu Phe Val Ser Ser Glu Leu
        115                 120                 125

Gln Arg Leu Gln Val Ser Tyr Glu Glu Tyr Leu Cys Met Lys Thr Leu
    130                 135                 140

Leu Leu Leu Ser Ser Val Pro Lys Glu Gly Leu Lys Ser Gln Glu Leu
145                 150                 155                 160

Phe Asp Glu Ile Arg Met Thr Tyr Ile Lys Glu Leu Gly Lys Ala Ile
                165                 170                 175

Val Lys Arg Glu Gly Asn Ser Ser Gln Asn Trp Gln Arg Phe Tyr Gln
            180                 185                 190

Leu Thr Lys Leu Leu Asp Ser Met His Glu Val Val Glu Asn Leu Leu
        195                 200                 205

Thr Tyr Cys Phe Gln Thr Phe Leu Asp Lys Thr Met Ser Ile Glu Phe
    210                 215                 220

Pro Glu Met Leu Ala Glu Ile Ile Thr Asn Gln Ile Pro Lys Tyr Ser
225                 230                 235                 240

Asn Gly Asn Thr Lys Lys Leu Leu Phe His Gln Lys
                245                 250
```

<210> SEQ ID NO 15
<211> LENGTH: 606
<212> TYPE: DNA
<213> ORGANISM: Escherichia coli
<220> FEATURE:
<223> OTHER INFORMATION: the DNA sequence encoding the DNA binding
      domain of LexA

<400> SEQUENCE: 15

```
atggaagcgt taacggccag gcaacaagag gtgtttgatc tcatccgtga tcacatcagc    60
cagacaggta tgccgccgac gcgtgcggaa atcgcgcagc gtttgggggtt ccgttccccca   120 aacgcggctg aagaacatct gaaggcgctg gcacgcaaag gcgttattga aattgtttcc   180
```

```
ggcgcatcac gcgggattcg tctgttgcaa gaagaggaag aagggttgcc gctggtaggt      240
cgtgtggctg ccggtgaacc acttctggcg caacagcata ttgaaggtca ttatcaggtc      300
gatccttcct tattcaagcc gaatgctgat ttcctgctgc gcgtcagcgg gatgtcgatg      360
aaagatatcg gcattatgga tggtgacttg ctggcagtgc ataaaactca ggatgtacgt      420
aacggtcagg tcgttgtcgc acgtattgat gacgaggtta ccgttaagcg cctgaaaaaa      480
cagggcaata aagtcgaact gttgccagaa aatagcgagt ttaaaccaat tgtcgtagat      540
cttcgtcagc agagcttcac cattgaaggg ctggcggttg gggttattcg caacggcgac      600
tggctg                                                                 606
```

<210> SEQ ID NO 16
<211> LENGTH: 202
<212> TYPE: PRT
<213> ORGANISM: Escherichia coli
<220> FEATURE:
<223> OTHER INFORMATION: the DNA binding domain of LexA

<400> SEQUENCE: 16

```
Met Glu Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 17
<211> LENGTH: 441
<212> TYPE: DNA
<213> ORGANISM: Saccharomyces cerevisiae
<220> FEATURE:
<223> OTHER INFORMATION: the DNA sequence encoding the DNA binding
      domain of Gal4

<400> SEQUENCE: 17

```
atggggctac tgtcttctat cgaacaagca tgcgatattt gccgacttaa aaagctcaag      60
```

```
tgctccaaag aaaaaccgaa gtgcgccaag tgtctgaaga caactgggag gtgtcgctac    120
tctcccaaaa ccaaaaggtc tccgctgact agggcacatc tgacagaagt ggaatcaagg    180
ctagaaagac tggaacagct atttctactg attttcctc gagaagacct tgacatgatt     240
ttgaaaatgg attctttaca ggatataaaa gcattgttaa caggattatt tgtacaagat    300
aatgtgaata agatgccgt cacagataga ttggcttcag tggagactga tatgcctcta     360
acattgagac agcatagaat aagtgcgaca tcatcatcgg aagagagtag taacaaaggt    420
caaagacagt tgactgtatc g                                              441
```

<210> SEQ ID NO 18
<211> LENGTH: 147
<212> TYPE: PRT
<213> ORGANISM: Saccharomyces cerevisiae
<220> FEATURE:
<223> OTHER INFORMATION: the DNA binding domain of Gal4

<400> SEQUENCE: 18

```
Met Gly Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145
```

<210> SEQ ID NO 19
<211> LENGTH: 336
<212> TYPE: DNA
<213> ORGANISM: Saccharomyces cerevisiae
<220> FEATURE:
<223> OTHER INFORMATION: the DNA sequence encoding the activation domain
      of Gal4

<400> SEQUENCE: 19

```
aattttaatc aaagtgggaa tattgctgat agcgcattgt ccttcacttt cactaacagt    60
agcaacggtc cgaacctcat aacaactcaa acaaattctc aagcgctttc acaaccaatt    120
gcctcctcta acgttcatga aacttcatg aataatgaaa tcacggctag taaaattgat     180
gatggtaata attcaaaacc actgtcacct ggttggacgg accaaactgc gtataacgcg    240
tttggaatca ctacagggat gtttaatacc actacaatgg atgatgtata taactatcta   300
ttcgatgatg aagataccccc accaaaccca aaaaaa                              336
```

<210> SEQ ID NO 20

<211> LENGTH: 112
<212> TYPE: PRT
<213> ORGANISM: Saccharomyces cerevisiae
<220> FEATURE:
<223> OTHER INFORMATION: the activation domain of Gal4

<400> SEQUENCE: 20

```
Asn Phe Asn Gln Ser Gly Asn Ile Ala Asp Ser Ala Leu Ser Phe Thr
1               5                   10                  15

Phe Thr Asn Ser Ser Asn Gly Pro Asn Leu Ile Thr Thr Gln Thr Asn
            20                  25                  30

Ser Gln Ala Leu Ser Gln Pro Ile Ala Ser Ser Asn Val His Asp Asn
        35                  40                  45

Phe Met Asn Asn Glu Ile Thr Ala Ser Lys Ile Asp Asp Gly Asn Asn
    50                  55                  60

Ser Lys Pro Leu Ser Pro Gly Trp Thr Asp Gln Thr Ala Tyr Asn Ala
65                  70                  75                  80

Phe Gly Ile Thr Thr Gly Met Phe Asn Thr Thr Thr Met Asp Asp Val
                85                  90                  95

Tyr Asn Tyr Leu Phe Asp Asp Glu Asp Thr Pro Pro Asn Pro Lys Lys
            100                 105                 110
```

<210> SEQ ID NO 21
<211> LENGTH: 234
<212> TYPE: DNA
<213> ORGANISM: herpes simplex virus
<220> FEATURE:
<223> OTHER INFORMATION: the DNA sequence encoding VP16

<400> SEQUENCE: 21

```
gcccccccga ccgatgtcag cctgggggac gagctccact tagacggcga ggacgtggcg    60
atggcgcatg ccgacgcgct agacgatttc gatctggaca tgttggggga cgggattcc   120 ccgggtccgg gatttacccc ccacgactcc gcccctacg gcgctctgga tatggccgac   180
ttcgagtttg agcagatgtt taccgatgcc cttggaattg acgagtacgg tggg        234
```

<210> SEQ ID NO 22
<211> LENGTH: 78
<212> TYPE: PRT
<213> ORGANISM: herpes simplex virus
<220> FEATURE:
<223> OTHER INFORMATION: VP16

<400> SEQUENCE: 22

```
Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly Gly
65                  70                  75
```

<210> SEQ ID NO 23
<211> LENGTH: 14
<212> TYPE: PRT
<213> ORGANISM: Arabidopsis thaliana
<220> FEATURE:
<221> NAME/KEY: misc_feature

```
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<223> OTHER INFORMATION: EDLL domain

<400> SEQUENCE: 23

Glu Xaa Xaa Xaa Xaa Asp Xaa Xaa Xaa Leu Xaa Xaa Xaa Leu
1               5                   10

<210> SEQ ID NO 24
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Leu or Phe
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
<223> OTHER INFORMATION: Xaa can be Asp or Asn
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain

<400> SEQUENCE: 24

Glu Xaa Xaa Xaa Xaa Asp Xaa Xaa Xaa Leu Xaa Xaa Xaa Leu
1               5                   10

<210> SEQ ID NO 25
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Phe or Leu
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
```

```
<223> OTHER INFORMATION: Xaa can be Asp or Asn
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be Val or Leu
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain consensus sequence
      E-F/L-X-X-L/F-D-D/N-X-V/L/I-L-X-X-L/M-L

<400> SEQUENCE: 25

Glu Xaa Xaa Xaa Xaa Asp Xaa Xaa Xaa Leu Xaa Xaa Xaa Leu
1               5                   10

<210> SEQ ID NO 26
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Phe or Leu
<220> FEATURE:
<221> NAME/KEY: misc_feature
<222> LOCATION: (3)..(3)
<223> OTHER INFORMATION: Xaa can be Glu or Val
<220> FEATURE:
<221> NAME/KEY: misc_feature
<222> LOCATION: (4)..(4)
<223> OTHER INFORMATION: Xaa can be Tyr, Cys, or Phe
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
<223> OTHER INFORMATION: Xaa can be Asp or Asn
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be Val or Leu
<220> FEATURE:
<221> NAME/KEY: misc_feature
<222> LOCATION: (11)..(11)
<223> OTHER INFORMATION: Xaa can be Glu, Gln, or Asp
<220> FEATURE:
<221> NAME/KEY: misc_feature
<222> LOCATION: (12)..(12)
<223> OTHER INFORMATION: Xaa can be Glu, Asp, or Ser
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain consensus sequence
      E-F/L-E/V-Y/C/F-L/F-D-D/N-X-V/L-L-E/Q/D-E/D/S-L/M-L

<400> SEQUENCE: 26

Glu Xaa Xaa Xaa Xaa Asp Xaa Xaa Xaa Leu Xaa Xaa Xaa Leu
1               5                   10
```

<210> SEQ ID NO 27
<211> LENGTH: 699
<212> TYPE: DNA
<213> ORGANISM: artificial sequence
<220> FEATURE:
<223> OTHER INFORMATION: a DNA sequence encoding a translational fusion
of the yeast GAL4 DNA binding domain and the herpes simplex virus
VP16 protein

<400> SEQUENCE: 27

```
atggggctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
aatgtgaata agatgccgt cacagataga ttggcttcag tggagactga tatgcctcta     360
acattgagac agcatagaat aagtgcgaca tcatcatcgg aagagagtag taacaaaggt     420
caaagacagt tgactgtatc gccggaattc ccggggatct gggccccccc gaccgatgtc     480
agcctggggg acgagctcca cttagacggc gaggacgtgg cgatggcgca tgccgacgcg     540
ctagacgatt tcgatctgga catgttgggg acggggatt ccccgggtcc gggatttacc     600
ccccacgact ccgccccta cggcgctctg gatatggccg acttcgagtt tgagcagatg     660
tttaccgatg cccttggaat tgacgagtac ggtgggtga                            699
```

<210> SEQ ID NO 28
<211> LENGTH: 232
<212> TYPE: PRT
<213> ORGANISM: artificial sequence
<220> FEATURE:
<223> OTHER INFORMATION: a translational fusion of the yeast GAL4 DNA
binding domain and the herpes simplex virus VP16 protein

<400> SEQUENCE: 28

```
Met Gly Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Trp Ala Pro Pro Thr Asp Val
145                 150                 155                 160

Ser Leu Gly Asp Glu Leu His Leu Asp Gly Glu Asp Val Ala Met Ala
```

|     |     |     |     |     | 165 |     |     |     | 170 |     |     |     |     | 175 |
| --- | --- | --- | --- | --- | --- | --- | --- | --- | --- | --- | --- | --- | --- | --- |

His Ala Asp Ala Leu Asp Asp Phe Asp Leu Asp Met Leu Gly Asp Gly
        180                       185                       190

Asp Ser Pro Gly Pro Gly Phe Thr Pro His Asp Ser Ala Pro Tyr Gly
    195                      200                    205

Ala Leu Asp Met Ala Asp Phe Glu Phe Glu Gln Met Phe Thr Asp Ala
  210                     215                    220

Leu Gly Ile Asp Glu Tyr Gly Gly
225                230

<210> SEQ ID NO 29
<211> LENGTH: 766
<212> TYPE: DNA
<213> ORGANISM: Arabidopsis thaliana
<220> FEATURE:
<223> OTHER INFORMATION: SEQ ID NO: 29 Contains promoter fragment from
    prAT1G16850, found in GenBank acc. NC_003070)

<400> SEQUENCE: 29

```
attgggtacg attttcatag gtctttcctc acgccagaag tgttgtttta ttttgttgat    60
tgagttatta attattggaa gcttttcttt caagcaaagt aaaatgcgta ataatgatta   120
gtcacatcca atggttagtc agtctattac accgttaatc aagctctggt catataattt   180
tttattttt ggaactaaca cttattagtt taggtttcca tcacctattt aattcgtaat    240
tcttatacat gcatataata gagatacata tatacaaatt tatgatcatt tttgcacaac   300
atgtgatctc attcattagt atgcattatg cgaaaacctc gacgcgcaaa agacacgtaa   360
tagctaataa tgttactcat ttataatgat tgaagcaaga cgaaaacaac aacatatata   420
tcaaattgta aactagatat ttcttaaaag tgaaaaaaaa caagaaaata taaaggacaa   480
ttttgagtca gtctcttaat attaaaacat atatacataa ataagcacaa acgtggttac   540
ctgtcttcat gcaatgtgga ctttagttta tctaatcaaa atcaaaataa aaggtgtaat   600
agttctcgtc atttttcaaa ttttaaaaat cagaaccaag tgattttttgt ttgagtattg   660
atccattgtt taaacaattt aacacagtat atacgtctct tgagatgttg acatgatgat   720
aaaatacgag atcgtctctt ggttttcgaa ttttgaactt taatag             766
```

<210> SEQ ID NO 30
<211> LENGTH: 605
<212> TYPE: DNA
<213> ORGANISM: Arabidopsis thaliana
<220> FEATURE:
<223> OTHER INFORMATION: SEQ ID NO: 30 Contains promoter fragment from
    prAt5g52300, found in Genbank acc. no. AB019226, GI:3869065)

<400> SEQUENCE: 30

```
tgatgatgat gatgaagaag agaacgaatt ttgaaattgg cggttttgaa tttttaagaa    60
attaaaaaat atccccccgtc gatttcaaga gggagatgga gataccaaag caactctcgc   120
cacttgtcgt cttttaattt taattgagta cgttatgccg ttttaaatgt tcaaaacagc   180
acacagttga tagctgaatt gattttttct tttgccgttt tgttatattt aaacaacaca   240
cagtgcattt gccaaataac tacatgatgg gccaataaac gtggaccgac taaaactaaa   300
taatagaaga tacatcgata ggcttctcta aagatcggat aaaagataat gtcgcatagc   360
cacgtagaga gcaactggct gagacgtggc aggacgaaac ggacgcatcg tacgtgtcag   420
aatcctacag aagtaaagag acagaagcca gagagaggtg gttcggccat atgtcatcgt   480
tctctctata aactttatgg aactttgttc tgattttctc agagacacga aaagaaagaa   540
```

```
aacaacacta gaacaaagag ggtttgattg attcacttga aaaagagaaa acacagcttt      600
ggaaa                                                                  605
```

<210> SEQ ID NO 31
<211> LENGTH: 907
<212> TYPE: DNA
<213> ORGANISM: Arabidopsis thaliana
<220> FEATURE:
<223> OTHER INFORMATION: SEQ ID NO: 31 Contains promoter fragment from
      prAt3g46230, found in Genbank acc. no. AL355775, GI:7798991)

<400> SEQUENCE: 31

```
ttatttattc tcaattttcc catacgaatt ttttgtcttt atatttatca caaaaaaga       60 gtttgctctt taaaaaacta tactaatgta atttttttat tttattttct ctatcttaat     120
cggatattaa tccgactctt cttcttccca aaaattaata ttagtttcaa atccaaagca     180
acccacctca ttcaactttc cttcgatttt cttcaaattt ccagtttcca cttgctttca     240
ttgcttcttt cccgccgttt ctagatcttc aatcgagaaa gggatttgca acttttcaca     300
caaaaatctt agattaattg ttattaataa cttgttcatc aaaccactaa aaatcccgtg     360
tcatcttcga cttcttggtt aaaattcaat aaagagtgta acttttcatt gctataactt     420
aataatttgt ttgtgagaag agaactctag tcttacaggg accaacacca acaatcaaaa     480
tttagataat gaagaatagt tgctgatgca tgattaagat tgaatttatc aacaaaagat     540
aagtgttcat tatacaacac gtgattaatt gcatggtgta ttaaggccca ttaacgaagt     600
ccatggtaaa atgaaacggc atggcgttca ctaccccacc taatgaactg catgtcgtct     660
caaccatcaa catagaagct tcttgaagcc acctgagaaa tctggtagcg acactcttga     720
aagacacgtt ataagaaac ggaagaagaa aacctgaaat ttcaagaaac ttgcagagct     780
ttctatctct tatcctcttc tctaccatca tttctcccta taaatacgcc aacgcacata     840
agtgtttgca ttcgaagaga gttctagcaa aacaaaacaa acagagcaa acagagtaag     900 cgaaacg                                                               907
```

<210> SEQ ID NO 32
<211> LENGTH: 780
<212> TYPE: DNA
<213> ORGANISM: Arabidopsis thaliana
<220> FEATURE:
<223> OTHER INFORMATION: SEQ ID NO: 32 Contains promoter fragment from
      prAT1G52690, found in Genbank acc. AC008016)

<400> SEQUENCE: 32

```
agaaagtgta tattttagta aaatcctaaa tctaagcatt acactaacac gtggaaaata      60
acataccatt gacgattgac atggctaatt ttttgtggag gtgaatagtt tgaggattta     120
ttaccctaac gttgcttggt caagaagtga agtaggatga caggcaatag gaagatctta     180 aaccttttt tccggtgaca attatttatg actttttatt gttgtcaaaa aatatattat     240
cagtaatata tcaataacga atacaataaa aactcatccg atcgattttc aagaatttat     300
agctatatta aaattacttc gaatccatgt aagaattgtg tattggttct ttttagaaaa     360
aagtaaatat ctatgcagta atggcggttg cataatatat gccttgagta gatgaatatc     420
caatatcaag ataacgtgag tcaccacgtg tctaacatct tccgtagctc cgttttacc     480 atgacgtgtc acatagatat aggtcatcat gaaaacgaga aacctaactt taacactcgc     540
acataactcc aagtttcgaa acttcgtcac atcaacctaa tcggggcacg tacctacaca     600
```

```
cctgtcgcga aactgcaaca cctatcttgt tctctcgccg accaagactt gctataaata      660
actctgacta acgagtcgga gacaactcac agttccaaac acacaaaaaa cacaagatct      720
aaaaaaaaaa gcttttatca tttagaaaaa tttggtttcg aatttcttcg aagagtgaaa      780
```

<210> SEQ ID NO 33
<211> LENGTH: 447
<212> TYPE: DNA
<213> ORGANISM: Arabidopsis thaliana
<220> FEATURE:
<223> OTHER INFORMATION: SEQ ID NO: 33 Contains promoter fragment from
      prAt2g37870, found in Genbank acc. no. AC007661, GI:6598780)

<400> SEQUENCE: 33

```
aaaccatatg ttgttgtagc ctactcattt ctatctgttt tactacattt ccgttgttat       60
atctaataat aagaattttc agctcgaatg ttgaatcctt atagtgtcta tattgaaaca      120
atgaaaacca aaagtgttct gaaacaaaga gagtgcaaaa agttgttgga gcctgtttta      180
tgaaagaaaa gtaaagagag aaacaaaaac aaacacgcaa gaaatcaaac gactaaacac      240
acaacagatg gtgaaatcta atcaaagta agcataaatc aaatgattac agaatggggg      300
aaaaaattaa acggtataac cgtacacgtc accaaaacac aaccacccca ctaaaacatc      360
ttactagtta ctagtatata agaatcatca acgcactaag taagacactc aacaaaacaa      420
aacaagaagg agaatataag aagaagc                                          447
```

<210> SEQ ID NO 34
<211> LENGTH: 776
<212> TYPE: DNA
<213> ORGANISM: Arabidopsis thaliana
<220> FEATURE:
<223> OTHER INFORMATION: SEQ ID NO: 34 Contains promoter fragment from
      prAT5G43840 or prG1947, found in Genbank acc. AB026651,
      GI:4757407)

<400> SEQUENCE: 34

```
cgattttcga ataaattatt tgagctttcc aaactgtaat tcaagtatta ttacttatat       60
agtgttagtg tacttcaaaa gttaaagcat aaattttctt atatttgaaa tgacctcttc      120
tttacaaaat cttcttaaaa ttatgcatta tcaatatatt aattgtatat atatatataa      180
tgtataattc tgcttgtgtc gtgcttaacc gtttgatttg gtgtggttag atctggtttt      240
cccccaaccc aattcaattg aatcaaggat caatcaaatt ttcaaaggat actcttgttc      300
tctacacaaa tctttcaaag ggttccacca aaaatcccat cattctgact tcagaataaa      360
caaacaaacc acgaaacgta tctctatgca ttcactacaa cgtgtcatgg gcgaaaacga      420
agcttataaa tgttggagca tagtcactaa atttataatg attaattaaa ttttagattt      480
tctgatattc atagaagaca aaagaacaca aaagtagcat cttccaatga atgtatgaca      540
ctatgatctc tcatttccat ttatagcaaa tcggctttgt ccacatcaaa gataactaat      600
aaatagactt atccaaaaca ctcaaaagca atacatttct atccaaaaat attaaacccc      660
aaaaatatag acagcataaa agcatcctca agcttcagct attcatcaca actattctct      720
cctctctctt tttttattaa aaaagctcaa atttatatag gttttttgtt cacaaa          776
```

<210> SEQ ID NO 35
<211> LENGTH: 928
<212> TYPE: DNA
<213> ORGANISM: Arabidopsis thaliana
<220> FEATURE:
<223> OTHER INFORMATION: SEQ ID NO: 35 Contains promoter fragment from
      prAt5g66780, found in Genbank acc. no. AB010700, GI:2828185)

<400> SEQUENCE: 35

```
tagtcttgtt gttttctcat tagataattt aaactggttt gcttctttat ttttggttgg      60
ataaagtgac cggttctggt catctgtttg agatgtaatt actatttcat aaaattagga     120
agttgaaagc caaatatatt tgtaactact ctttttatttg taattttgct caaaaaagtg    180
atgaaatgta gttttgatat atgaatatct accattatac ataagtatat ctgaacatgg    240
tacaacttat gaaagctaaa tgtcaatact tgcaaagata taacaaatac aagttacatg    300
aataagagat gtgtgttgaa tttataagtg tcattttctt ttcactttaa aacaaacttc    360
atcttctttt gtttcttatg tgtcaaagtt gccacagttg ctctatttga gtctttcagt    420
gtcagtctca gtcactgtac tgattttact tttttttgtt gagtgtgcca atgatgacat    480
cactcccacg tcctccatcc gtcttctttt aacggtcacg tggctcccac cctcttttct    540
cgatgtcttt accgacttgt tctagcccaa cttacttggg ccatttagat ttttggtgg     600
cccaagttgc taaagagga tttatcatag aaatctgaac ccgttgcagc gctcaacaca     660
tgtcacagtc ctgacaaaca cgtattcaaa tccttgttaa gtcccgccac ctgtcaccag    720
agcaccacga ggcaaactct gatcaggaca ccgtcgtact attatgtcgg aagacaggaa    780
agcttaatta agcttaaacc tgacgtattt aacttcgtta actctacctt actaaagggt    840
tttaatttaa aacttatcat ctcctcgtaa gaataaaaac tacttactct ataaatttaa    900
gcttcaagaa acctccaaaa gcagagaa                                        928
```

<210> SEQ ID NO 36
<211> LENGTH: 460
<212> TYPE: DNA
<213> ORGANISM: Arabidopsis thaliana
<220> FEATURE:
<223> OTHER INFORMATION: SEQ ID NO: 36 Contains promoter fragment from
     prAt3g17520, found in Genbank acc. no. AB022219, GI:7321075)

<400> SEQUENCE: 36

```
gggtttact tacaataagc ccttactatt cattgaaaag ctcactaaac ttgtttatga      60
aaagcccact ggttattgta tacaagccca ttagcttcac agatgtgttt cagttgaagc   120
ctctctttgt ttttgcgagt cggttttccg caaaaagcaa tcgcttgcct cgttgtttgt   180
gtaacacgtg tcaagaacca cttaacacga atccaaaatc gagaagccaa aagaagctgg   240
tactcgccac gtacttagcc acgcgtccta aacctatctc ttttttcaact aatacataac  300
agagaagcaa tcacagcacc attcctcgga gaacacatca cagtaaacag aggttttttt   360
cttcttctga aacttgatat aagttatata accatataat attttgtgtt cgattagtgt   420
aacaaaaatg gggttagaga ggaaagtgta cggtttggtt                           460
```

<210> SEQ ID NO 37
<211> LENGTH: 936
<212> TYPE: DNA
<213> ORGANISM: Arabidopsis thaliana
<220> FEATURE:
<223> OTHER INFORMATION: SEQ ID NO: 37 Contains promoter fragment from
     prAt4g09600, found in Genbank acc. no. AL161831, GI:7321075)

<400> SEQUENCE: 37

```
gttaaatcct cactaggatc tctctttata ttaatggtta aaaacatatg catgttttgt      60
gttttttgcat cttctttttc atagacaaaa gcaagatgag tcttagaagg acatcaatgt   120
catagacatg gctttagtat cttttgagtg tgctttaaat gatgatgatt taccctgaac   180
```

```
ctgaaatttt acctattaat taatttaagt gtgcgttaaa ccataaacca tatactctga      240
acctgaaatt ggttctaaag cacaacctaa acttgagatt ggagaatgct ttaaaaggaa      300
aaaaaaatca aaggaaacca ttaatgagcc atcaaaaaat attcactaat atgacaagat      360
gcattgttta ttttctttt cagaatcctc agaaactacc actaaactcc tcaaggaaca       420
aaaccatatc atgaattagg ctggcaattt aactctgaga cgtctttctt gtatagagaa      480
taaaacatac gcgtgtaaaa gaaacgcgt gaatcgaatg atgagtgtta acgttcgatc       540
gagatgccac caaatctttt cattaaaatg aattgtggag gacataccac ttttaacgag      600
gtcatttcca ctgggtgaca tgtggactct actttgggtg gcatgttcat atctttccac      660
atcaccatgt aaacgtgaaa acacccacca cactcactta catctcaaac acatgtcttc      720
attatcgtac gtagctccaa aaaaaaaaat gaaaactagg tttagtgatt ctatttcgca      780
atgtataata tacaacttgt aaaaataaaa tatttgaata agcattataa ataaacccaa      840
agaggtgtta gatttatata cttaattgta gctactaaat agagaatcag agagaatagt      900
tttatatctt gcacgaaact gcatgctttt tgagac                                936

<210> SEQ ID NO 38
<211> LENGTH: 1510
<212> TYPE: DNA
<213> ORGANISM: arabidopsis thaliana
<220> FEATURE:
<223> OTHER INFORMATION: SEQ ID NO: 38 Contains promoter fragment from
      prAt5g52310 RD29 promoter

<400> SEQUENCE: 38
ggttgctatg gtagggacta tggggttttc ggattccggt ggaagtgagt ggggaggcag      60
tggcggaggt aagggagttc aagattctgg aactgaagat ttgggttttt gcttttgaat     120
gtttgcgttt ttgtatgatg cctctgtttg tgaactttga tgtatttat ctttgtgtga      180 aaaagagatt gggttaataa atatttgct ttttggata agaaactctt ttagcggccc       240
attaataaag gttacaaatg caaaatcatg ttagcgtcag atatttaatt attcgaagat     300
gattgtgata gatttaaaat tatcctagtc aaaagaaag agtaggttga gcagaaacag      360
tgacatctgt tgtttgtacc atacaaatta gtttagatta ttggttaaca tgttaaatgg     420
ctatgcatgt gacatttaga ccttatcgga attaatttgt agaattatta attaagatgt     480
tgattagttc aaacaaaaat tttatattaa aaaatgtaaa cgaatatttt gtatgttcag     540
tgaaagtaaa acaaattaaa ttaacaagaa acttatagaa gaaattttt actatttaag     600 agaaagaaaa aaatctatca tttaatctga gtcctaaaaa ctgttatact taacagttaa     660
cgcatgattt gatggaggag ccatagatgc aattcaatca aactgaaatt tctgcaagaa     720
tctcaaacac ggagatctca aagtttgaaa gaaaattat ttcttcgact caaacaaac      780 ttacgaaatt taggtagaac ttatatacat tatattgtaa ttttttgtaa caaaatgttt     840
ttattattat tatagaattt tactggttaa attaaaaatg aatagaaaag gtgaattaag     900
aggagagagg aggtaaacat tttcttctat tttttcatat tttcaggata aattattgta     960
aaagtttaca agatttccat ttgactagtg taaatgagga atattctcta gtaagatcat    1020
tatttcatct acttcttttta tcttctacca gtagaggaat aaacaatatt tagctccttt   1080
gtaaatacaa attaattttc cttcttgaca tcattcaatt ttaatttac gtataaaata    1140 aaagatcata cctattagaa cgattaagga gaaatacaat tcgaatgaga aggatgtgcc    1200
gtttgttata ataaacagcc acacgacgta aacgtaaaat gaccacatga tgggccaata    1260
```

```
gacatggacc gactactaat aatagtaagt tacattttag gatggaataa atatcatacc    1320
gacatcagtt ttgaaagaaa agggaaaaaa agaaaaaata aataaaagat atactaccga    1380
catgagttcc aaaaagcaaa aaaaaagatc aagccgacac agacacgcgt agagagcaaa    1440
atgactttga cgtcacacca cgaaaacaga cgcttcatac gtgtcccttt atctctctca    1500
gtctctctat                                                          1510

<210> SEQ ID NO 39
<211> LENGTH: 1407
<212> TYPE: DNA
<213> ORGANISM: Arabidopsis thaliana
<220> FEATURE:
<223> OTHER INFORMATION: SEQ ID NO: 39 Contains promoter fragment from
      prAT1G13300

<400> SEQUENCE: 39
ttttgggcga caggaaagaa acttaattaa gtattaggtc aattttagaa aatactaaac      60
tatttactga ttgtgaaagg cattggcacg ccattatcta taaagttgg aatgatgcat     120 gaggatcttt gataatacag tccaacacgt tatgttttc atgttttact tggcaatacg     180
aataatacaa ctaattaata ttaccggcca aaattcaaag atattgacac atgtaagata     240
gatacaatta cacacactta agtaataatt atagacggat acggataatt gaatagaact     300
aatttaacaa agtcaagatt ctgtgacatt acattttgtt tttaaaaata tttgaatcct     360
aatggataaa gggctaaaaa cttcaatgaa ggtgttatta gtagtgcccc ttttttttgt     420
ttcttctccc ttcgcttgtt ttggcttctt cagtaagaga catttggctt ttgagtttaa     480
cgtcatttgg tagtgatcac ttttccttta acgaaattaa gatgagaaaa ctgcaaatta     540
agtacagtat taattaacta agatatactg tatattatag gttactgcat gctacacttt     600
tcttttcggg ggcttgttta aactaggatt gtgctacaaa ccagatattt tattttaaaa     660
ttaaacatta aaatatcatt tatttacagt aaaatatatc tcattataga atggatgaag     720
tataatagca tatggtaaga aaaaaaaaac ctcaacggtg gatatgttta ttctctctat     780
ctcctttaca aaacttcttc tagttttgtat atattgtaaa aggttgtctg catttacata     840
aggcaatatc cacgcggatc ggagattaaa gaatacttca gtcgcttatg taacacaaag     900
ttaatgtaat gaagttcata actcatcagt caccagtcac aagttaaatt gattagattc     960
tagaccaata agtatccatc tccttttct ttttggtcgt ctaataagta tccagttctt    1020
tgcattttga caaattaat ttattaccta attaacaaag aatcacattg cggaatattc    1080
accactcacc atctactact agctagctag ccacaacaag acataaaatc aaattggttt    1140
tataaacata taaaaaaata aacgcatgat tcgtcttgta acgcgacggg ccgacttatg    1200 cattttaat cactcaaaat actgatccta gaggccttat atatatatat atatatatat     1260
atatatatat atatatatat atatatatat atatatatat atatagagag agagcctgat    1320
atatatgtat tgatccctct ctctaaagca aaaaacaaa tctcaaaata aaaggtgga     1380 ttaaaattaa gtccctaaag tatcatc                                      1407

<210> SEQ ID NO 40
<211> LENGTH: 1401
<212> TYPE: DNA
<213> ORGANISM: Arabidopsis thaliana
<220> FEATURE:
<223> OTHER INFORMATION: SEQ ID NO: 40 Contains promoter fragment from
      prAT2G48080

<400> SEQUENCE: 40
```

```
taaatggaga agtcccttc cgacgatcaa gagtcaagtt tgactccagc agatgcataa      60
tatgcacaat agacaaaatc gatcgtatat ttaaattaaa aacaaaaatg aatacgacga     120
atctcatgat tggcccttat gcaatttaaa ttcaaattaa gtaataaaac tacattcata    180
tgtcaactaa atctgacgtt accaaactgg tttgaaaagg aagaaaaaaa ctcgaggacg    240
cctagtgttt agactatttt acaatttagc aaacgcagac aaattaatgt tttgtttcct    300
acattttatt atgagcaatc gggaataatt tggtttgata aatcaagtag tcgacatggt    360
gtaagcgagg cactggacgg tggcacgata ggtgagtcat gatgactcaa gaaggcctca    420
cgttactcac agtggctgga tcattttatt atataattac tctctgagtt gtataaatcc    480
taatctataa ttaacaaatg tatagtctat atataatttg tctgttcgtt cactcagtat    540
ctatcgtcaa tgcccttaca aaggcaggc acaaaaatta cgaacaaatc aatgaccct     600 cagtgacaga gagaccaatc aaaatcgctt tatttattta tctggtgaac tcattgtgct    660
cttcatacat aaaaaaaaga gttttatata ttgagaaaag aaaagtttac tacctacacg    720
tggaaaacgt agagggaagt cgactttatg gatgattaga aaaggtgta gaaaaattgc    780 aacaggtctt gaatctttct ttaattgagt aaaaaaaacg taggaaaatg ttttggaacc    840
gtgaaaatta cgaaagagag agaggcagtc atattatagc agattaggag acaataataa    900
agatatatag agagaggcaa ggccagttat ggtagataat tagttccaaa ccatgcatct    960
ctgtaaccat ggatggatgg atggatgata cgaacgaaaa cggcctagta gagaaaagaa   1020
agagattttt gtcttttccg gcaagcgaga ggactcttct cctgagggc aatgtgggaa   1080 gaagaaagct aaatgatatg gccacaacag actcgatcga aggacttgtt ctcctcactt   1140
tcctccaact taattttatt ttttaagtt atggtttagt caataattac gatggagtcg    1200
agtcgagttg agtttgtccc tccccccccc ctacctatat ttaaacatca tccatgccta   1260
gagcttttta cttgtattat taattttgtg gctaaaccaa aaccaaagaa acatttatta   1320
ttacaaattt tagtatccaa caaagcattc aagcccttaa accccccaaa acctcctccg   1380
atcccattct ttcgttaact g                                              1401
```

<210> SEQ ID NO 41
<211> LENGTH: 1409
<212> TYPE: DNA
<213> ORGANISM: Arabidopsis thaliana
<220> FEATURE:
<223> OTHER INFORMATION: SEQ ID NO: 41 Contains promoter fragment from
      prAT3G25790

<400> SEQUENCE: 41

```
actgaatatg gccttttgag actccgaggg gacaattata atccaacact aaaatacatc      60
tctaaactct atttgccaac taatttcttt atttaaaata cgtttcaatc taatcaaaac    120
agataagcct gttaaacaca attttgattt ctcgagacta cgaataggtg gatctatttg    180
tatcataaca tcataacata taaatcgata tttaaaattt tgagtaataa atttgatgtt    240
ggtctctaac aatttgcggg taatttcttg atattttgga catcacccga acatattagc    300
tcattacaca ccaatttcta tagaggcaac atattttctt atcattaaag ttgacagcta    360
ttagagccct taatcacgtt tgatttcata tctaattcca aattatatgg ataacaac     420 agcatagcat ataaattgat atgtgtagca ttaggttata tctttgaccg ggaaatgcat    480
tggcaggcca ttatactggg aagatgcatt cgcatatata ttagtaggtg tacttagtaa    540
tcgtctactt gacataatta aaattaccgg tcaaaaacac gagatatata ggaactcata    600
```

```
ttgtgtggat atatatatta gtttacatgt gtatttatgg ataaggttat aacgaattca    660
acaaattctc aaggtcctat gaaatttcaa caagtatatt acagttttt tttatatat      720 ggcttttctt ctcccatgtt tcggctgtct acgaagagac atttggcttt tcatattggg    780
atattgaaaa atacattttc aacgttttat atatgatttt gtgtgggtga aattaatact   840
tacagaacaa aagagctcat gcacgtttag tgttattttg gcggctgttt ttaaggattt    900
gcatatattc tttcccacgt attgaattct ataaatgaca taataatcaa acttgtaaaa   960
ataatagaat gaatagttta tagtcttcca aaattcgatt tctgttgtag tggaatcgca   1020
gacattttct aacttatgaa tgttgttata ggacttcttt aaaccttggt tggatatacc   1080
caaataaata taaagttcac acgaaaaaaa cttggaatca catccaggaa tattcaccac   1140
tggatcaata ctactataca acaagggaaa aaaaatatt taacttggga aggtatatac    1200 ttatttata aacaaaagca agattcgcct tgtaatgcga cggcccgact tctctcttc    1260 aaataatgat ccttgagaaa ccctatagag ccatatatac gttgtcttta taagagaca    1320 taactcatct cttcttgact aactttatag ttaaagttat caattattcg aaaacaaagc   1380
tggttttttg ttttgtccct taaaccagc                                       1409

<210> SEQ ID NO 42
<211> LENGTH: 1401
<212> TYPE: DNA
<213> ORGANISM: Arabidopsis thaliana
<220> FEATURE:
<223> OTHER INFORMATION: SEQ ID NO: 42 Contains promoter fragment from
      prAT5G10210

<400> SEQUENCE: 42
gtgggtctta gcttattgga ttgcgatatt gtaaagtaaa agttttgaaa aatggaagat    60
ctgcatttag tccaccgagg atcatatgca tagtcgatat tgacacaaga gtgaaatttg   120
attggaggaa agaggatatg taccaagcca ctatttacct ttttttttacg tcaggctctt    180 gagatgatct tcttagtttt gatgtctttt tgcaaattgc agtgacgttt tctaaattgg    240
tacactaagt ttaaaaatgc tgtcctttgg ataactccaa cggatgatat gaactaaaac    300
aatgctgtcc tttcatatta tgtaagaaaa cactcactcg gttaactatg agcaacccac    360
tacaagtaag tattgtaaaa acgttttttt ctttcaaatt ccaagtattt tttaaatttt    420
gtaatagaaa ataatgattt gggttttgta agttagtatt aggatttaga tttttttaaa    480
tagtaacgaa agtgtttgat aaaaaagtaa atagtaacga aagtaaccta aattgacatt    540
tccattaccc ttgagatgat caaaataaac acaatttctg catgattatg agtttatgac    600
tatgcttatt agcaatgatt tgttctttct ataatttaaa accagttgaa actaaaattg    660
tttttgtaaa atttaataga tgatattatt agtatacaaa acttttgtca acaatgaatt   720
gtgtgataag agttttttg gagattttct tatgtaataa agtctatctt gtatgactac    780
aattgatcat gggattcgtg gctaatattt tttgtaatta tatcttttga gtcaaattcc    840
atactcattt taatatatgc aatcgaatgt atctactaat aatttgttct tatttaattt   900
gattctgttg actctgttcc aaaacaactt tcggctattg gatgtgtcca cgcgaaatgt   960
aatataataa tgatcaagtc ttcaaaatgg cacaccttaa tttcttttttg caaattataa   1020 aaattcttta tatggtgatc ctacgtatct atctaattat ctcccaaaac tatgggcaag   1080
agtcattatt aaaatcgacc cttggtcttt tgagatgctc aagagtttta atttctaaaa   1140
tattaagcct tcactaacat gattagaaaa aaataaaaag ttaaaaacat gattagaaat    1200
```

```
ttagaatatt ttaataagta caatgtggaa atctagtgta aactttcctc gaacattccc    1260
catagattta tataaatagc tagtgagaat ttgttcatgc acatattcat cacaaaggaa    1320
ctcactgctc ttaaatttgc tctaattgtt attaccttgg taaataatat attcttggtt    1380
cgattcgaaa ttttcaagca a                                              1401
```

<210> SEQ ID NO 43
<211> LENGTH: 1208
<212> TYPE: DNA
<213> ORGANISM: Arabidopsis thaliana
<220> FEATURE:
<223> OTHER INFORMATION: SEQ ID NO: 43 Contains promoter fragment from prAT5G19970

<400> SEQUENCE: 43

```
accaaacaat caccatacaa agtgtggaag taaagtctca aagctttgtt agagaagaag     60
tcctagatag tacttggcta tagttaaaat attttagtag atgaagttga caaattaact    120 atttctttt gtaatgtttg ctttgttctt tactaatata aagatacttg gctacagtga    180
aaatgttata aaaagagaga aaagaataga cagttaaatt attaaggttg acacaaccat    240
catctccacc gtccattact cgtcagccga atgttttta tttgattaag atgtgaacat    300
catccattga cctatcgttg cttgtaaagc caagttagcc aaccaacact caaatcatca    360
ttatacgtga cgatcttaag aacaacccca tttaggatac tctatatgtt tgtcttctca    420
tataaatttc attatagtaa tattaaggca ttatccatta ttcatatata ttcttcaagg    480
catgtttcgt acatcttata gcaaaccagt agcagtaaat agcataagca aatgtgttct    540
tcttgtcgca tggctctagt ggaattccac gtttctcctt cttctcttgg taagccgtat    600
tgtcaaatcg acgtggatat atatatgaat attttagttg ttttgacaaa gatgattatt    660
gaaagagtaa ttaggtcact tcagtaaggg aaaatgttaa agttttagga gtcataaagt    720
ttatgtgcta caataaggta attatacttc gtataaatag tagaagaaaa aaactggtat    780
atcaaaactt catttagtca aaataggcat gtgcatgatg caagtgattt agtaggtcat    840
gttcatgccc atatctactt tactgtattt tccctaaaac ctcaagtaaa aaaactggta    900
tatcaaaact tcatttagtc aaaatgtaat taacttttct ttgacctaac aagtgaactt    960
aaaaggttat tatattccca ccacaaattt atattttgtt agatagctag ctcttcttct   1020
atatatataa cctacaacat tgaagttgat cctatcaact caaaaacacc actccaaaaa   1080
aatactaaga aatggaaaaa agccaaagat gtaacaaaga cacaaacacc accattggct   1140
tttgccttct tccttctgaa ctcatacaaa acattctatt ccatctttgt atacctgaga   1200
tcatccga                                                            1208
```

<210> SEQ ID NO 44
<211> LENGTH: 570
<212> TYPE: DNA
<213> ORGANISM: Arabidopsis thaliana
<220> FEATURE:
<223> OTHER INFORMATION: SEQ ID NO: 44 Contains promoter fragment from prAT1G15125

<400> SEQUENCE: 44

```
tttgcgctta ctacattttt ttgctacttg agtaattgca tggcctaata acaagatatg     60
ttgtgccttt ctttggtcca attgtcgtag acaatgcgtc aacaaatcat taggcttgaa    120
gtttcaataa gagagatttt caagcctctg ctattaggtg gcctggtact atggccattg    180
```

```
attaggattt cttagagctt gccaagttta tgatcggact aactctgaag cttattggtc        240
ttaaagataa ctatctaatg atggcggcta caagaagata tttttctttta aattttgaag       300 gtgaagaagg ttgaatagtc ttatggtgaa atcacatgtg actggaatga agtgaagaac        360
tgtttagtgg agtgtgtgat gcatgcagca gccacttttg aaggacagct tggactttag        420
agtgagagtg agatgtatgg cccgcggcgg ctgcattaga ctgaatctta tccttgacac        480
tctacagcaa ttatgtagat ctcccatttt gaccctctat ttaagggtta gcaagtgtaa        540
taccagtcca tacaatacca ttacatagcc                                         570
```

<210> SEQ ID NO 45  
<211> LENGTH: 1424  
<212> TYPE: DNA  
<213> ORGANISM: Arabidopsis thaliana  
<220> FEATURE:  
<223> OTHER INFORMATION: SEQ ID NO: 45 Contains promoter fragment from prAT2G38940 (prAtPT2)

<400> SEQUENCE: 45

```
taaacgaagc aaaaaagttg gtaaataagg aagagaaaac ctacaagata ttaaaacggt        60
gtcgttgttc ggaagaatat accgaagtag caaaaggaat atctcattag agagtccctt       120
ataaatgacc gttttaatac acttcaactc tgtccttgtt cataggcagc ttcaacgatc       180
attccacttc cttcttcctc tctctcaaca ttttcccctg aaaataagga aactaaagat       240
tcttcctctc tctttctaca ctcttctgac aatactaaaa cactttatca gatcagatcc       300
cacataaact ttctgtaagt gtttctttta aactatgtct gttgatgtta atgtttatgg       360
atgcataatg attttagtta ggacgttatc gttttttgttt tgttaggtgg tcctctctcc       420
ctgttcaatc tctaattcgt catgtcttat tcgtttcttt cattggaaaa aaaacactga       480
aaactagttt ttgtttttcc aactttcttg gatcattaaa taggattgct ctctcttcaa       540 acgtatttt gttggatctc tcctcttcag ttctagaaga cttttttttt tttccttttg       600
ttgagtgcat gatttcaaaa aatttcaatt gaagaagttt gtgatatttt gttgttttct       660
ttcttcaata gaggtgtgt ccgcaattaa gacaaaacaa ctcgctgtca tactcagtta       720
aagtctttgt tgctcgtgtt cagattttca ctagacgtca caagtcaact tttgtgggta       780
actgaagaca aatagtaatc gttgaaaact acaataataa aataagtact tccagtgtct       840
ccgttcacct ttaaaaagtc gagataaacc caaaaaaata ggaataaaca atcttttgtc       900
atatccgtta ataagttta acaaatcttt acaaattaat aagaagaacg tatataataa       960
atatttcaaa attaacgagt gtggactaat attgagttga cttttattat cacttcattt      1020
cagttccttg aatatgcata tactgtatat ggtttctctt gcaataagta agcatcatac      1080
atatgtacag gaacatgaga agttgtcgtt aacaactact tcatctaaaa aacatacaca      1140
tgttattttt ctaatattgc ctgacttcaa gttcggtgaa catactttat tgggttgtaa      1200
ttgtgagatc aatgaaatga gaaaaattaa atagaacttt tatgatattt taatgttaat      1260
tgatactata taaagcaggg tctaattcta tttgctttta aaactgccta acttatttca      1320
agttcggtat aactaactac tttattgttt gtaatgagtt atttaagggt acttatatgt      1380
cgaacttttt tttgtgtgat gaaaaattgc agaggagaag aaga                       1424
```

<210> SEQ ID NO 46  
<211> LENGTH: 1393  
<212> TYPE: DNA  
<213> ORGANISM: Arabidopsis thaliana  
<220> FEATURE:

<223> OTHER INFORMATION: SEQ ID NO: 46 Contains promoter fragment from
      prAT5G44420 (prPDF1.2)

<400> SEQUENCE: 46

| | | | | | |
|---|---|---|---|---|---|
| cgacgttgga | ctgtttcatc | atatcccata | aaatacatg | attggggtga | aaatcttgaa | 60 |
| catattaaaa | aaatattaaa | tcaaaatgat | aaagataggg | atttataaat | gtaaaacggg | 120 |
| cgtgtcgaga | attttatgga | cattgggaca | agctttatat | gcagcatgca | tcgccgcatc | 180 |
| gatatcccga | ggtgcatcgt | ttctactttc | atgtccaaat | ttggggttaa | ctcacaatat | 240 |
| atatcatgtt | gcctatgtaa | atttataatc | ataaatctaa | acccaaattt | taatcctcat | 300 |
| tccaaagcaa | aagttctaag | ccctacaaaa | atatgtattt | cccaagttta | aaagaatta | 360 |
| atctatactt | ttacaaattt | aaattctgat | ctcttataat | gttcggtttt | tccttttta | 420 |
| tttattaagt | tagttaaaat | ttgcagttat | tttgttgaat | gtcgttgttt | acgaatttac | 480 |
| gaataatacc | tttatagcta | atctacaaaa | ttttgatgac | tgacaacacc | gttaatgttt | 540 |
| tttttaaat | taccctgagc | ctctcacttg | cggtcagacc | atgcatgtcg | atagtccatt | 600 |
| acgtttaagg | ccacaatcaa | ctatagtttg | tttatcaata | gccaactaag | ctaacttta | 660 |
| ggttcctgcc | ctctccgttc | ctccggtacc | aatcgtttct | ttgtcccttc | gatagtttga | 720 |
| aaacctaccg | acggtgagag | caaaatattg | atgaatcatc | caatttcag | taataggtgt | 780 |
| gtcccaggga | tatataaatg | gcgaaactac | gcgagaacgg | ttccttgttc | tgcaaacttg | 840 |
| gcggaacaat | gctgctcttg | agatcaacca | aaccatatgt | ttagtccaca | acgatctata | 900 |
| tgtctagggg | tgatcctcta | atcgaaaaat | gttgtatttg | ttcgacgatg | acgaaggtca | 960 |
| gactatgaac | tgcacagtct | gcacttgtcc | taaccgcgag | aatctctgac | atcaatatac | 1020 |
| ttgtgtaact | atggcttggt | taagatatta | ttttcttgag | tcttaatcca | ttcagattaa | 1080 |
| ccagccgccc | atgtgaacga | tgtagcatta | gctaaaagcc | gaagcagccg | cttaggttac | 1140 |
| tttagatatc | gacagagaaa | tatatgtggt | ggagaaacca | gccatcaaca | aacaaaaagc | 1200 |
| aagatcttat | cttttgatat | tggctacggg | aagatgatgt | ctgtttaatg | tgtggggtta | 1260 |
| ccacgttatt | gtacgatgca | caagtagaag | attaacccac | taccatttca | ttataaatag | 1320 |
| acgttgatct | ttggcttatt | tcttcacaca | acacatacat | ctatacattg | aaaacaaaat | 1380 |
| agtaataatc | atc | | | | | 1393 |

<210> SEQ ID NO 47
<211> LENGTH: 1441
<212> TYPE: DNA
<213> ORGANISM: Arabidopsis thaliana
<220> FEATURE:
<223> OTHER INFORMATION: SEQ ID NO: 47 Contains promoter fragment from
      prAT5G24770 (prVSP2)

<400> SEQUENCE: 47

| | | | | | |
|---|---|---|---|---|---|
| acgattttgt | gaatgatggt | agaaaaatat | aaagatgaga | attatcaatg | ttttcgacgg | 60 |
| gttttcgacg | gacgtccgac | gggttttggc | gacgaatttc | cgacggaaat | tttgaatatt | 120 |
| tatttttaa | aataaaaaaa | tgcacggcta | tgtgaccgtg | cggcgaattg | accgagtagc | 180 |
| tacttgaccg | agtgtatttc | gttggaattc | cgtcggaaaa | gtgcagaata | ttctgatgaa | 240 |
| tattctaggg | atcaaaacgg | atatattttg | gtcggaaatc | cgtcgaaaca | tttggtcgga | 300 |
| tttaatttgg | tcggatttaa | tttggtcgga | gtttcgttgg | aaatgactga | tgaattgtcg | 360 |
| atcatttaga | attcgtcaga | aaagttcgac | gacatttgac | cggaaaacat | gtcgtcagaa | 420 |
| aaccgtcgga | ataccattac | gaaccgtcg | aaaattttcg | accgtttatt | tatcgtcgaa | 480 |

```
aagtctgtcg aaaagggttt tgttctcttg tagtgtacca caacttggtt tgcaacacta      540
tatatacttt ttgatatata aaaattctat taaactactt aaatatttcg tcatgaggtt      600
atatgcatta gaaaaaaata tataacaata ttgttggaag actggacaat tatcgttgaa      660
actatagcta tcaccaagat acaactttt gtggaaaatc ttggtggcaa ttagaaactg       720
ttcccaatct cgggcatgaa atcgttatt caaatatttg tcaacaacta gtgaatagtg       780
atacagctat atatgtttgc taatttattg aattatttaa tgttacgact ttacgtaaca      840
attatttaac gtctattctt gtgtacctca catttcttat cgtcatgtct catctcttat      900
attattcaca gtcacccat ctcttctcgc tcactgtgga acctgttgtc aattactcgt       960
tttgcatttt attggttttc ccaattactc tatcaattat ttatcaaaaa aaaaaaaatg     1020 aaacattac tctatatatt atttccgcaa acacaaatta tactcacatc aacatattca      1080
atacattttt ctagtaatgt agaacaactt tacagtattc tccaaaacga aactctaatt     1140
caaaatttac aagcagataa gccaaagata atagaacaac aaaacgccaa attctagtta     1200
agcacacaat ctcaacgtgc actaaaaacg agtggtgtaa gtgaaaaata tcgtcgatta     1260
taaacattat gggaccagta gcatttgttg caccaatcga aaacagacaa gcacacatat     1320
ctcctcattt ctcatctggc ttcttaatca tttctcataa ccccacctca ttataaatac     1380
caccctttgc gtcacacata taaacatcac aaactaaaca ataaaccata ccataaaaaa     1440
c                                                                    1441

<210> SEQ ID NO 48
<211> LENGTH: 1207
<212> TYPE: DNA
<213> ORGANISM: Arabidopsis thaliana
<220> FEATURE:
<223> OTHER INFORMATION: SEQ ID NO: 48 Contains promoter fragment from
      prAT1G71520 (prTARGET)

<400> SEQUENCE: 48
ccatgtaata gtatatagag atggctttgc tctgtctttc tttgtgttta cccccttatac     60 gagatattct ttcttctcct tgagttcaaa ttataatctt caagctttcc cactatcttt    120
tgtatttgac atacaacacc tcatatttga ttgggtgaaa caaaaacgag agaaaatttc    180
aataaccatg ctaggccact tggactatat agtcttcatt tctattcatt tctattcatt    240
ttatgatttt tgttcaatta gcaatatagg catacataat ctttttttta ataaataaat    300
taactctaag aatttggaaa atattattaa gtttatgaga taatgtatgt taaatgtaaa    360
aataacatat aatataaacc tcttaaccat aatttttta ttaaaagaag aaagggaggt     420
cattgtagag actagagagt acattgcatt caaatttggt tgctcaaaag tgagtgattc    480
cgtgtgcgga atcttagttt gtgttaaatt tgagtaccac caatcaaaga agagaccaca    540
aatctcatat cccttttcgt tttcagtgtg caaattgcaa aacgagacaa gacaaaaaat    600
aacttttctg cccttttagtc aaactataa gcccaagaag agcacccgtt taagactatt     660
tgaagacgtc atgcctgatg aaattaacca aacaaaataa gagagagagg caagtctcat    720
gttttctttt caagtttcag cacgtgatgt cgtgatggac tgttgtgtac ttgtgtgttt    780
tttaattttc ttttctatca gacttttga atcaagtcgt attgatgata tggatcatca     840
ggtgatatga tgactctcat tacgttggaa aattcatttg tttatccaaa tgggtattta    900
gttgatgtaa acctcaacaa gttgaaactt gaaacacgac tcgaatattc caaagaaccc    960
aaaagctaaa actaaaatag aaaacgtcaa ccagtgcgag ccacatgtcc atatctcata   1020
```

```
accccccccgg tcatactttg accatatatt atttgtttat tcatctcata acccaatttt    1080
aaaagtacaa tttatataca ttcaatttat tcggacttga tctacacgac tttattccgc    1140
ttcaacgtat ttatatgcaa cattttccct catgatctta taatctcatc ttcatccacc    1200
caaaaac                                                              1207
```

REPORTER CONSTRUCTS FOR COMPOUND SCREENING

CROSS-REFERENCE TO RELATED APPLICATIONS

This application is a continuation-in-part application of U.S. application Ser. No. 13/699,527, filed on Apr. 15, 2013 (granted as U.S. Pat. No. 9,322,070 on Apr. 26, 2016), which is a United States National Stage Application that claims priority to International Application No. PCT/US2011/037573 filed on May 23, 2011 (expired), which claims the benefit of U.S. provisional patent application No. 61/347,516, filed on May 24, 2010. PCT application PCT/US2011/037573 is a continuation of PCT application PCT/US2010/045941, filed on Aug. 18, 2010 (expired). This application is also a continuation-in-part application of U.S. application Ser. No. 15/084,800, filed Mar. 30, 2016 (pending), which is a divisional application of U.S. application Ser. No. 13/699,527, filed on Apr. 15, 2013 (granted as U.S. Pat. No. 9,322,070 on Apr. 26, 2016), which is a United States National Stage Application that claims priority to International Application No. PCT/US2011/037573 filed on May 23, 2011 (expired), which claims the benefit of U.S. provisional patent application No. 61/347,516, filed on May 24, 2010 (expired). PCT application PCT/US2011/037573 is a continuation of PCT application PCT/US2010/045941, filed on Aug. 18, 2010 (expired). The entire contents of each of these applications are hereby incorporated by reference.

FIELD OF THE INVENTION

The present invention relates to reporter constructs, transgenic cells and transgenic organisms that can be used for the identification of agents that regulate gene expression.

BACKGROUND OF THE INVENTION

Manipulation of organisms or in vitro cultures to alter and/or improve phenotypic characteristic often requires the modulation of gene expression. For example, the stress tolerance of a plant can be improved through modifying the expression of genes involved in signal transduction pathways related to various stress responses. One way to achieve this goal is to genetically engineer the organisms or in vitro cultures, an approach that is costly and time consuming. An alternative approach is to identify chemical compounds that can be applied to these organisms, e.g., plants, mammals, yeast, Drosophila, C. elegans, or bacteria etc., or their in vitro cultures to obtain the desired phenotypes. Currently, chemicals are screened through reporter constructs in which a reporter polynucleotide is directly fused to a promoter sequence that is capable of being recognized by a transcriptional regulatory protein, i.e., proteins that can regulate the signaling pathways that contribute to the development of a desired trait. However, this conventional approach has limited sensitivity that leads to inefficient compound screening and/or requires significant effort to identify reporter cell lines or organisms suitable for the screen, i.e., reporter cell lines or organisms in which the function or expression of the transcriptional regulatory protein can be altered directly or indirectly in response to a compound treatment so that the amount of the resulting reporter molecule is readily discernible from the controls.

The present specification provides, inter alia, novel vectors, cell lines, and methods useful for modulating gene expression, identifying and analyzing regulatory sequences, and discovering new targets and reagents for improving plant performance or therapeutic intervention in human disease. The reporter constructs of the specification contain arrangements of additional genetic elements that can optimize the signal-to-noise ratio of the conventional promoter-reporter assay, minimize the efforts on characterization and development of reporter lines, and thus improve the sensitivity and the efficiency of the screens. These novel constructs and methods can also be used in a high-throughput format to identify agents that can be rapidly deployed induce modified gene expression and/or desired phenotypic alterations in organisms, for example, compounds can be applied to plants through a spray or via irrigation.

Examples of how to employ these reporter constructs and transgenic cells and organisms to identify useful chemical compounds are provided. Other aspects and embodiments of the specification are described below or can be derived from the teachings of this disclosure as a whole.

SUMMARY OF THE INVENTION

The present description provides a novel series of constructs, transgenic cells, transgenic organisms and methods which permit the identification of novel sequences and agents that are capable of modulating gene expression.

In one aspect, the present description provides a transcriptional fusion reporter system where a reporter gene construct comprises, in operable linkage, a target promoter sequence that can be recognized by a transcription regulatory protein, a polynucleotide sequence that encodes a DNA sequence-specific transactivator, and a reporter gene. The reporter gene expression is regulated by both the target promoter and the DNA sequence-specific transactivator.

In another aspect, the instant description provides a translational fusion reporter system where a reporter gene construct of the invention comprises, in operable linkage, a polynucleotide encoding a DNA sequence-specific transactivator and a polynucleotide encoding a translational fusion of a reporter molecule and a polypeptide of interest. The DNA sequence-specific transactivator regulates the expression of the translational fusion protein.

The DNA sequence-specific transactivator of the reporter gene construct of the invention contains at least a DNA binding domain and a transcription activation domain, for example, LEXA:GAL4, SEQ ID NO: 4 (a translational fusion of the DNA binding domain of LEXA and the activation domain of GAL4), or GAL4:VP16, SEQ ID NO: 28 (a translational fusion of the DNA binding domain of GAL4 and the transcription activator protein VP16).

In some embodiments, the DNA sequence-specific transactivator is a steroid-inducible transactivator, which regulates transcription when bound by a steroid, for example, LEXA:GAL4:GR, SEQ ID NO: 2 (a translational fusion of the DNA binding domain of LEXA, the activation domain of GAL4, and the ligand binding domain of glucocorticoid receptor), or GAL4:VP16:GR, SEQ ID NO: 7 (a translational fusion of the DNA binding domain of GAL4, the transcription activator protein VP16, and the ligand binding domain of glucocorticoid receptor). These transactivators remain in the cytoplasm until they bind dexamethasone, a glucocorticoid receptor agonist. The dexamethasone bound transactivators then translocate into the nucleus and activate the expression of a target protein, e.g. a reporter, a translational fusion of a reporter molecule and a polypeptide of interest, or a transcriptional regulatory polypeptide that regulates the expression thereof.

In some embodiments, the reporter gene construct comprises a dual-two component reporter system where a steroid-inducible DNA sequence specific transactivator, such as GAL4:VP16:GR (SEQ ID NO: 7), binds a steroid, for example, dexamethasone, and activates the expression of a transcriptional regulatory polypeptide that recognizes a target promoter sequence operably linked to a polynucleotide that encodes an additional DNA sequence-specific transcriptional activator, for example, LEXA:GAL4 (SEQ ID NO: 4). A reporter molecule or a fusion protein of a reporter molecule and a polypeptide of interest would be expressed from a promoter that can be recognized by said DNA sequence-specific transcriptional activator, for example, the opLexA promoter (SEQ ID NO: 5).

The reporter molecule of the instant description can be any reporter gene molecule, for example, reporter gene molecules or reporter polynucleotide whose expression or activity can be measured by calorimetric, fluorescent or luminescence signals, such as green fluorescent protein (GFP), luciferase (LUC), chloramphenicol transferase (CAT), and glucuronidase (GUS).

In another aspect, the instant description provides transgenic organisms or cells derived therefrom, such as microbes, mammals, yeast, *Drosophila, C. elegans*, which are transformed with the reporter gene constructs as described above.

In yet another aspect, the instant description provides methods of identifying chemical compounds comprising the steps of contacting at least one test compound with a cell that was transformed with any one of the reporter gene constructs as described above, and selecting a compound that alters the reporter gene activity relative to controls.

The instant description also provides compounds identified in accordance with the methods.

The instant description also provides methods to enhance plant performance and/or plant yield by applying the identified compound to plants.

BRIEF DESCRIPTION OF THE SEQUENCE LISTING AND DRAWINGS

The Sequence Listing provides exemplary polynucleotide and polypeptide sequences of the instant description.

INCORPORATION OF THE SEQUENCE LISTING

The copy of the Sequence Listing, being submitted electronically with this patent application, provided under 37 CFR § 1.821-1.825, is a read-only memory computer-readable file in ASCII text format. The Sequence Listing is named "MBI-0096PCT_ST25.txt". The electronic file of the Sequence Listing was created on May 23, 2011, and is 76,901 bytes in size measured in MS-WINDOWS. The Sequence Listing is herein incorporated by reference in its entirety.

FIGS. 1-9 depict reporter assay systems that can be introduced into an organism or a cell by transformation. The resulting transgenic organism or cell can be employed to identify useful chemistry that regulates a signaling pathway of interest. Ovals represent the polypeptides, rectangles represent polynucleotides, and hexagons represent one or more chemical compounds. Lines with arrow-heads indicate a direct or indirect chemical enhancement of activity whereas blunt-ended lines indicate a direct or indirect repression of activity by a chemical compound. Filled circles represent dexamethasone. FUSION represents a translational fusion of a polypeptide of interest and a reporter molecule, or its encoding polynucleotide. DBD:AD represents a translational fusion of a DNA binding domain (DBD) and a transcriptional activation domain (AD), or its encoding polynucleotide. DBD site is a promoter sequence which is bound by the DBD. REPORTER is any fluorescent, colorimetric or luminescent reporter, e.g. GFP (SEQ ID NO: 8), GUS (SEQ ID NO: 9), or luciferase (SEQ ID NO: 10), or a polynucleotide that encodes any of the aforementioned reporters. prTARGET (SEQ ID NO: 48) represents a promoter can be recognized by a transcriptional regulatory polypeptide in the instant description. PROMOTER represents any promoter sequence. Roman numerals represent the serial events that may occur associated with the treatment of the chemical compounds. DBD:AD:GR represents a dexamethasone-inducible transactivator that encodes a translational fusion of a DNA-binding domain (DBD), a transcriptional activation domain (AD) and the ligand binding domain of the glucocorticoid receptor. DBD can be any DNA binding domain, for example, the DNA binding domain of GAL4, SEQ ID NO: 18, or the DNA binding domain of LexA, SEQ ID NO: 16: AD represent any transcription activation domain, for example, the activation domain of GAL4, SEQ ID NO: 20; VP16, SEQ ID NO: 22; EDLL, SEQ ID NO: 23-26.

FIG. 1. Transcriptional fusion assay system I: i) transcription and translation of a DNA sequence-specific transcriptional activator DBD:AD:GR; ii) translocation of the DNA sequence-specific transcriptional activator into the nucleus upon addition of dexamethasone, and binding to its cognate promoter sequence DBD site; iii) transcription and translation of the reporter (reporter1); iv) transcription and translational of a transcriptional regulatory polypeptide leads to v) binding of the transcriptional regulatory polypeptide to its target promoter sequence; vi) modulation of the transcriptional regulatory polypeptide binding or activation by a compound through direct or indirect mechanisms; vii) transcription and translation of the reporter (reporter2).

Figure 2:
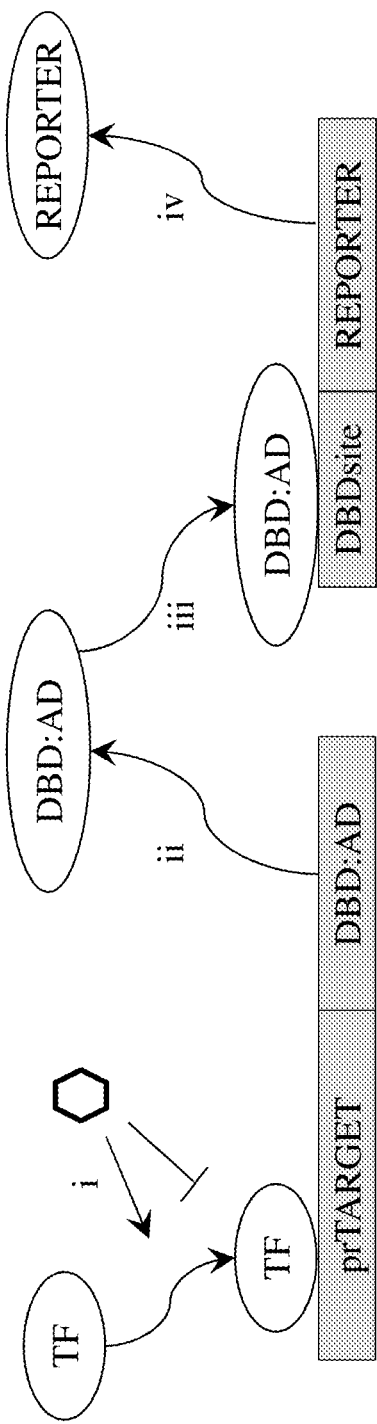

FIG. 2. Transcriptional fusion assay system II: i) compound-mediated induction or repression of DBD:AD transcription under the regulatory control of a promoter recognized by a transcriptional regulatory polypeptide; ii) transcription/translation of DBD:AD; (iii) binding and activating the DBD site promoter; (iv) transcription/translation of the reporter gene.

Figure 3:
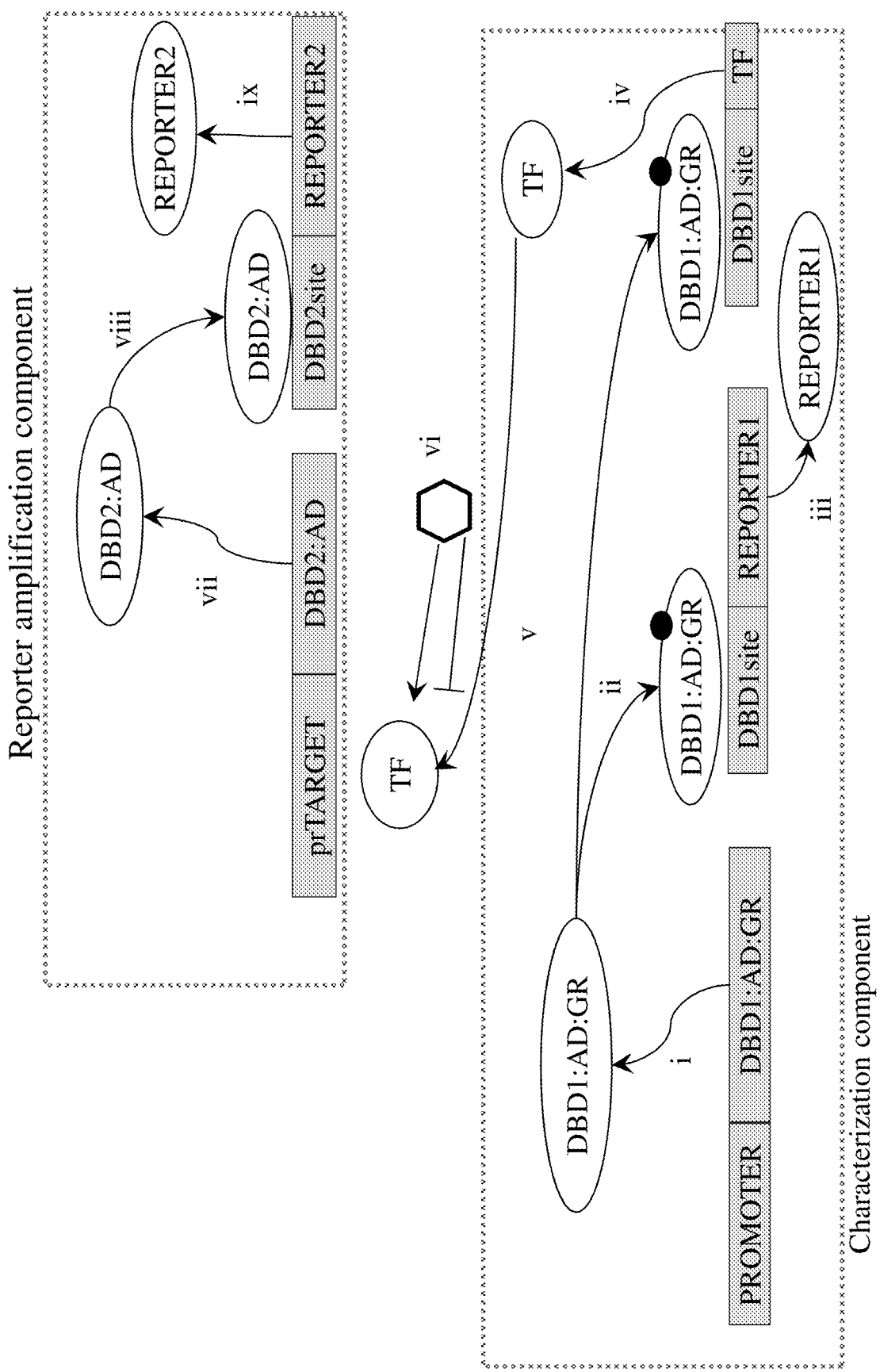

FIG. 3. Transcriptional fusion assay system III: i) transcription and translation of DBD1:AD1:GR; ii) translocation of DBD1:AD1:GR into the nucleus with binding to the DBD1 site upon the addition of dexamethasone; iii) transcription and translation of the reporter (reported); iv) transcription and translational of the target transcriptional regulatory polypeptide, which leads to v) binding of the transcriptional regulatory polypeptide to the target promoter sequence; vi) modulation of transcriptional regulatory polypeptide binding or activation through direct or indirect mechanisms by a chemical compound; vii) transcription/translation of DBD2:AD; viii) binding of DBD2: AD to the DBD2site promoter; ix) transcription and translation of the reporter (reporter2).

Figure 4:
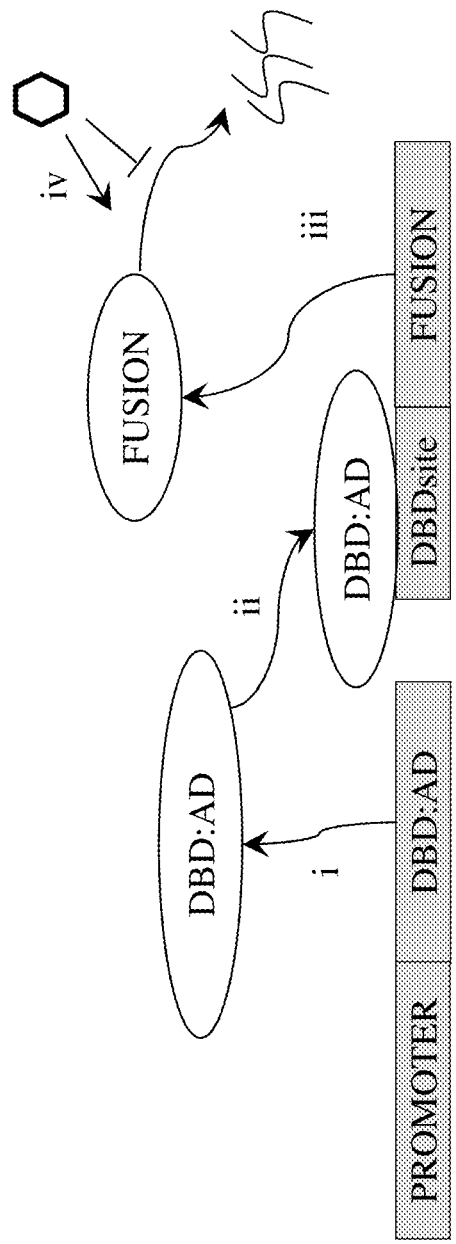

FIG. 4. Translational fusion assay system I.: i) transcription/translation of DBD:AD; ii) binding to and activation of the DBD site promoter; iii) transcription/translation of the fusion protein comprising of a reporter molecule and a polypeptide of interest; iv) stabilization or degradation of the fusion protein upon the treatment of chemical compounds.

Figure 5:
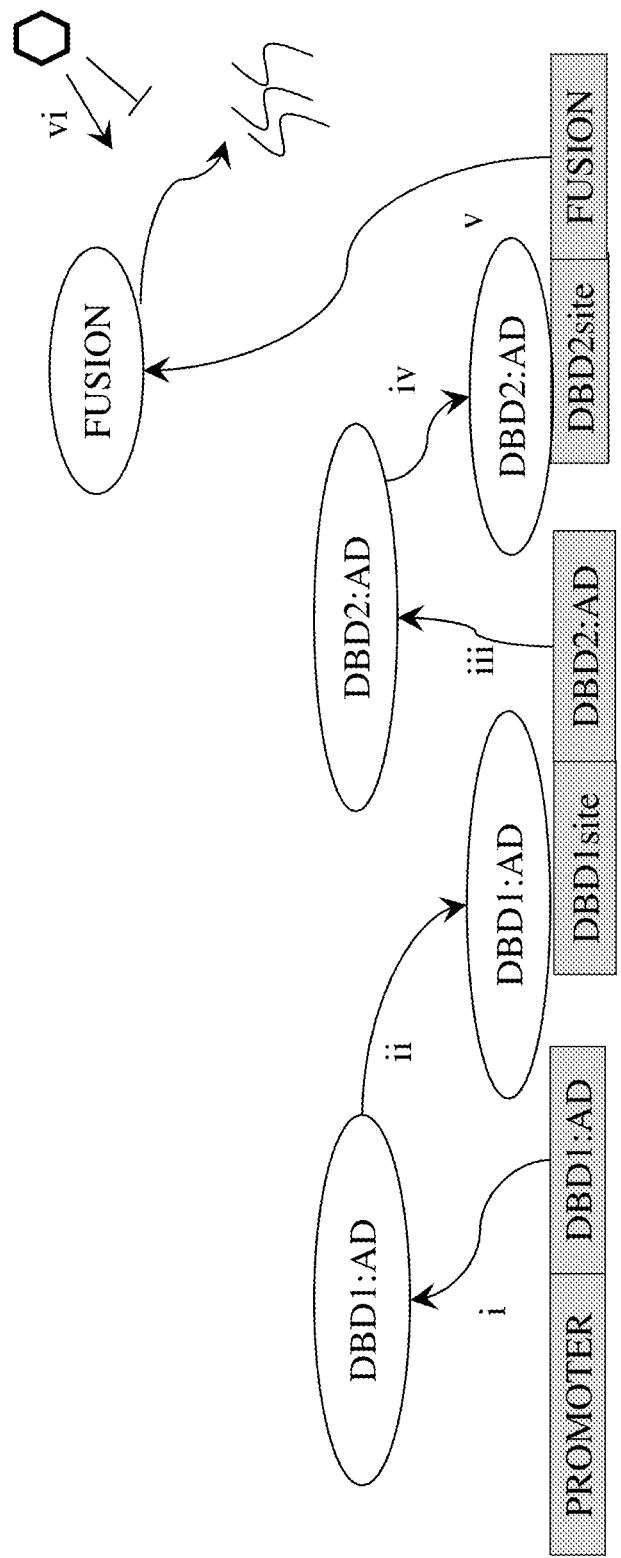

FIG. 5. Translational fusion assay system II. Two rounds of amplification. i) transcription/translation of DBD1:AD;

ii) binding to and activation of the DBD1site promoter; iii) transcription/translation of a second DNA sequence-specific transcriptional activator DBD2:AD; iv) binding and activating the DBD2 site promoter; v) transcription/translation of the fusion protein comprising of a reporter molecule and a polypeptide of interest; vi) stabilization or degradation of the fusion protein upon the treatment of chemical compounds.

Figure 6:
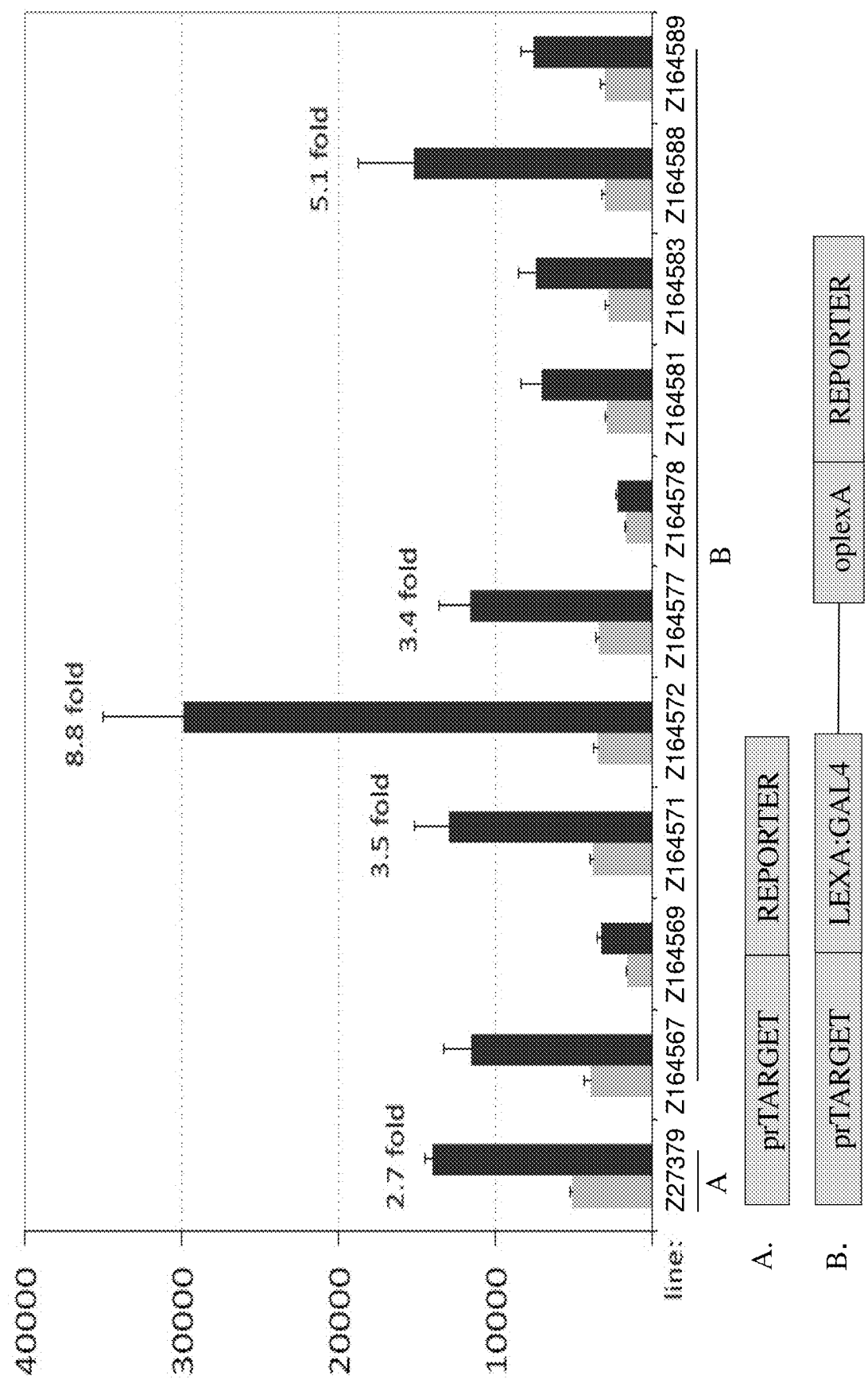

FIG. 6. A two-component transcriptional fusion system of the instant description showed increased signal-to-noise ratio compared to a one-component transcriptional fusion system. Cell lines transformed with A (a direct promoter GFP transcriptional fusion), i.e., "Z27379", and cell lines transformed with B (a two-component transcription fusion reporter system II), i.e., "Z164567", "Z164569", "Z164571", "Z164572". "Z164577", "Z164578", "Z164581", "Z164583", "Z164588", "Z164589", were subjected to an induction treatment, which activates the prTarget promoter (black columns), or a mock treatment (gray columns) before data acquisition. The respective GFP fluorescence values are indicated by the Y axis and the standard errors are shown at the top of the columns. The numbers on top of some columns represent the fold of reporter induction of the induction treatment over the mock treatment.

Figure 7:
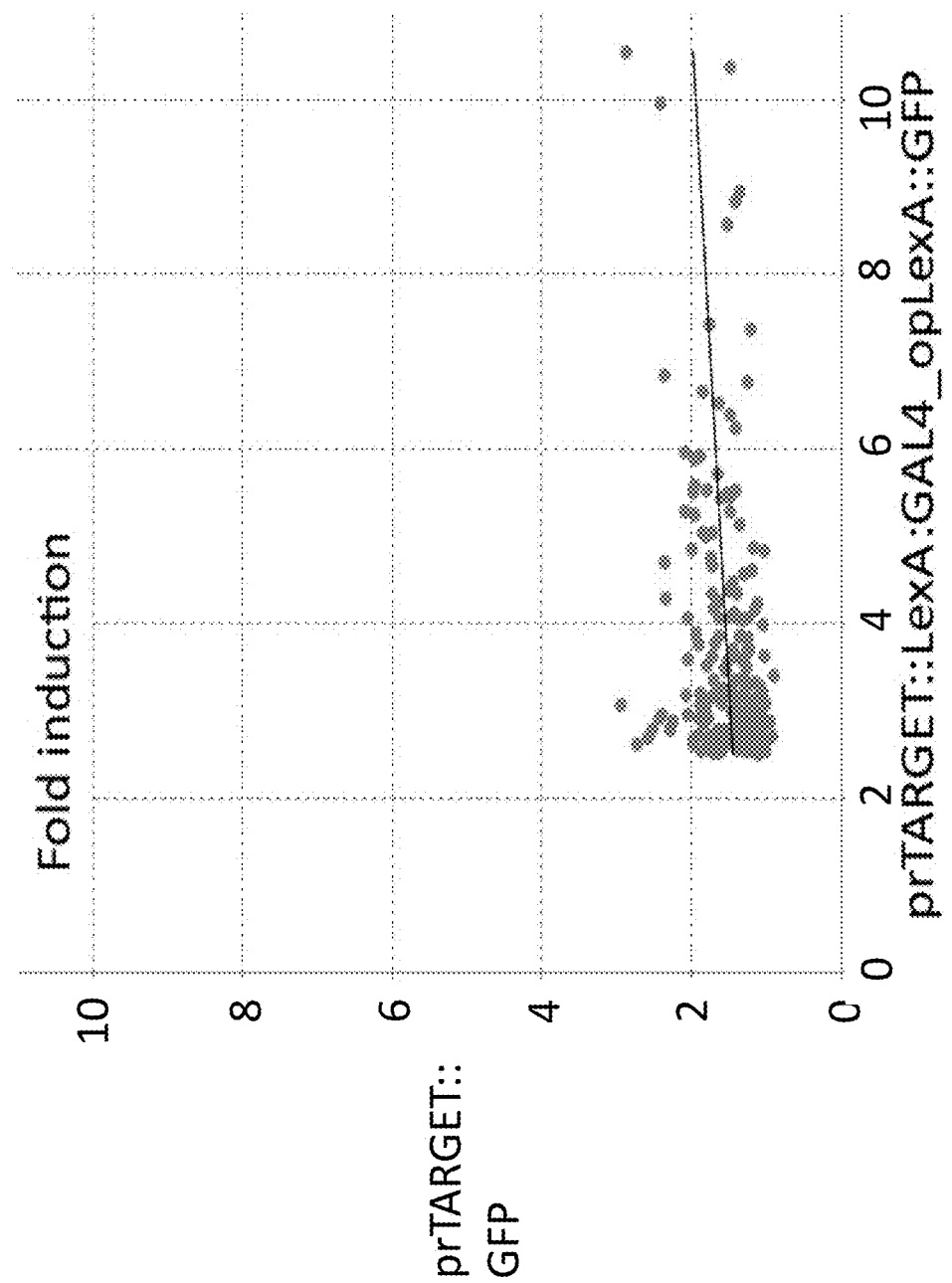

FIG. 7. Compound screening using the direct fusion and the two-component transcriptional fusion systems. Cell lines transformed with prTARGET::GFP (the direct fusion reporter system) or prTARGET::LexA:Ga14_oplexA::GFP (the two-component reporter system) were used in a primary screen on a 30K diverse compound panel to identify compounds that can induce the prTARGET promoter, Fold of induction, calculated by the GFP florescence value of the test compound-treated group relative to that of the control (DMSO)-treated group, is represented on the X axis for two-component system, and on the Y axis for the direct fusion reporter system. Several compounds that did not meet the threshold of 2.5 fold induction with the direct fusion reporter line were identified as hits using the improved two-component system, demonstrating the improved sensitivity of the two-component system.

FIG. 8. Four (4) out of twenty (20) compound hits, identified from a primary screen using the two-component reporter line, "C71125", "C66433", "C71126" and "C71124" (shown in FIGS. 8B, 8C, 8D, and 8E, respectively), conferred significant tolerance to desiccation stress with Arabidopsis seedlings (shown in FIG. 8A) relative to control compound, DMSO.

Figure 9:
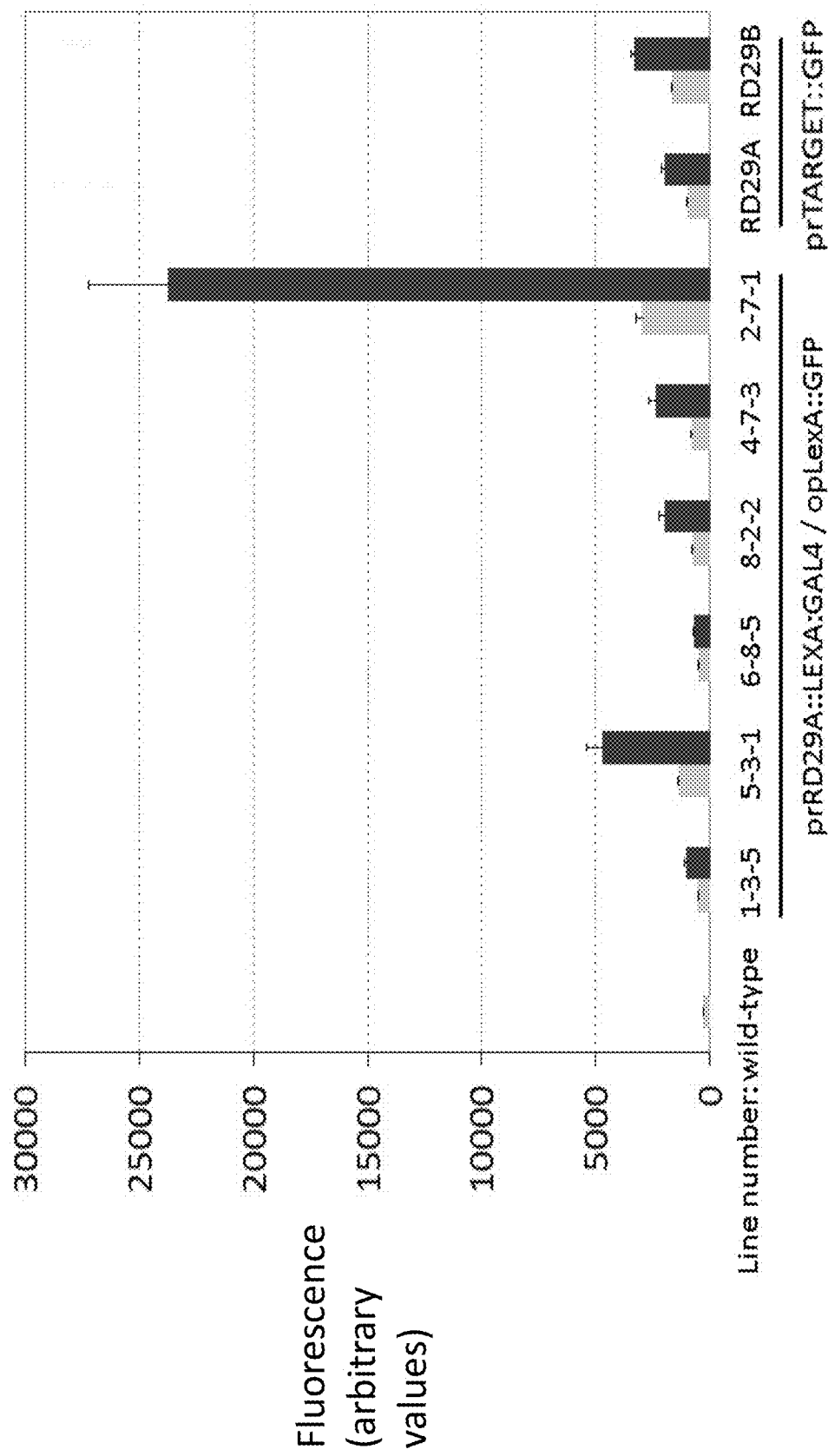

FIG. 9. A two-component transcriptional fusion system comprising a stress-inducible promoter RD29A. Cell lines transformed with prRD29A::LEXA:GAL4_opLEXA::GFP, i.e., "1-3-5", "5-3-1", "6-8-5", "8-2-2". "4-7-3", "2-7-1", and cell lines transformed with prRD29A::GFP (i.e., "RD29A") or prRD29B::GFP, (i.e., "RD29B"), were subjected to an ABA induction (black columns), or a mock treatment (gray columns) before data acquisition. The relative GFP fluorescence values are indicated by the Y axis and the standard errors (error bars; n=8) are shown at the top of the columns.

Figure 10:
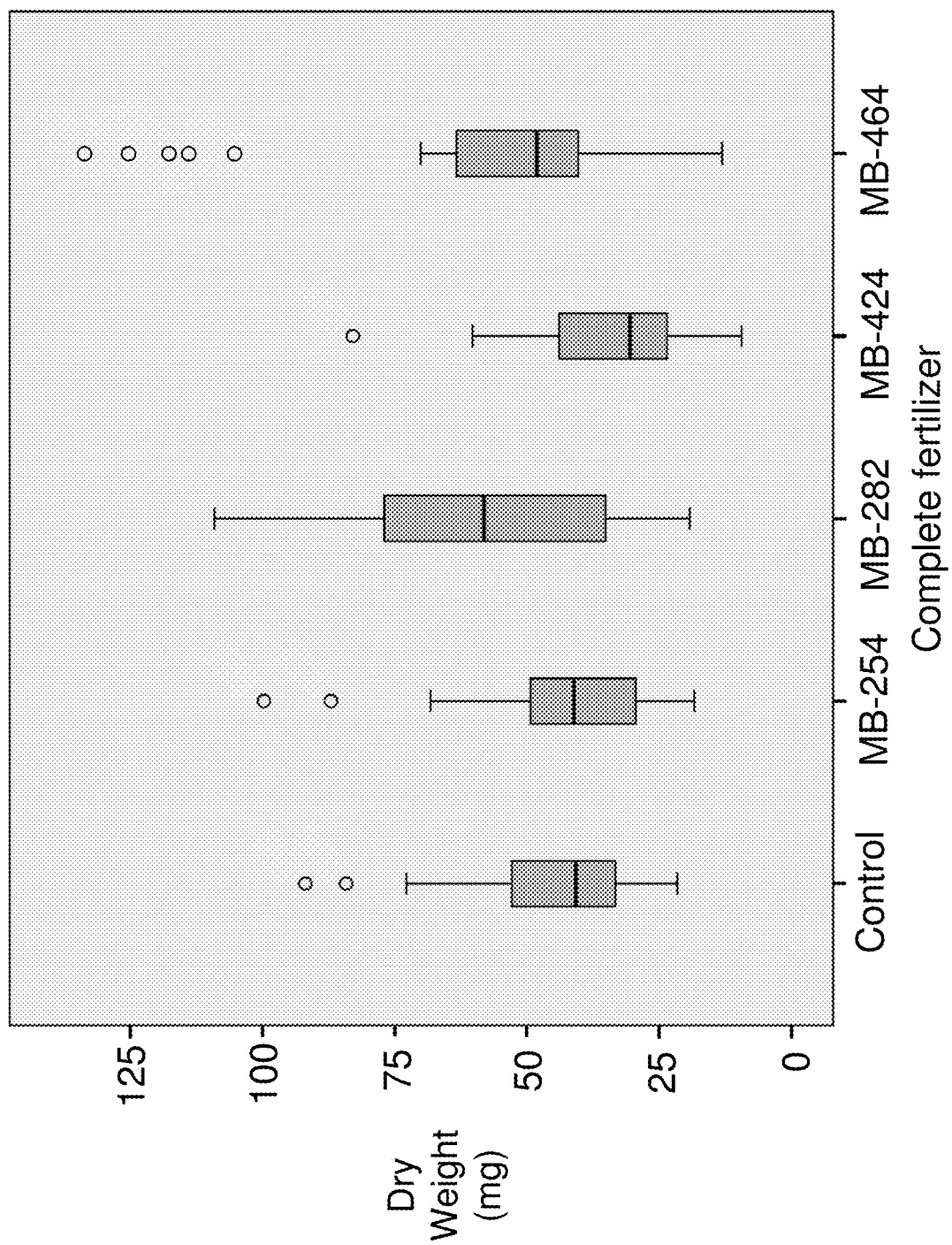

FIG. 10. Box-plot representation of biomass accumulation for Arabidopsis thaliana plants grown with complete fertilizer after application of several microbial culture preparations that putatively improve plant performance-related or yield-related traits. The thick line in each box represents the median of the sample. Circles represent sample outliers. Application of preparations MB-282 and MB-464 caused a statistically significant increase in biomass (p=0.038 and p=0.051, respectively) compared to the control treatment (microbial growth medium alone applied to Arabidopsis). Two other preparations, MB-254 and MB-424, did not confer a significant increase in Arabidopsis biomass compared to the controls.

Figure 11:
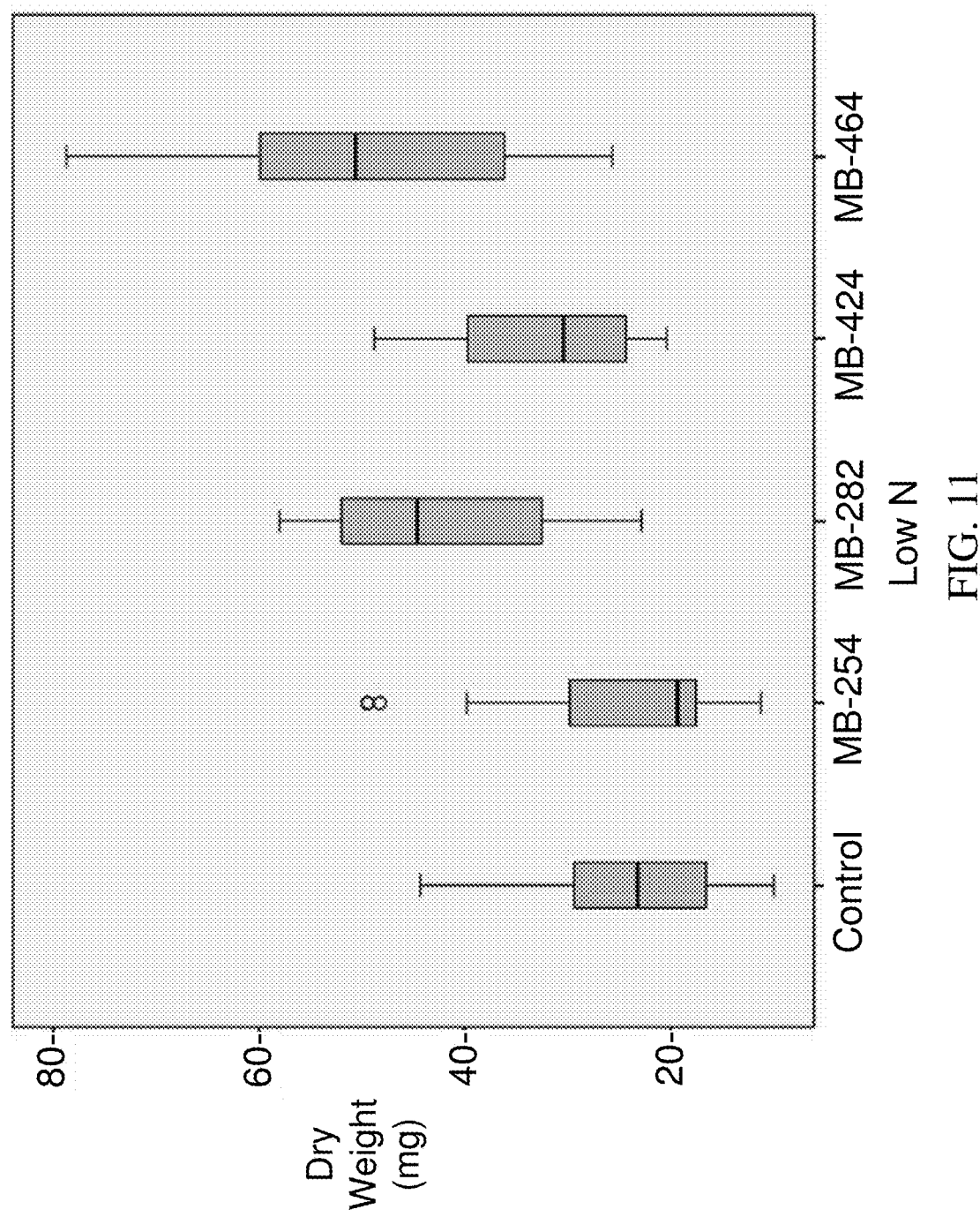

FIG. 11. Box-plot representation of biomass accumulation for Arabidopsis thaliana plants grown with low nitrogen fertilizer after application of several microbial culture preparations that putatively improve plant performance-related or yield-related traits. The thick line in each box represents the median of the sample. Circles represent sample outliers. Application of MB-282, MB-424, and MB-464 caused a statistically significant increase in biomass (p=0.000, p=0.023, and p=0.000, respectively) compared to the control treatment (microbial growth medium alone). The preparation MB-254 did not confer a significant increase in biomass compared to the controls.

Figure 12:
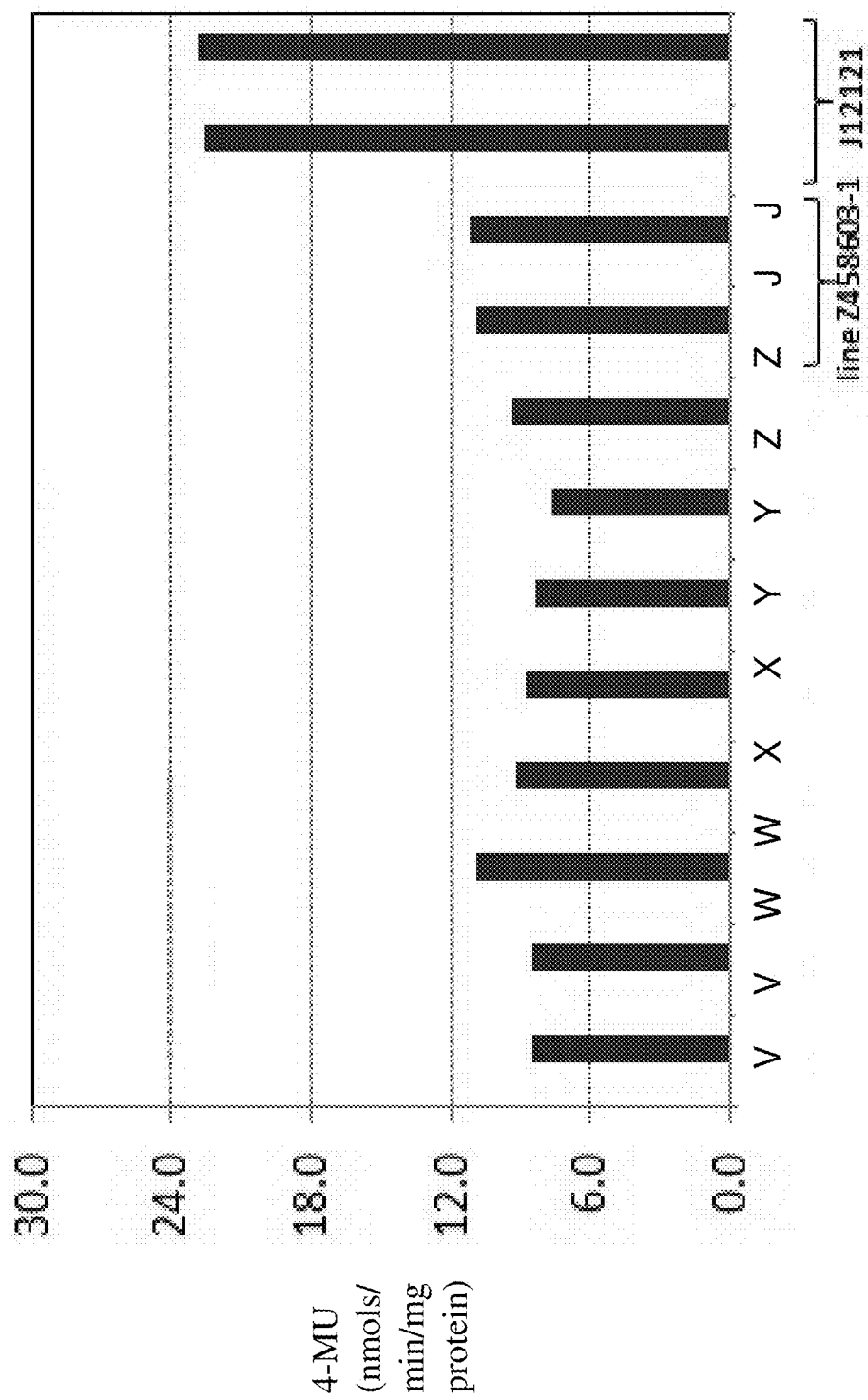

FIG. 12. Quantitative 4-methylumbelliferyl-beta-D-glucuronide (MUG) expression assay showing induced GUS activity, shown as level of 4-MU (Y axis), in multiple independent homozygous lines (X axis).

Figure 13:
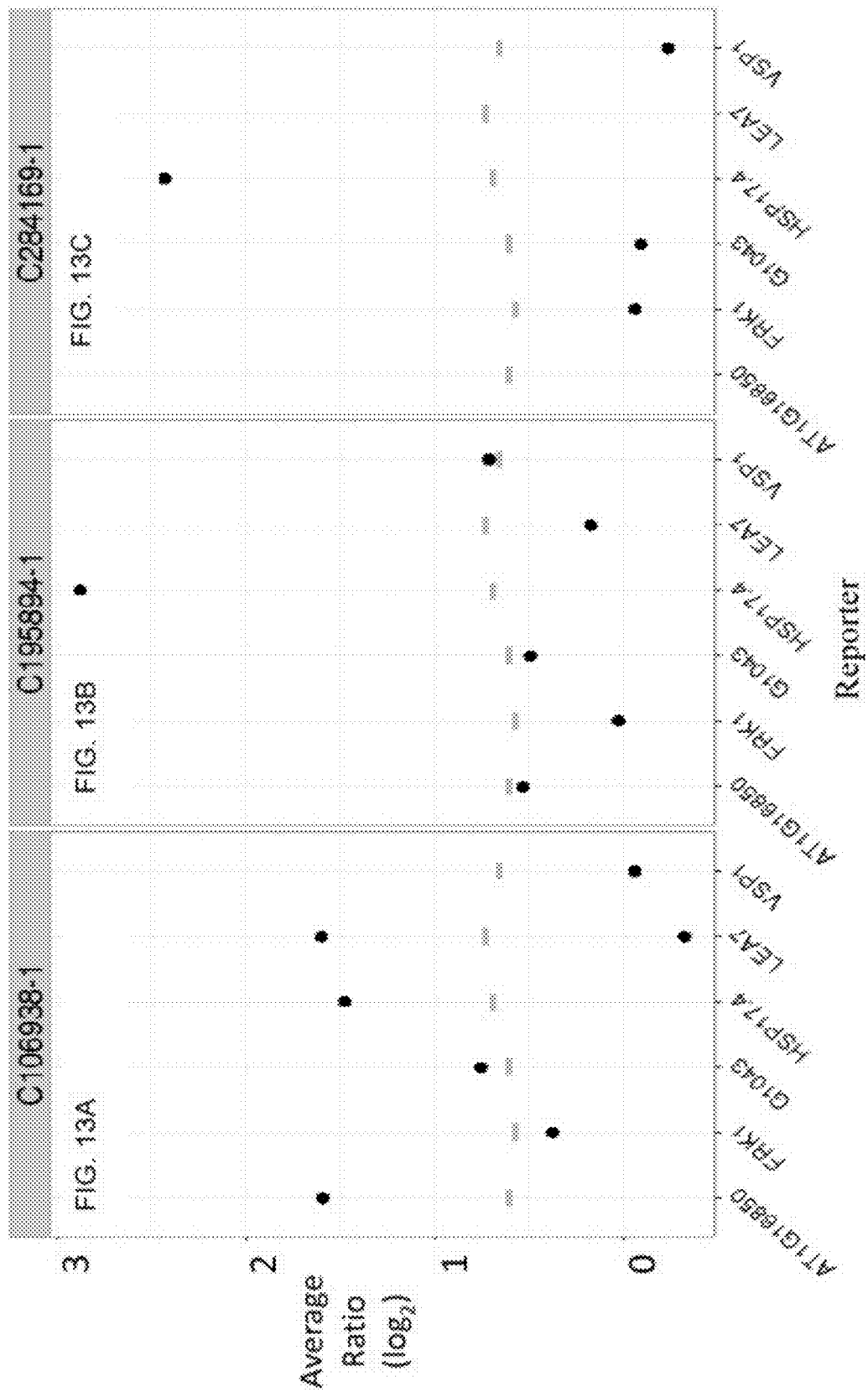
Figure 14:
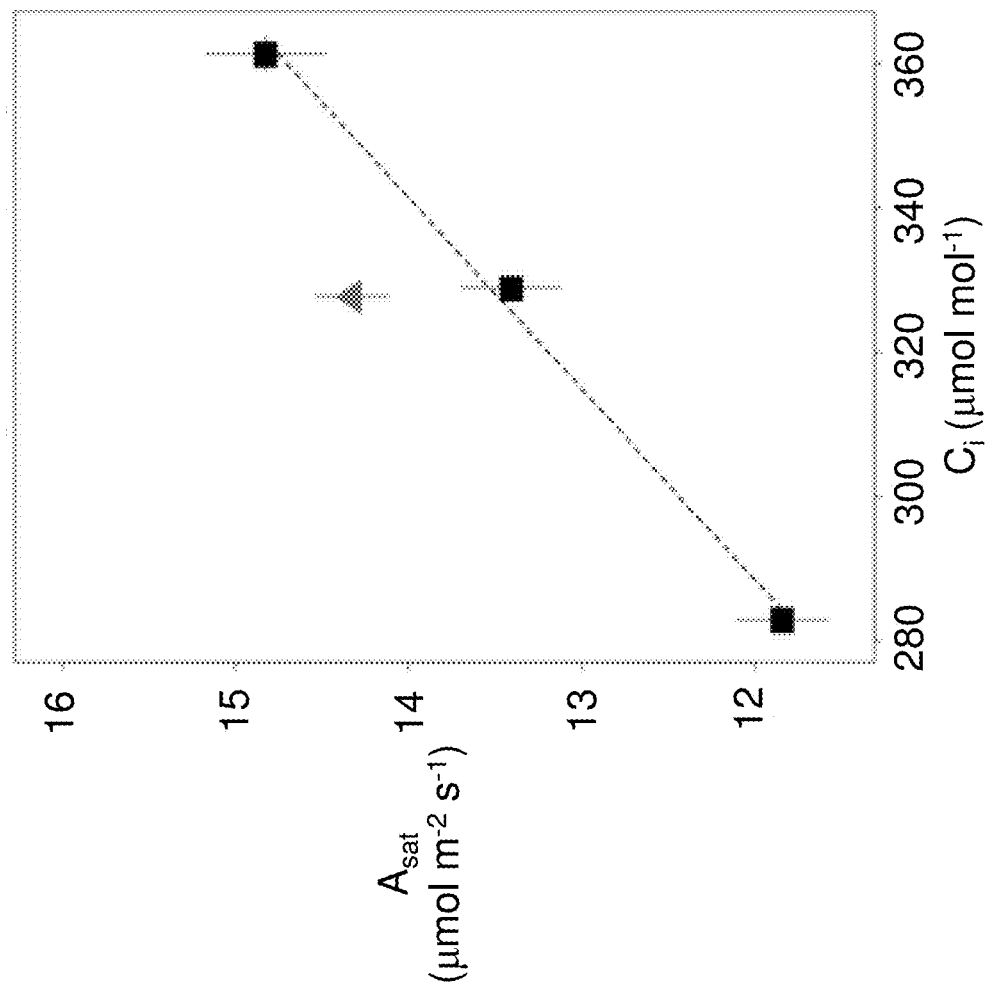
Figure 15:
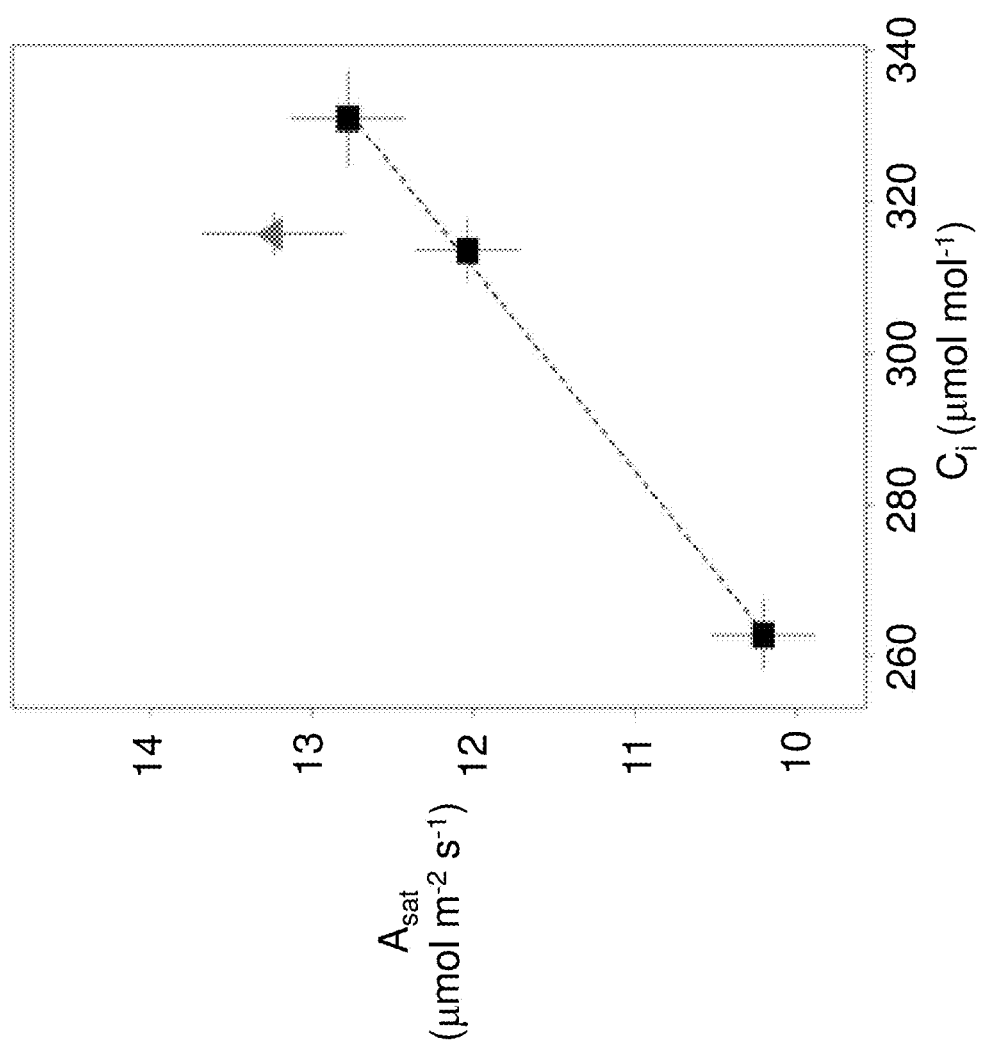

In FIGS. 13-15, the mean values per set of plants in experimental treatments are shown as a gray triangle. Values obtained with mock treated control plants (black squares treated with 0.01% Kinetic surfactant in water) are fitted to a linear model indicated by the diagonal line. The vertical axis units indicate photosynthetic capacity as measured light saturated photosynthesis determined from the rate of $CO_2$ absorbance under saturating photosynthetic photon flux (PFF) density or $A_{sat}$, which is expressed as $\mu mol\ m^{-2}\ sec^{-1}$. The Asat measurements were evaluated relative to controls in conjunction with the respective estimates the horizontal axis units of internal $CO_2$ concentrations ($C_i$; $\mu mol\ mol^{-1}$).

FIGS. 13A, 13B and 13C are dot plots showing the average $\log_2$ ratio of fluorescence from compound treated vs. mock treated samples (y-axis) across multiple reporter lines (x-axis). Circles represent average $\log_2$ ratio for a specific compound treatment in a given reporter genotype. Bars indicate a significance threshold, which is set to be 2.5 times the inter quartile range of the response distribution of each promoter reporter genotype. Each figure panel groups the treatments of a specific compound, as indicated in the panel header. Three different compounds were identified by this screening method in five different promoter reporter genotypes. Compound C106938 (FIG. 13A) induced reporter activity of four different reporter genotypes, AT1G16850, G1043, HSP17.4 and LEA7 to a significant degree, Compound C195894 (FIG. 13B) induced reporter activity in two reporter lines including HSP17.4 and VSP1, and C284169 (FIG. 13C) in the reporter line HSP17.4.

FIG. 14. Photosynthetic capacity of Arabidopsis plants after treatment with C106938. FIG. 14 shows the effect of treatment with test compound C106938 (gray triangle) at an application rate equivalent to 361 liters per hectare on the yield-related trait of photosynthetic capacity (determined as $A_{sat}$ vs. $C_i$) in mature Arabidopsis thaliana plants. X68369 is a control treatment. C106938 has been independently tested 14 times, and meta-analysis across all experiments shows a highly significant effect ($p \leq 0.0001$), with an average increase of 6.7%.

FIG. 15. Photosynthetic capacity of Arabidopsis plants after treatment with C195894. FIG. 15 shows the effect of the effect of treatment with test compound C195894 (gray triangle) at an application rate equivalent to 361 liters per hectare on photosynthetic capacity in mature Arabidopsis thaliana plants. This compound has been independently tested 14 times, and meta-analysis across all experiments shows a highly significant effect ($p \leq 0.0001$), with an average increase of 6.0%.

Figure 16:
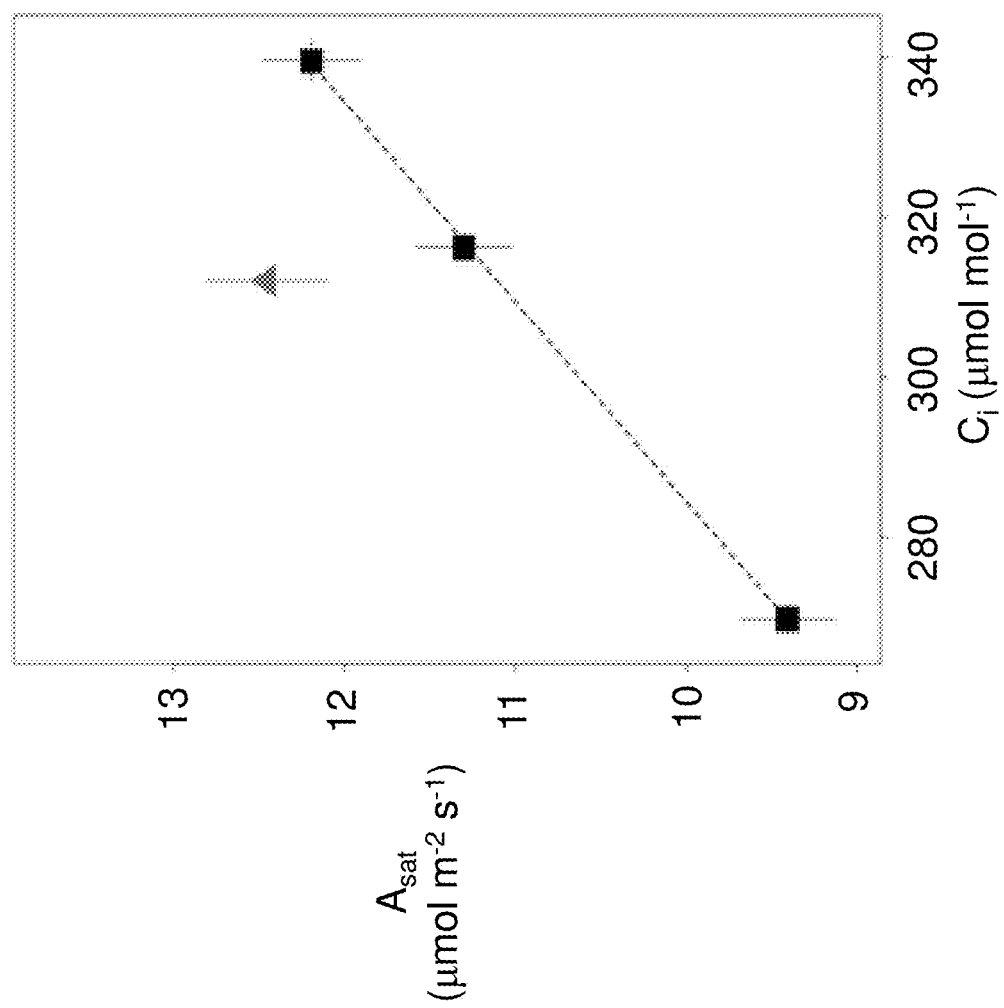

FIG. 16. Photosynthetic capacity of *Arabidopsis* plants after treatment with C284196. FIG. 16 shows the effect of treatments with compound C284169 (gray triangle) at an application rate equivalent to 361 liters per hectare on photosynthetic capacity in mature *Arabidopsis thaliana* plants, independently tested 13 times. Meta-analysis across all experiments shows a highly significant effect ($p \leq 0.00001$), with an average increase of 6.6%.

DETAILED DESCRIPTION

The instant description relates generally to reporter constructs and their use in gene regulation. The instant description provides methods for identification of chemical compounds that can be applied to enhance the yield or performance or modify phenotypes of an organism or in vitro culture. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the instant description.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "reporter polynucleotide" is a polynucleotide that encodes a reporter protein, whose expression level or activity can be quantified by colorimetric, fluorescent or luminescence signals. Commonly-used reporter proteins include but are not limited to, beta-galactosidase (LacZ), green fluorescent protein (GFP), luciferase (LUC), chloramphenicol transferase (CAT), and glucuronidase (GUS).

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcriptional regulatory polypeptide gene encodes a transcriptional regulatory polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "transgenic or transformed plant" refers to a plant which contains a recombinant polynucleotide introduced by transformation. Transformation means introducing a nucleotide sequence in a plant in any manner to cause stable or transient expression of the sequence. This may be achieved by transfection with viral vectors, transformation with plasmids, such as *Agrobacterium*-based vectors, or introduction of naked DNA by electroporation, lipofection, or particle gun acceleration. A transformed plant may refer to a whole plant as well as to seed, plant tissue, plant cells or any other plant material, and to the plant's progeny.

A "transgenic organism" refers to an organism, such as a plant, a microbe, a mammal, yeast, *Drosophila, C. elegans*, etc., which contains a recombinant polynucleotide introduced by transformation. Transformation means introducing a nucleotide sequence in an organism in any manner to cause stable or transient expression of the sequence. This may be achieved by transfection with viral vectors, transformation with plasmids, or introduction of naked DNA by electroporation, lipofection, or particle gun acceleration. A transformed organism may refer to a whole organism, to any part of the organism, to any materials derived from the organism, and to an offspring of the organism.

A "vector" is a nucleic acid construct, generated recombinantly or synthetically, comprising nucleic acid elements that can cause expression of a gene. A "donor vector" is a construct for expression of a polynucleotide sequence for a transactivator gene. The transactivator gene is operably linked to a promoter. The promoter region may include tissue active-or-specific promoters, developmental stage active-or-specific promoters, inducible promoters or constitutive promoters.

A "polypeptide of interest" maybe any peptide, including, for example, a polypeptide sequence for a regulatory gene such as a transcriptional regulatory polypeptide, a protein kinase or a phosphatase. These sequences may be in a sense or antisense orientation, or partial or complete gene sequences.

The phrase "altered or modified expression" in reference to polynucleotide or polypeptide expression refers to an expression pattern in a transgenic organism that is different from the expression pattern in the wild type plant or a reference plant; for example, by expression in a cell type other than a cell type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to lowering the levels of expression to below the detection level or completely abolishing expression. The resulting expression pattern may be transient or stable, constitutive or inducible.

A "promoter" or "promoter region" refers to an RNA polymerase binding site on a segment of DNA, generally found upstream or 5' relative to a coding sequence under the regulatory control of the promoter. The promoter will generally comprise response elements that are recognized by transcriptional regulatory polypeptides. transcriptional regulatory polypeptide may bind to the promoter sequences, recruiting RNA polymerase, which synthesizes RNA from the coding region. Dissimilarities in promoter sequences account for different efficiencies of transcription initiation and hence different relative expression levels of different genes.

"Promoter function" includes regulating expression of the coding sequences under a promoter's control by providing a recognition site for RNA polymerase and/or other factors, such as transcriptional regulatory polypeptides, all of which are necessary for the start of transcription at a transcription initiation site. A "promoter function" may also include the extent to which a gene coding sequence is transcribed to the extent determined by a promoter sequence.

The term "operably linked" refers to the association of polynucleotide sequences so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation. The polynucleotide molecules may be part of a single contiguous polynucleotide molecule and may be adjacent. For example, a promoter is operably linked to a gene of interest if the promoter modulates transcription of the gene of interest in a cell.

The term "DNA sequence-specific transactivator" refers to a polypeptide that comprises at least a DNA binding domain that binds to DNA with some degree of specificity and a transcriptional activation domain that has the function of activating transcription. A common feature of some activation domains is that they are designed to form amphiphilic alpha helices with negative charge (Giniger and Ptashne (1987)*Nature* 330:670-672, Gill and Ptashne (1987) *Cell* 51:121-126, Estruch et al (1994) *Nucl. Acids Res.* 22:3983-3989). Examples include the transcription activation region of VP16 or GAL4 (Moore et al. (1998) *Proc. Natl. Acad. Sci. USA* 95: 376-381; and Aoyama et al. (1995) *Plant Cell* 7:1773-1785), peptides derived from bacterial sequences (Ma and Ptashne (1987) *Cell* 51; 113-119) and synthetic peptides (Giniger and Ptashne, supra), or the EDLL domain from plants (Mendel's PCT application PCT/US2009/048814). Exemplary transactivators are those described in Brent and Ptashne, U.S. Pat. No. 4,833,080, herein incorporated by reference or in Hasselhoff and Hodge, WO97/30164.

"Activation" of a promoter-reporter construct is considered to be achieved when the activity value relative to control, e.g., a sample that is not treated with a test compound, is 105%, 110%, 120%, 130%, 140%, 150%, 200%, 250%, 300%, 400%, 500%, or 1000-3000% or more higher.

The phrases "coding sequence," "structural sequence," and "transcribable polynucleotide sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and transcribable polynucleotide sequence encode a series of amino acids forming a protein, polypeptide, or peptide sequence. The coding sequence, structural sequence, and transcribable polynucleotide sequence may be contained, without limitation, within a larger nucleic acid molecule, vector, etc. In addition, the orderly arrangement of nucleic acids in these sequences may be depicted, without limitation, in the form of a sequence listing, figure, table, electronic medium, etc.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcriptional regulatory polypeptide or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type organism. Alternatively, or additionally, the isolated polypeptide is separated from other cellular components with which it is typically associated, e.g., by any of the various protein purification methods herein.

The instant description also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the instant description is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in an organism being treated with the chemical compounds of the instant description relative to a control organism of the same species, the latter including organisms treated with a control compound or a carrier solvent or no treatment. In some cases, the trait modification can be evaluated quantitatively. For example, the trait modification can entail at least about a 2% increase or decrease, or an even greater difference, in an observed trait as compared with a control or wild-type organism. It is known that there can be a natural variation in the modified trait. Therefore, the trait modification observed entails a change of the normal distribution and magnitude of the trait in the plants as compared to control or wild-type organisms.

"Modulates" refers to a change in activity (biological, chemical, or immunological) or lifespan resulting from specific binding between a molecule and either a nucleic acid molecule or a protein.

"Ectopic expression or altered expression or modified expression" in reference to a polynucleotide indicates that the pattern of expression in, e.g., a transgenic organism or tissue, is different from the expression pattern in a wild-type organism or a reference organism of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type organism, or by expression at a time other than at the time the sequence is expressed in the wild-type plant, or by a response to different inducible agents, such as hormones or environmental signals, or at different expression levels (either higher or lower) compared with those found in a wild-type organism. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in an organism, a cell or a tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also occur under the control of an inducible or tissue specific promoter. Thus, overexpression may occur throughout an organism, in specific tissues of the organism, or in the presence or absence of particular environmental signals, depending on the promoter used.

Overexpression may take place in cells normally lacking expression of polypeptides functionally equivalent or identical to the present polypeptides. Overexpression may also occur in cells where endogenous expression of the present polypeptides or functionally equivalent molecules normally occurs, but such normal expression is at a lower level. Overexpression thus results in a greater than normal production, or "overproduction" of the polypeptide in the organism, cell or tissue.

The term "transcription regulating region" or "transcription regulating nucleic acid sequence" refers to a DNA regulatory sequence that regulates expression of one or more genes in an organism when a transcriptional regulatory polypeptide having one or more specific binding domains binds to the DNA regulatory sequence. Transcriptional regulatory polypeptides possess a conserved domain. The transcriptional regulatory polypeptides also comprise an amino acid subsequence that forms a transcription activation domain that regulates expression of one or more abiotic stress tolerance genes in an organism when the transcriptional regulatory polypeptide binds to the regulating region.

DESCRIPTION OF THE SPECIFIC EMBODIMENTS

The instant description provides novel reporter gene constructs that could be used to study gene regulation and identify novel sequences and agents that can be used to modify a phenotype of interest. The reporter gene system of the instant description can be a transcriptional fusion reporter system or a translational fusion reporter system.

Transcriptional Fusion Reporter System

The transcriptional fusion reporter system of the instant description comprises a reporter gene that is regulated by: 1) a target promoter sequence recognized by a transcriptional regulatory polypeptide, and 2) a DNA sequence-specific transactivator.

The transcriptional fusion reporter system can be used to identify compounds that modulate the activity of a target promoter. Plants or plant cells transformed with the transcriptional fusion reporter constructs can be treated with test compounds or compound libraries, and reporter gene expression can be monitored. Alternatively, the transformed organisms or cells containing the transcriptional fusion reporter constructs can be placed in a panel of microtiter wells and a panel of test compounds can be added to the cells, one compound to each well. A useful compound can be identified based on its ability to generate an enhanced or decreased reporter signal relative to control compounds.

The target promoters suitable for use herein can be any promoter that is recognized and regulated by a transcriptional regulatory polypeptide, including those that are constitutively active or those that are inducible or tissue enhanced or developmental-stage active promoters. In a preferred embodiment, the target promoters are the ones that regulate plant trait development. The target promoters can be naturally derived or synthetically made. The minimal promoter for use in synthetic promoters can be from any promoter. The minimal promoter supports basal transcription and typically comprises regulatory elements such as TATAA sequences. Exemplary minimal promoter regions can be from promoters such as the cauliflower mosaic virus (CaMV) 35S transcription initiation region, and other transcription initiation regions from various genes known to those of skill.

In some embodiments of the instant description, the target promoter activates the expression of a DNA sequence-specific transactivator, which recognizes and binds to a specific transcriptional regulatory sequence and induces high level reporter gene expression. For example, the target promoter could drive the expression of a translational fusion of a DNA binding domain (e.g., the LexA DNA binding domain) and a transcriptional activation domain (e.g., the Gal4 transcriptional activation domain). A reporter molecule would be expressed from a promoter bound by the DNA binding domain (e.g., the opLexA promoter) such that activation of the target promoter would result in amplified expression of the reporter gene mediated by the DNA sequence-specific transactivator (e.g., LEXA:GAL4) (FIG. 2). This system thus enables more sensitive reporter detection compared to direct promoter-reporter fusion construct, and is particularly advantageous when employing a promoter of a transcriptional regulatory polypeptide or for targets with low expression levels or when screening for compounds that can down-regulate the activity of a target promoter or a transcriptional regulatory polypeptide that recognizes the target promoter.

The DNA sequence-specific transactivator of the transcriptional fusion system can also comprise a dexamethasone responsive element, for example, a target promoter could drive the expression of a translational fusion of the LexA DNA binding domain, the Gal4 transcriptional activation domain and the ligand binding domain of the glucocorticoid receptor (GR). An example of this inducible reporter system involves introducing a dexamethasone-responsive cassette, e.g. a polynucleotide encoding a fusion protein LEXA:GAL4:GR, and a transcriptional fusion of a target promoter and a reporter gene into the cell, where the addition of dexamethasone results in high levels of expression of a transcriptional regulatory polypeptide, which would, in turn, activate a target promoter and result in high reporter expression (FIG. 1). These dexamethasone inducible reporter systems can be internally validated by the addition or withdrawal of dexamethasone and the expected reporter (e.g., the "reporter2" in FIG. 1) signal induction can be quantified prior to a high throughput screen. The benefit of this multi-component system would be the ease of identifying a candidate line with strong induction characteristics, eliminating lines with silencing or poor expression due to the chromosomal integration site. The control over the activation of the transgene by dexamethasone also minimizes the negative interference from constitutive expression of some transgenes. Furthermore, this dexamethasone-inducible system can achieve adjustable levels of reporter gene expression: in the absence of dexamethasone, endogenous transcriptional regulatory polypeptide binds to the target promoter and activates reporter gene expression to a relatively low level, while in the presence of dexamethasone, dexamethasone-inducible transactivator activates the expression of the exogenous transcriptional regulatory polypeptide, which in turn drives high level expression of the reporter gene; this system conveniently enables screening for chemistries that can repress (in the presence of dexamethansone) or activate (in the absence of dexamethasone) transcription from a target promoter with one singular construct and selected transgenic line;

A variant of the transcriptional fusion reporter system employs two different DNA sequence-specific transactivators with distinct DNA binding sequence specificities to activate reporter gene expression: a first DNA sequence-specific transactivator, in the presence of dexamethasone, induces the expression of a transcriptional regulatory polypeptide, which, in turn, binds its target promoter sequence and activates a second DNA sequence-specific transactivator, which subsequently activates the reporter gene expression (FIG. 3). A system as such assimilates advantages of both systems described above (and as shown in FIGS. 1 and 2) by incorporating an amplification component that boosts the sensitivity of the screen and a characterization component that eases the identification of suitable cell lines with strong induction characteristics.

In addition to compound screening, the transcriptional fusion reporter system can also be used to characterize novel promoter elements or promoter fragments in response to various environmental stimuli or activation signals. Any novel promoter element of interest can be used as a target promoter and incorporated in the transcriptional fusion reporter system, which is then introduced into the cells and monitored for the ability to affect reporter gene activity under conditions that can activate a control promoter. The promoter function of the novel target promoter elements can be evaluated based on the ability to activate or repress the reporter gene activity relative to the control promoter sequence under the same conditions.

Translational Fusion Reporter System

The translational fusion reporter system of the present description comprises at least 1) a polynucleotide encoding a DNA sequence specific transactivator, 2) a polynucleotide encoding a fusion protein, and 3) a nucleotide sequence recognized by the DNA sequence specific transactivator. The genetic elements of 1), 2) and 3) are arranged in a way such that the DNA sequence-specific transactivator activates the expression of a translational fusion of a reporter molecule and a polypeptide of interest.

The translational reporter system of the instant description can be used to identify compounds that can modulate the stability of a polypeptide of interest. Test compounds and control compounds are applied to the cells transformed with the translational fusion constructs. Test compounds that change the stability of polypeptides of interest can be identified based on the altered reporter gene activity levels relative to controls. Hit compounds can be applied to the organisms of interest, for example, plants, bacteria, cell cultures etc., and further validated for the ability to change the stability of the polypeptide of the interest using biochemical approaches that are known in the art.

The polypeptide of interest may be any polypeptide, but is preferably a regulatory polypeptide, such as a transcriptional regulatory polypeptide, a phosphatase or a protein kinase. The polypeptide of interest may be from any species, particularly plant species, in a naturally occurring form or from any source whether natural, synthetic, semi-synthetic or recombinant. The polypeptide sequences may also include fragments of the present amino acid sequences of a regulator polypeptide, in particular a fragment with biological activity. In one preferred embodiment, the polypeptides of interest are all the transcriptional regulatory polypeptides identified in a plant, such as those identified in *Arabidopsis thaliana*. These transcriptional regulatory polypeptides collectively control all gene expression in plants and thus control all plant traits.

The plant transcriptional regulatory polypeptides may belong to one of the following transcription factor families: the AP2 (*APETALA2*) domain transcription factor family (Riechmann and Meyerowitz (1998) *J. Biol. Chem.* 379: 633-646); the MYB transcription factor family (Martin and Paz-Ares, (1997) *Trends Genet.* 13:67-73); the MADS domain transcription factor family (Riechmann and Meyerowitz (1997) *J. Biol. Chem.* 378:1079-1101); the WRKY protein family (Ishiguro and Nakamura (1994) *Mol. Gen. Genet.* 244:563-571); the ankyrin-repeat protein family (Zhang et al. (1992) *Plant Cell* 4:1575-1588); the zinc finger protein (Z) family (Klug and Schwabe (1995) *FASEB J.* 9: 597-604); the homeobox (HB) protein family (Duboule (1994) *Guidebook to the Homeobox Genes*, Oxford University Press); the CAAT-element binding proteins (Forsburg and Guarente (1989) *Genes Dev.* 3:1166-1178); the squamosa promoter binding proteins (SPB) (Klein et al. (1996) *Mol. Gen. Genet.* 1996 250:7-16); the NAM protein family (Souer et al. (1996) *Cell* 85:159-170); the IAA/AUX proteins (Rouse et al. (1998) *Science* 279:1371-1373); the HLH/MYC protein family (Littlewood et al. (1994) *Prot. Profile* 1:639-709); the DNA-binding protein (DBP) family (Tucker et al. (1994) *EMBO J.* 13:2994-3002); the bZIP family of transcription factors (Foster et al. (1994) *FASEB J.* 8:192-200); the Box P-binding protein (the BPF-1) family (da Costa e Silva et al. (1993) *Plant J.* 4:125-135); the high mobility group (HMG) family (Bustin and Reeves (1996) *Prog. Nucl. Acids Res. Mol. Biol.* 54:35-100); the scarecrow (SCR) family (Di Laurenzio et al. (1996) *Cell* 86:423-433); the GF14 family (Wu et al. (1997) *Plant Physiol.* 114:1421-1431); the polycomb (PCOMB) family (Kennison (1995) *Annu. Rev. Genet.* 29:289-303); the teosinte branched (TEO) family (Luo et al. (1996) *Nature* 383:794-799; the ABI3 family (Giraudat et al. (1992) *Plant Cell* 4:1251-1261); the triple helix (TH) family (Dehesh et al. (1990) *Science* 250:1397-1399); the EIL family (Chao et al. (1997) *Cell* 89:1133-44); the AT-HOOK family (Reeves and Nissen (1990)) *Journal of Biological Chemistry* 265:8573-8582); the S1FA family (Zhou et al. (1995) *Nucleic Acids Res.* 23:1165-1169); the bZIPT2 family (Lu and Ferl (1995) *Plant Physiol.* 109:723); the YABBY family (Bowman et al. (1999) *Development* 126:2387-96); the PAZ family (Bohmert et al. (1998) *EMBO J.* 17:170-80); a family of miscellaneous (MISC) transcription factors including the DPBF family (Kim et al. (1997) *Plant J.* 11:1237-1251) and the SPF1 family (Ishiguro and Nakamura (1994) *Mol. Gen. Genet.* 244:563-571); the golden (GLD) family (Hall et al. (1998) *Plant Cell* 10:925-936); or any other class of protein that is capable of directly or indirectly binding DNA and regulating the expression of a target gene.

Other transcriptional regulatory polypeptides may be identified by screening polynucleotide or polypeptide sequence databases, such as GenBank®, using sequence alignment methods and homology calculations, such as those described in Altschul et al. (1994) Nature Genetics 6: 119-129. For example, the NCBI Basic Local Alignment Search Tool (BLAST®) (Altschul et al. (1990) *J. Mol. Biol.* 215:403-410) is available from several sources, including the National Center for Biotechnology Information (NCBI, Bethesda, Md., for use in connection with the sequence analysis programs blastp, blastn, blastx, tblastp, tblastn and tblastx). Alternatively, a program that identifies particular sequence motifs may be employed along with specific characteristic consensus sequences, such as FIND PATTERN (GCG, Madison, Wis.).

Exemplary plant transcriptional regulatory polypeptides that can be employed in the instant description include Gilmour et al. (1998) teach an *Arabidopsis* AP2 transcription factor, CBF1, which, when overexpressed in transgenic plants, increases plant freezing tolerance. For another example, Bruce et al. (2000); and Borevitz et al. (2000) teach that the PAP2 gene and other genes in the MYB family control anthocyanin biosynthesis through regulation of the expression of genes known to be involved in the anthocyanin biosynthetic pathway. Applicants' own patent publication no. US20080010703A1, which is herein incorporated by reference in its entirety, has disclosed regulatory proteins involved in plant light signaling pathways and alteration in the expression or activity of which have resulted in increased yield in plants. In addition, Applicants' patent publication no. US20090138981A1, which is herein incorporated by reference in its entirety, has listed transcriptional regulatory polypeptides that are involved in various plant signaling pathways and cellular events that impact on plant disease resistance, biomass production and abiotic stress tolerance. Accordingly, one skilled in the art would recognize that changing the expression of the present sequences in a plant would introduce modified traits not found in the wild-type cultivar or strain.

The DNA sequence-specific transactivator can be any transactivator that comprises at least a DNA binding domain and a transcriptional activation domain and has transcription-regulation activity, for example, a translational fusion of the LexA DNA binding domain and the Gal4 transcriptional activation domain. The translational fusion system of the instant description comprising DNA sequence-specific transactivator enables high level of reporter expression can be especially useful for identifying compounds that can decrease the stability of a polypeptide of interest (FIG. 4). Similar to what has been described in the transcriptional reporter system described above, various arrangements and combinations of sequences encoding DNA sequence-specific transactivator and dexamethasone inducible cassettes can be incorporated into the system in order to facilitate reporter line characterization and development, improve signal to noise ratio of the screening assay, and enhance screening efficiency. In addition, the various genetic elements included in both the transcriptional fusion reporter systems and translational fusion reporter systems described herein may reside in a single construct, or in multiple constructs with various selection markers. The multiple constructs can be transformed into an organism of interest, and transgenic organisms or cells carrying the desired genetic elements can be identified through the detection of the expression of appropriate selection markers. For example, a reporter system of the instant description may consist of two reporter constructs, with the polynucleotide encoding a DNA sequence-specific transactivator, e.g. LEXA:GAL4, comprised in one construct and the promoter responsive to the DNA sequence-specific transactivator, e.g. opLEXA, and the polynucleotide encoding the reporter or reporter fusion in the other.

Reporter Genes

Reporter genes suitable for use in the instant description are known to those of skill in the art. Reporters can be any protein, and include, but are not limited to, fluorescent proteins, such as green or red fluorescent proteins, or variants that produce a fluorescent color; β-glucuronidase (GUS); luciferase; chloramphenicol acetyltransferase; β-galactosidase; and alkaline phosphatase. Commonly used reporter genes include those encoding proteins that can generate quantifiable fluorescent, colorimetric, or luminescent signals. Transcription of the sequences encoding the reporter gene can be determined using any method known in the art. In some embodiments, protein activity of the reporter gene is measured, e.g., using a fluorescent reader or other instrumentation appropriate to the reporter system. Products to assist in determination of reporter activity are commercially available.

Samples that are treated with a test compound, or pool of test compounds, are compared to control samples without the test compound to examine the extent of modulation. Control samples (untreated with activators are assigned a relative activity value. Activation is then achieved when the reporter activity value relative to the control is 105%, 105-150%, optionally 150%, 150-500%, or 500-2000% or more, whereas down-regulation is achieved when the reporter activity value relative to the control is 70-90%, 66%, 20-50%, or 5-10%.

In other embodiments, endpoints other than reporter activity are assayed. For example, expression levels of the mRNA or protein can be measured to assess the effects of a test compound on reporter activation. In this instance, the expression of the reporter construct is measured by assessing the level of mRNA that encodes the reporter gene or the translational fusion of the reporter gene and a polypeptide of interest, or alternatively of the protein product. These assays can be performed using any methods known by those of skill in the art to be suitable. For example, mRNA expression can be detected using amplification-based methodologies, northern or dot blots, nuclease protection and the like. Polypeptide products can be identified using immunoassays.

Introduction of Reporter Constructs into Hosts or Host Cells

Reporter constructs can be introduced into the desired hosts or cells derived therefrom, such as plants, microbes, mammals, yeast, *Drosophila*, *C. elegans* by a variety of conventional and well-known techniques. For example, the vector can be introduced directly into the host cells using techniques such as electroporation, microinjection, and biolistic methods, such as particle bombardment.

Microinjection techniques are known in the art and well described in the scientific and patent literature. The introduction of DNA constructs using polyethylene glycol precipitation is described, e.g., in Paszkowski et al. (1984). Electroporation techniques are described in Fromm et al. (1985). Biolistic transformation techniques are described in Klein et al. (1987).

For transforming plants or plant cells, the reporter constructs may also be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example, Horsch et al. (1984), and Fraley et al. (1983).

The host plant cells for screening reporter constructs can be from any plant, including both dicots and monocots. Typically, plant cells are from *Nicotiana benthamiana* or *Arabidopsis thaliana* or another plant that is routinely transformed and assayed in the art.

Other plants also can be used in the screening methods taught herein. These include cereals, for example, maize, sorghum, rice, wheat, barley, oats, rye, milo, flax, or gramma grass. Other plant genera include, but are not limited to, *Cucurbita, Rosa, Vitis, Juglans, Gragaria, Lotus, Medicago, Onobrychis; Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*.

Following transformation of the reporter constructs into the plant cell, the transformed cell or plant tissue is selected or screened by conventional techniques. The transformed cell or plant tissue containing the reporter construct can then be regenerated, if desired, by known procedures. Additional methodology for the generation of plants comprising expression constructs for screening chemicals can be found in the art (see, e.g., U.S. Pat. No. 5,614,395).

Chemical Libraries

The compounds tested as modulators of yield regulators are typically chemical compounds. Essentially any chemical compound of interest can be used to activate or down-regulate the activity of the promoters of the instant description or to stabilize the polypeptides of the instant description using the assays as described. Most often, compounds can be dissolved in aqueous or organic (e.g., DMSO-based) solutions. The assays are designed to screen large chemical libraries and usually include automating the assay steps, which are typically run in parallel (e.g., in microtiter formats on microtiter plates in robotic assays). It will be appreciated that there are many suppliers of chemical compounds, including Sigma-Aldrich (St. Louis, Mo.), Fluka Chemika-Biochemica Analytika (Buchs, Switzerland) and the like.

In one preferred embodiment, high throughput screening methods involve providing a combinatorial chemical library containing a large number of test compounds. Such "combinatorial chemical libraries" are then screened in one or more assays, as described herein, to identify those library members (particular chemical species or subclasses) that activate or down-regulate the activity of the promoters of the instant description. The compounds thus identified serve as conventional "lead compounds" or can themselves be used as potential or actual agents for treating plants or other organisms.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, small organic molecule libraries (see, e.g., U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like). Other chemistries for generating chemical diversity libraries can also be used. Chemical diversity libraries are also commercially available, e.g., from such companies as 3-Dimensional Pharmaceuticals Inc., Albany Molecular Research Inc., Alchemia Pty. Ltd., Argonaut Technologies Inc., ArQuie Inc, Biofocus DPI, Array Biopharma Inc., Axys Pharmaceutical Inc., Cambridge Combinatorial Ltd., Charybdis Technologies Inc, ChemBridge Corp., CombiChem Inc., ComGenex Inc., Discovery Partners International Inc., Diversa Corp., EnzyMed Inc. Versicor, Gryphon Sciences Inc, Ixsys Inc., Kosan Biosciences Inc., Maxygen Inc., Molecumetics Ltd., Nanoscale Combinatorial Synthesis Inc., Ontogen Corp., Orchid Biocompter Inc., Oxford Asymmetry Ltd., Oxford Molecular Group PLC, Panlabs Inc., Pharmacopeia Inc., Phytera Inc., Proto Gene Inc., Sphere Biosystems Inc., Symyx Technologies Inc., and Systems Integration Drug Discovery Co.

Often, chemical libraries that are screened in the methods of the instant description comprise compounds with molecular weights between 150 and 600, an average cLogP value of 3 (range 0-9), an average number of R-bonding acceptors of 3.5 (range 0-9), an average number of R-bonding donors of one (range 0-4) and an average of three rotatable bonds (range 0-9). Such characteristics are typical of agrichemicals known in the art.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries, are themselves commercially available (see, e.g., Chembridge, Inc., San Diego, Calif.; ComGenex, Princeton, N.J., Tripos, Inc., St. Louis, Mo., 3D Pharmaceuticals, Exton, Pa., Martek Biosciences, Columbia, Md., etc.).

High Throughput Assays

In the high throughput assays, it is possible to screen up to several thousand different test compounds in a single day. For example, each well of a microtiter plate can be used to run a separate assay against a selected test compound, or, if concentration or incubation time effects are to be observed, every 5-10 wells can test a single test compound. Further, pools of test compounds can also be tested where 25 multiple compounds are included in a single test sample. If a hit is then identified, the chemicals included in the pool can be individually tested to identify an active compound.

The compounds selected from the reporter assays are also evaluated using an additional screening step, for example, test compounds can be applied to an organism of interest and evaluated by measuring the presence or absence of a change in the level of the polypeptide of interest (if the compound is selected from the translational fusion reporter system) or a polypeptide that is regulated by the target promoter (if the compound is selected from the transcriptional fusion reporter system) by conventional methods known in the art, for example, RT-PCR analysis, western blot analysis, microarray hybridization, or sequencing based approaches.

In some embodiments of the instant description, the test compounds selected from the reporter gene system are subjected to a phenotypic analysis. A phenotypic analysis involves treating an organism with the test compound and detecting a modified trait which results from a change in the expression or activity of a polypeptide of interest, for example, a transcriptional regulatory polypeptide that regulates specific signaling pathways. In some embodiments, phenotypic analyses were performed on plants, which typically involve assays of abiotic stress tolerance such as water deprivation, dehydration, or osmotic stress, or assays that measure photosynthetic capacity.

Treatment of Plants

Once chemical compounds, particularly including compounds randomly selected prior to determining biological activity (that is, the compounds are "unbiased", with previously unknown or poorly understood function), are identified and further validated in accordance with the methods of the instant description, they can be used to treat any plant, for example, vegetable, fruit, and orchard crops, to enhance plant desiccation tolerance, disease tolerance or resistance, nitrogen use efficiency, performance, and/or yield.

Plants that can be treated include both monocots and dicots and in particular, agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, Brussels sprouts and kohlrabi). Other crops, fruits and vegetables whose phenotype may be changed include barley, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, sweet potato and beans. Lower plants such as algae can also be treated in this manner.

The selected chemicals can be formulated for treating plants as a liquid or a solid form. For example, in liquid formulations, the plants can be treated with a spray, in a drench application, a drip application, or through irrigation. Formulations are prepared using known methodology and may comprise other reagents conventionally employed in formulation of agricultural chemicals, e.g., emulsifying agents, surfactants, etc. Examples of formulations include emulsifiable concentrates, directly sprayable or dilutable solutions, dilute emulsions, wettable powders, soluble powders, dusts, granules or microcapsules. The methods of application, such as spraying, atomizing, dusting, wetting, scattering or pouring, are selected in accordance with the desired application. For example, a slow-release formulation can be applied as a soil treatment so that a plant is exposed frequently to an isolated chemical (e.g., turf grass). In other instance, it may be desirable to incorporate a chemical compound selected in accordance with the method of the instant description into irrigation water for plants that experience frequent droughts (e.g., cotton).

EXAMPLES

Example 1. Transcriptional Fusion Reporter System

The transcriptional fusion reporter system of the present invention comprises, in operable linkage, at least: a reporter gene, a target promoter sequence recognized by a transcriptional regulatory polypeptide, and a polynucleotide encoding a DNA sequence-specific transactivator. The reporter gene expression is controlled by the target promoter sequence and the DNA sequence-specific transactivator.

One exemplar transcriptional fusion reporter system expresses a dexamethasone-inducible transactivator, LEXA:GAL4:GR (SEQ ID NO: 1) and comprises: a) a transcriptional regulatory polypeptide encoded by a polynucleotide that is operably linked to the opLEXA promoter that is responsive to the dexamethasone-bound LEXA:GAL4:GR (SEQ ID NO: 2), and b) a reporter gene that is operably linked to the target promoter that is recognized by the transcriptional regulatory polypeptide. A DBD site::reporter1 component, for example, opLexA:reporter1, can also be included as a pre-characterization component to select cell lines and construct components that will impart strong inducible expression of the transcriptional regulatory polypeptide; under such circumstances, candidate polynucleotide sequence comprising promoter and DBD:AD:GR, and polynucleotide sequence of DBD site are introduced into a cell and their suitability for the screen are confirmed based on the ability of activating reporter expression ("reported") in response to dexamethasone treatment (FIG. 1).

Another exemplar transcriptional fusion reporter system comprises: a) a polynucleotide encoding a DNA sequence-specific transactivator LEXA:GAL4 (SEQ ID NO: 4), which is operably linked to a target promoter that can be recognized by a plant transcriptional regulatory polypeptide; b) a reporter gene operably linked to a opLEXA promoter (SEQ ID NO: 5) (FIG. 2). FIG. 9 shows an example of such a system, where a RD29A promoter is employed to control the expression of a LEXA:GAL4 transactivator, which, in turn, activates the reporter gene expression through regulating the opLEXA promoter. This two component system has been shown to increase significantly the signal-to-noise ratio of the assay compared to the direct fusion system, where the target promoter controls the transcription of the reporter polynucleotide directly.

Another exemplar transcriptional fusion reporter system expresses a dexamethasone-inducible DNA sequence-specific transactivator, e.g., GAL4BD:VP16:GR (SEQ ID NO: 7). It also comprises: a) polynucleotide that encodes a transcriptional regulatory polypeptide, operably linked to the GAL4UAS promoter region (SEQ ID NO: 11) that is responsive to the dexamethasone-bound GAL4BD:VP16:GR (SEQ ID NO: 7); b) a LEXA:GAL4 polynucleotide (SEQ ID NO: 3) that is operably linked to a target promoter responsive to the transcriptional regulatory polypeptide; and c) a reporter gene that is operably linked to a opLEXA promoter (SEQ ID NO: 5) (FIG. 3). As described above, a DBD1 site::reporter1 component can also be included to select cell lines that can strongly induce the expression of the target transcriptional regulatory polypeptide using the DBD1site promoter element.

These reporter constructs from the transcriptional fusion reporter system can be introduced into plants or plant cells to screen for compounds that can be used to modulate the activity of a target promoter that is recognized by a transcriptional regulatory polypeptide. The reporter gene expression can be monitored and compounds are selected on the basis of their ability to alter reporter expression or activity relative to controls.

Example 2. Translational Fusion Reporter System

The translational fusion reporter system of the present description comprises at least: 1) a polynucleotide encoding a DNA sequence specific transactivator, 2) a polynucleotide encoding a fusion protein, and 3) a nucleotide sequence recognized by the DNA sequence specific transactivator. The genetic elements of 1), 2) and 3) are arranged in a way such that the expression of a translational fusion of a reporter molecule and a polypeptide of interest is activated by the DNA sequence-specific transactivator.

One exemplar translational fusion reporter system expresses a LEXA:GAL4 fusion (SEQ ID NO: 4) protein and comprises a polynucleotide encoding a translational fusion of a reporter molecule and a polypeptide of interest that is operably linked to a opLEXA promoter (SEQ ID NO: 5) that is responsive to the LEXA:GAL4 (FIG. 4).

The reporter constructs of the translational fusion reporter system can be introduced into plants or plant cells to screen for compounds that can modulate the stability of a polypeptide of interest. The reporter gene expression can be monitored and compounds are selected on the basis of their ability to alter reporter expression or activity relative to controls. Hit compounds can be applied to plants and further validated for the ability to change the stability of the polypeptide of the interest through biochemical analyses that are known in the art.

Example 3. The Two Component Transcription Fusion System has an Improved Signal-to-Noise Ratio Compared to a Direct Transcriptional Fusion Aliquots of seeds for 10 independent lines harboring a prTARGET::LEXA:GAL4_opLEXA::GFP transgenic construct were surface sterilized (see Example 9), where prTARGET comprises a promoter element that regulates a gene involved in desiccation stress tolerance of *Arabidopsis*, and distributed into a 96-well polystyrene plate at a density of 5-10 seeds/well (n=16 wells) in standard liquid growth medium. In parallel, seeds were sterilized and distributed for the top performing prTARGET::GFP line previously identified from a study of over 20 independent lines based on the largest fold-increase in GFP reporter levels following an induction treatment which activates the promoter prTARGET. After six days of growth under 24h hour light (100 microE m-2 s-1) at 25 degrees C., eight wells/line were given the "induction treatment" and the other eight were "mock treated" and the plate was returned to the growth chamber. After 48 additional hours the plate was removed and fluorescence levels acquired using a Synergy HT multimode reader in area scan mode. FIG. 6 shows the average fluorescence and the standard error of the mean. Several of the two-component lines out-performed the classic direct fusion using fold-induction and background fluorescence levels as the selection criteria.

Example 4. A Two-Component Transcriptional Fusion System Comprising a Stress-Inducible Promoter RD29A Seeds from 10 independent lines harboring a prRD29A::LEXA:GAL4_opLEXA::GFP were surface-sterilized and plated in the same manner as described in Example 9 in parallel with the top-performing prRD29A::GFP and prRD29B::GFP line, which were identified previously from a study of multiple independent lines based on the largest fold-increase in GFP levels following an 1 µM ABA induction. Plants were grown in the same conditions as described in Example 3, except a 1 µM ABA induction which activates the RD29A and RD29B promoters was applied on day 5 of growth. Fluorescence levels of individual lines were acquired on day 8 and shown in FIG. 9. Several of the prRD29A::LEXA:GAL4_opLEXA::GFP exhibited significantly greater fold of GFP level increase upon ABA induction and less background fluorescence levels compared to the direct fusions, e.g. prRD29A::GFP and prRD29B::GFP lines.

Example 5. Compound Screen Using the Two Component System

Seeds from *Arabidopsis* lines transformed with prTARGET::GFP (direct fusion reporter system) or prTARGET::LexA:Gal4_oplexA::GFP (two component reporter system) described in Example 3 were used in a primary screen on a 30K diverse compound panel to identify compounds that can induce the prTARGET promoter using procedures described in Example 7. Compounds that showed at least 2.5 fold induction compared to DMSO were identified as "hits". Several compounds that did not meet the threshold of 2.5 fold induction with the direct fusion reporter line (Y axis) were identified as hits using the improved two-component system (X axis) in which they did meet the 2.5 fold induction threshold compared to controls, demonstrating the improved sensitivity of the two-component system (FIG. 7).

Twenty (20) compound hits, identified from the primary screen using the above-referenced prTARGET::LexA:Ga14_oplex::GFP reporter line, were applied to wild type *Arabidopsis* seedlings according to Examples 9-10 in a secondary screen. Desiccation tolerance assays were performed according to the methods described in Example 13 below. Four of these compounds, "C71125", "C66433", "C71126" and "C71124" (shown in FIGS. 8B, 8C, 8D, and 8E, respectively), were confirmed to have conferred significant tolerance to desiccation stress to *Arabidopsis* seedlings (shown in FIG. 8A) relative to the control, DMSO (FIG. 8).

Example 6. Identifying Compounds that Modulate Signaling Pathways Relevant to Biotic Stress Tolerance, Abiotic Stress Tolerance, or Nitrogen Usage Biotic stresses or abiotic stresses can induce changes in gene expression of signaling pathways that may potentiate a plant's natural defense against unfavorable conditions. A number of promoters have been selected from some of the marker genes involved in these pathways, i.e., genes that are up-regulated during the response of interest identified in the scientific literature or determined with in-house transcriptional profiling experiments. Promoters involved in signaling pathways of interest include but are not limited to desiccation or drought-inducible promoters including sequences located in the promoter regions of AT1G71520 (prTarget), At5g52310 (RD29A), At5g52300, AT1G16850, At3g46230, AT1G52690, At2g37870, AT5G43840, At5g66780, At3g17520, or At4g09600 (SEQ ID NOs: 48, 38, 30, 29, 31, 32, 33, 34, 35, 36, or 37, respectively), disease inducible promoters including a regulatory sequence located in the promoter region of AT1G15125 or AT5G44420 (SEQ ID NOs: 44 and 46, respectively), those that are inducible by a change of nitrogen status in the environment including sequences located in the promoter regions of AT1G13300, AT2G48080, AT3G25790, AT5G10210, AT5G19970, AT5G44420 (PDF1.2), or AT5G24770 (VSP2) (SEQ ID NOs: 39, 40, 41, 42, 43, 46, or 47, respectively), and those that are inducible by low phosphate availability in the environment, including the sequence located in the promoter region of At2g38940 (AtPT2; SEQ ID NO: 45).

The exemplary promoter sequences that can be used to identify compounds that can modulate and improve plant's yield, performance, drought response, disease response, or nitrogen usage include SEQ ID NO: 29-44.

Any one of the aforementioned promoter sequences or their functional parts can be constructed into a two-component transcriptional fusion reporter system prGENE::LEXA:GAL4_opLEXA::GFP to screen for compounds that can induce the activity of prGENE and have beneficial effects on plant stress tolerance (prGENE represents any of the aforementioned promoters). A primary screen using said reporter system is performed by the method described in Example 7. Compounds that produce a greater than a pre-defined threshold level of induction of prGENE are identified as "hits" and applied to *Arabidopsis* wild-type seedlings according to the procedures in Example 9 and 10. Phenotypic assays (used as secondary screens) are performed according to the methods in Example 13. The compounds that yield the desired phenotypes in plants, such as greater yield, greater performance, increased abiotic stress tolerance, increased desiccation tolerance, improved nitrogen use efficiency (NUE) and/or greater disease resistance, are then selected.

Example 7. Compound Screening

Sterile seeds were suspended in 0.5×MS, 0.5% sucrose, 0.05% MES and 0.1% Phytoblend agar at a density of 0.6 mg/mL and distributed to sterile 96-well polystyrene plates (250 µL/well). The plates were covered and sealed with breathable tape and incubated at 25° C. under 24-hour light (100 µE m-2 s-1) in a germination growth chamber. After four to seven days, the plates were removed and treated with the test compounds or DMSO (1 µL, in duplicate plates), covered, sealed, and returned to the growth chamber for one to three more days. The plates were then removed, uncovered and queued for analysis. Signal from green fluorescence protein (GFP, Ex 485 nm, Em 525 nm) was quantified on a microplate reader (TriStar Multimode, Berthold™, Oak Ridge, Tenn.; or EnSpire® Multimode, PerkinElmer®, Waltham, Mass.) in fluorescence area scan mode (3×3 grid, nine total scans/well). The average fluorescence for the nine scans was divided by the average fluorescence for all mock-treated wells (typically sixteen wells, 144 total scans) to obtain the per-plate activity ratio. The mean of the cross-plate duplicate activity ratios was then calculated. Additional statistical tests can be used to assess the significance of the response. A one-tailed heteroscedastic t-test was used between the treatment population (nine data points) and the control population (144 data points) and the Benjamin-Hochberg adjustment for multiple testing to generate a p(BH)-value was used. A high activity ratio and poor p(BH)-value (>0.05) may be a result of a spatially biased distribution of fluorescence within the test well. This can result, for example, from a seedling protruding towards the optical probe resulting in an erroneously high reading.

Additional meta-analysis can be used to determine the distribution of response values for each given GFP reporter line; see analysis and results in Example 13.

Example 8. Screening of a Chemical or Natural Product Library Using a Screening Assay in a High Throughput Format A transcriptional fusion reporter construct or a translation fusion reporter construct of the instant description is transformed into plants. 1 µl each of the chemicals, or natural products, from a library purchased from a commercial source (such as ChemBridge™ Inc., San Diego, Calif.; or Fondazione Ricerca per la Vita (FIIRV), Milan, Italy) was added to 96 well plates containing in each well 5-10 Arabidopsis seeds, which harbor a reporter construct encoding GFP, for instance of the type shown in FIGS. 1-4. The volume of the media in each well was 250 µl and the final concentration of the chemical in each well was targeted to be 5 to 30 µM. The seeds were allowed to germinate and grow in the medium. The data were normalized based on negative controls in the same plate that are not treated with the chemical for one week and the GFP signal is quantified in a 96 well fluorescent reader (TriStar Multimode, or EnSpire Multimode).

An alternative screening method involved the germination and growth of the Arabidopsis seedlings harboring the GFP construct in 96 well plates for four to seven days prior to the addition of the compound stock solutions. The seedlings are exposed to the compound solution for an additional one to three days and the GFP fluorescence signal was quantified in a 96 well plate reader (TriStar Multimode, or EnSpire Multimode).

Example 9. Seed Preparation

Prior to plating, seeds for all experiments are surface sterilized in the following manner: (1) 5 minute incubation with mixing in 70% ethanol; (2) 20 minute incubation with mixing in 30% bleach, 0.01% Triton® X-100; (3) five rinses with sterile water. Seeds are resuspended in 0.1% sterile agarose and stratified at 4° C. for 2-4 days.

Example 10. Transplant Compound Treatment

Sterile stratified wild-type seeds (100 per plate) are sown on square plates containing the following medium: 80% MS solution, 1% sucrose, 0.05% MES, and 0.65% Phytoblend agar. Plates are incubated at 22° C. under 24-hour light (100 µE m-2 s-1) in a germination growth chamber. On day 8, the seedlings are transferred to 6-well assay plates at a density of 10 seedlings per well. The assay plates contained growth medium spiked with a unique test compound or DMSO (carrier solvent, 0.4% v/v) per well. The compound-treated seedlings are incubated at 22° C. under 24-hour light (100nE m-2 s-1) in a germination growth chamber.

Example 11. Spray Compound Treatment Procedure

Sterile seeds (50 per plate) are sown on standard Petri dishes containing the following medium: 80% MS solution, 1% sucrose, 0.05% MES, and 0.65% Phytagar. Plates are incubated at 22° C. under 24-hour light (95 µE m-2 s-1) in a germination growth chamber. On day 8, the seedlings are transferred to square growth plates containing fresh medium (15-25 seedlings per plate) and arranged such that their primary roots are exposed and aligned in parallel along the surface of the plate. The plates are sealed with venting tape and returned to the growth chamber, oriented for vertical growth. Typically, on day 9, the plates are sprayed with a 0.01% Spreader Sticker surfactant solution containing the test compound or DMSO (carrier solvent, 0.4% v/v) using a Preval® aerosol sprayer (1.5 mL/plate). The plates are re-sealed and returned to the growth chamber (horizontal orientation). After an additional (assay-dependent) number of days in a growth chamber, the seedlings are then subjected to any of the plate-based abiotic or biotic stress resistance assays detailed below. Alternatively, the plants may be treated by spraying on soil either once or multiple times during growth using a formulated solution of the test compound (e.g. 0.01% Spreader Sticker); control plants are mock treated. The plants are then subjected to phenotypic validation analysis by means of morphological, developmental or abiotic/biotic stress resistance assays, such as in the example as described below.

Example 12. Genetic Marker Analysis

A compound identified in the screen analysis can also be evaluated for the effects on the genetic markers of a signaling pathway under physiological conditions where this signaling pathway is active. Such genetic marker assays are typically conducted after or concurrently with the primary screen measuring the activation or repression of the promoter-reporter construct, and can be performed using a variety of techniques known by those of skill in the art to be suitable. For example, mRNA expression can be detected using amplification-based methodologies, northern or dot blots, nuclease protection and the like. Polypeptide products can be identified using immunoassays. For example, to evaluate a compound for its effect on the genetic components (promoters or polypeptides) of the light signaling pathway, Arabidopsis seedlings are grown on solid media (50% MSIB5, 0.05% MES (PH 5.7), 0.5% sucrose, 0.8% agar) in a growth chamber at 22° C. with continuous light (95 IIMollm2/s) for nine days. The seedlings are then transplanted onto media containing various chemicals (typically at 20 µM) or DMSO controls and returned to identical growth conditions for 6 h or 24 h. At the indicated time, the seedlings are removed from the media and immediately frozen in liquid nitrogen. RNA is extracted and cDNA is prepared using standard procedures known in the art. RT-PCR analysis is performed using primers for the genes that are critical component of the light signaling pathway, such as, for example, SEQ ID NOs: 2 and 28 of PCT publication WO2009/117448, the entire content of which is incorporated herein by reference.

Genetic marker activation or inhibition can also be determined by using reporter constructs. Such reporter constructs can, e.g., comprise the promoter sequences from the genetic markers, or alternatively, can comprise promoters form genes that are responsive to the genetic markers. Activation or inhibition using reporter constructs can be analyzed using the same methodology as that employed for evaluating the promoter-reporter activation/inhibition.

Example 13. Phenotypic Validation Analysis

In these Examples, unless otherwise indicated, morphological and physiological traits are disclosed for plants that are treated by a test compound in comparison to those treated by a control compound or a carrier solvent under the identical environmental conditions. Thus, a plant treated with a test compound that is described as large and/or drought or desiccation tolerant is large and more tolerant to drought or desiccation with respect to a control plant, the latter including plants treated with a control compound or a carrier solvent, or no treatment. When a plant is said to have a better performance than controls, it generally is larger, has greater yield, and/or shows less stress symptoms than control plants. The better performing lines may, for example, have produced less anthocyanin, or are larger, greener, more turgid, or more vigorous when challenged with a particular stress, compared to controls as noted below. Better performance generally implies greater size or yield, or tolerance to a particular biotic or abiotic stress, less sensitivity to ABA, or better recovery from a stress (as in the case of a soil-based drought treatment) than controls.

Phenotypic analyses can be performed according to what is known in the art, or with the following methods.

Morphological Analysis

Morphological analysis is performed to determine whether changes in transcriptional regulatory polypeptide levels or compound treatment affect plant growth and development. *Arabidopsis* seeds are cold-treated (stratified) on plates for three days in the dark (in order to increase germination efficiency) prior to transfer to growth cabinets. Initially, plates are incubated at 22° C. under a light intensity of approximately 100 microEinsteins for seven days. Seedlings (treated or untreated as described in Example 10 or 11) are then transferred onto soil (Sunshine® potting mix) Following transfer to soil, trays of seedlings are covered with plastic lids for 2-3 days to maintain humidity while they become established. Plants are grown on soil under fluorescent light at an intensity of 70-95 microEinsteins at a temperature of 18-23° C. and are optionally subjected to chemical treatments (or mock treatments) as described in Example 10 or 11. Light conditions consist of a 24-hour photoperiod unless otherwise stated. In instances where alterations in flowering time are apparent, flowering time may be re-examined under 8-hour, 12-hour and 24-hour light to assess whether the phenotype is photoperiod dependent. Under typical 24-hour light growth conditions, the typical generation time (seed to seed) for *Arabidopsis* is approximately 14 weeks.

Because many aspects of *Arabidopsis* development are dependent on localized environmental conditions, in all cases plants are evaluated in comparison to controls (i.e. plants that are untreated or treated with a control compound or a solvent carrier and are otherwise identical to the plants treated with the test compounds) in the same flat. Careful examination is made at the following stages: seedling (1 week), rosette (2-3 weeks), flowering (4-7 weeks), and late seed set (8-12 weeks). Seed is also inspected. Plants having no or few seeds are considered partially or totally sterile. Seedling morphology is assessed on selection plates. At all other stages, plants are macroscopically evaluated while growing on soil or another suitable growth medium. All significant differences (including alterations in growth rate, size, leaf and flower morphology, coloration and flowering time) are recorded, but routine measurements are not be taken if no differences are apparent. In certain cases, stem sections are stained to reveal lignin distribution. In these instances, hand-sectioned stems are mounted in phloroglucinol saturated 2M HCl (which stains lignin pink) and viewed immediately under a dissection microscope.

Physiological Analysis

Ten lines are typically examined in subsequent plate based physiology assays. A similar number of compound-treated plants are compared to controls when testing the effects of compound treatments.

Yield and Performance Analysis

*Arabidopsis thaliana* (Col-0) seeds were suspended in 0.1% agarose and stratified for three to four day s at 4° C. Two to three seeds were surface sown on SunShine® Mix #2 amended with perlite (25%) in 2.5×2.5 inch pots. Plants were watered with either complete fertilizer (containing 3.75 mM N), or low N fertilizer (containing 0.1 mM N). Seedlings were thinned to one plant per pot eight to 10 days after germination. At 18 days after sowing, 282 µL of an exudate or media control was applied at base of plant. Ten days later, the above ground plant material was harvested, dried, and weighed to determine dry weight. To determine if any exudate caused a significant change in biomass, statistical analysis was performed using PASW® Statistics (version 18) software. Significance was determined using an ANOVA and Dunnet's t-test.

Nitrogen Use Efficiency (NUE) Assay

There are multiple ways in which a plant can change nitrogen partitioning in response to changes in nitrogen availability. For example, increased photosynthesis/seed dry weight or biomass. Routine measurements can be used to identify beneficial changes in nitrogen partitioning that result in plants with improved NUE.

One or multiple of the following parameters are assessed to determine the benefit to compound treated plants versus mock-treated control lines:

Photosynthesis: Light Saturated/Light Limited/Vcmax/Jmax/TPU limitation
Electron Transport: Light Saturated/Light limited
Respiration: Whole plant
Leaf chlorophyll content
Plant dry weight (root/shoot)
Plant carbon:nitrogen ratios (root/shoot)
Seed dry weight Compound treatments that cause plant samples to deviate from controls in any of these relationships may improve nitrogen usage.

Plate Assays

Different plate-based physiological assays (shown below), representing a variety of abiotic and water-deprivation-stress related conditions, are used as a pre-screen to identify top performing lines (i.e. lines treated with a particular compound), that are generally then tested in subsequent soil based assays. Typically, ten lines are subjected to plate assays, from which the best three lines are selected for subsequent soil based assays.

In addition, a nutrient limitation assay can be used to find compounds that allow more plant growth upon deprivation of nitrogen. Nitrogen is a major nutrient affecting plant growth and development that ultimately impacts yield and stress tolerance. These assays monitor primarily root but also rosette growth on nitrogen deficient media. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process may be regulated by light, as well as by C/N metabolic status of the plant. A C/N sensing assay is thus used to look for alterations in the mechanisms plants use to sense internal levels of carbon and nitrogen metabolites which could activate signal transduction cascades that regulate the transcription of N-assimilatory genes. To determine whether these mechanisms are altered or modified, we exploit the observation that control plants grown on media containing high levels of sucrose (3%) without a nitrogen source accumulate high levels of anthocyanins. This sucrose-induced anthocyanin accumulation can be relieved by the addition of either inorganic or organic nitrogen. Glutamine is used as a nitrogen source since it also serves as a compound used to transport N in plants.

Growth Assays

Unless otherwise stated, experiments are typically performed with the *Arabidopsis thaliana* ecotype Columbia (col-0), soybean or maize plants.

Growth assays may be conducted with *Arabidopsis* or other plant species (e.g., soy, maize, etc.) that are treated or untreated with test compounds or control as described in Examples 10 or 11. For example, *Arabidopsis* seedlings are grown on solid media (50% MS/B5, 0.05% MES (pH 5.7), 0.5% sucrose, 0.8% agar) in a growth chamber at 22° C. with continuous light (95 μMol/m2/s) for nine days. The seedlings are then transplanted onto media containing various chemicals (typically at 20 μM) or DMSO controls and returned to identical growth conditions for three additional days. Growth assays may assess tolerance to severe desiccation (a type of water deprivation assay), growth in cold conditions at 8° C., root development (visual assessment of lateral and primary roots, root hairs and overall growth), and phosphate limitation.

For the nitrogen limitation assay, plants are grown in 80% Murashige and Skoog (MS) medium in which the nitrogen source is reduced to 20 mg/L of $NH_4NO_3$. Note that 80% MS normally has 1.32 g/L $NH_4NO_3$ and 1.52 g/L $KNO_3$.

For phosphate limitation assays, seven day old seedlings are germinated on phosphate-free MS medium in which $KH_2PO_4$ is replaced by $K_2SO_4$.

For chilling growth assays, seeds are germinated and grown for seven days on MS+Vitamins+1% sucrose at 22° C. and are then transferred to chilling conditions at 8° C. and evaluated after another 10 days and 17 days.

For desiccation (plate-based water deprivation) assays, sterile, stratified wild-type seeds (100 per plate) were sown on square plates and on day 8 the seedlings were subjected to treatment by a unique test compound or a control compound according to Example 10 or 11. On day 11 the assay plates were photographed and placed in a laminar flow hood with the lid removed for 3 hours, rotating the plates 180 degrees after 90 minutes. The seedlings were then removed from the medium, placed on the surface of the inverted lid and desiccated an additional 3.6 hours. The seedlings were then transferred to square plates containing fresh growth medium, returned to the growth chamber and allowed to recover for 3-4 days prior to photo documentation and scoring.

For the polyethylene glycol (PEG) hyperosmotic stress tolerance screen, plant seeds are gas sterilized with chlorine gas for 2 h. The seeds are plated on each plate containing 3% PEG, ½×MS salts, 1% phytagel, and 10 μg/ml glufosinate-ammonium (BASTA). Two replicate plates per seed line are planted. The plates are placed at 4° C. for three days to stratify seeds. The plates are held vertically for 11 additional days at temperatures of 22° C. (day) and 20° C. (night). The photoperiod is 16 h. with an average light intensity of about 120 μmol/m2/s. The racks holding the plates are rotated daily within the shelves of the growth chamber carts. At 11 days, root length measurements are made. At 14 days, seedling status is determined, root length is measured, growth stage is recorded, the visual color is assessed, pooled seedling fresh weight is measured, and a whole plate photograph is taken.

Germination assays may also be carried out with NaCl (150 mM, to measure tolerance to salt), sucrose (9.4%, to measure altered or modified sugar sensing), cold (8° C.) or heat (32° C.). All germination assays are performed in aseptic conditions. Growing the plants under controlled temperature and humidity on sterile medium produces uniform plant material that has not been exposed to additional stresses (such as water stress) which could cause variability in the results obtained.

Prior to plating, seed for all experiments are surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds are re-suspended in 0.1% sterile agarose and stratified at 4° C. for 3-4 days. All germination assays follow modifications of the same basic protocol. Sterile seeds may be sown on conditional media that has a basal composition of 80% MS+Vitamins, or media containing test compounds as described in Example 6 above. Plates may be incubated at 22° C. under 24-hour light (120-130 μE m-2 s-1) in a growth chamber. Evaluation of germination and seedling vigor may be performed five days after planting.

Chlorophyll content, an indicator of photosynthetic capacity, may be measured with a SPAD meter.

Wilt Screen Assay

Soybean plants treated with test compounds or DMSO are grown in 5" pots in growth chambers. After the seedlings reach the V1 stage (the V1 stage occurs when the plants have one trifoliolate, and the unifoliolate and first trifoliolate leaves are unrolled), water is withheld and the drought treatment thus started. A drought injury phenotype score is recorded, in increasing severity of effect, as 1 to 4, with 1 designated no obvious effect and 4 indicating a dead plant. Drought scoring is initiated as soon as one plant in one growth chamber had a drought score of 1.5. Scoring continues every day until at least 90% of the wild type plants achieve scores of 3.5 or more. At the end of the experiment the scores for both test compound treated and control soybean seedlings are statistically analyzed using Risk Score and Survival analysis methods (Glantz (2001); Hosmer and Lemeshow (1999).

Water Use Efficiency (WUE) Assay

WUE is estimated by exploiting the observation that elements can exist in both stable and unstable (radioactive) forms. Most elements of biological interest (including C, H, O, N, and S) have two or more stable isotopes, with the lightest of these being present in much greater abundance than the others. For example, $^{12}C$ is more abundant than $^{13}C$ in nature ($^{12}C=98.89\%$, $^{13}C=1.11\%$, $^{14}C=<10\text{-}10\%$). Because $^{13}C$ is slightly larger than $^{12}C$, fractionation of $CO_2$ during photosynthesis occurs at two steps:

1. $^{12}CO_2$ diffuses through air and into the leaf more easily;
2. $^{12}CO_2$ is preferred by the enzyme in the first step of photosynthesis, ribulose bisphosphate carboxylase/oxygenase.

WUE has been shown to be negatively correlated with carbon isotope discrimination during photosynthesis in several C3 crop species. Carbon isotope discrimination has also been linked to drought tolerance and yield stability in drought-prone environments and has been successfully used to identify genotypes with better drought tolerance. $^{13}C/^{12}C$ content is measured after combustion of plant material and conversion to $CO_2$, and analysis by mass spectroscopy. With comparison to a known standard, $^{13}C$ content is altered in such a way as to suggest that treatment with test compounds improves water use efficiency.

Another potential indicator of WUE is stomatal conductance, that is, the extent to which stomata are open.

Data Interpretation

At the time of evaluation, plants are typically given one of the following qualitative scores:
- (++) Substantially enhanced performance compared to controls. The phenotype is very consistent and growth is significantly above the normal levels of variability observed for that assay.
- (+) Enhanced performance compared to controls. The response is consistent but is only moderately above the normal levels of variability observed for that assay.
- (wt) No detectable difference from wild-type controls.
- (−) Impaired performance compared to controls. The response is consistent but is only moderately above the normal levels of variability observed for that assay.
- (−−) Substantially impaired performance compared to controls. The phenotype is consistent and growth is significantly above the normal levels of variability observed for that assay.
- (n/d) Experiment failed, data not obtained, or assay not performed.

Soil Drought (Clay Pot)

The soil drought assay (typically performed on *Arabidopsis* in clay pots) is based on that described by Haake et al. (2002).

Sterile seeds (50 per plate) are sown on standard Petri dishes containing the following medium: 80% MS solution, 1% sucrose, 0.05% MES, and 0.65% Phytagar. Plates are incubated at 22° C. under 24-hour light (95 µE m-2 s-1) in a germination growth chamber. After seven days of growth the seedlings are transplanted to 3.5 inch diameter clay pots containing 80 g of a 50:50 mix of vermiculite:perlite topped with 80 g of ProMix. Typically, each pot contains 14 evenly spaced seedlings. The pots are maintained in a growth room under 24-hour light conditions (18-23° C., and 90-100 µE m-2 s-1) and watered for a period of 14 days. Compounds (or DMSO) are applied as a 0.01% Spreader Sticker solution (or similar formulation) using a Preval aerosol sprayer (ca. 2 mL/pot or 100 g/ha) no more than three times during days 7-13 post-transplant. Water is then withheld and pots are placed on absorbent diaper paper for a period of 8-10 days to apply a drought treatment. At the end of the drought period, pots are re-watered and then scored after 5-6 additional days. The number of surviving plants in each pot is counted, and the survival percentage calculated.

In a given experiment, six or more pots of plants treated by test compounds with six or more pots of the appropriate control are typically compared. The mean drought score and mean proportion of plants surviving (survival rate) are calculated for both the transgenic line and the wild-type pots. In each case a p-value* is calculated, which indicates the significance of the difference between the two mean values.

For the assays where control and experimental plants are in separate pots, survival is analyzed with a logistic regression to account for the fact that the random variable is a proportion between 0 and 1. The reported p-value is the significance of the experimental proportion contrasted to the control, based upon regressing the logit-transformed data.

Drought score, being an ordered factor with no real numeric meaning, is analyzed with a non-parametric test between the experimental and control groups. The p-value is calculated with a Mann-Whitney rank-sum test.

Disease Resistance

Resistance to pathogens, such as *Sclerotinia sclerotiorum* and *Botrytis cinerea*, can be assessed in plate-based assays. Unless otherwise stated, all experiments are performed with the *Arabidopsis thaliana* ecotype Columbia (Col-0). Control plants for assays on lines containing direct promoter-fusion constructs are wild-type plants or Col-0 plants transformed an empty transformation vector (pMEN65).

Prior to plating, seed for all experiments are surface sterilized in the following manner: (1) 5 minute incubation with mixing in 70% ethanol; (2) 20 minute incubation with mixing in 30% bleach, 0.01% Triton X-100™; (3) five rinses with sterile water. Seeds are resuspended in 0.1% sterile agarose and stratified at 4° C. for 2-4 days.

Sterile seeds are sown on starter plates (15 mm deep) containing 50% MS solution, 1% sucrose, 0.05% MES, and 1% Bacto™-Agar. 40 to 50 seeds are sown on each plate. Seedlings are grown on solid media (50% MS/B5, 0.05% MES (pH 5.7), 0.5% sucrose, 0.8% agar) in a growth chamber at 22° C. with continuous light (95 µMol/m2/s) for nine days. The seedlings are then transplanted onto media containing various chemicals (typically at 20 µM) or DMSO controls and returned to identical growth conditions for three additional days. Seedlings are then transferred to assay plates (25 mm deep plates with medium minus sucrose). On day 14, seedlings are inoculated (specific method below). After inoculation, plates are put in a growth chamber under a 12-hour light/12-hour dark schedule. Light intensity is lowered to 70-80 µE m-2 s-1 for the disease assay.

*Sclerotinia* inoculum preparation. A *Sclerotinia* liquid culture is started three days prior to plant inoculation by cutting a small agar plug (¼ sq. inch) from a 14- to 21-day old *Sclerotinia* plate (on Potato Dextrose Agar; PDA) and placing it into 100 ml of half-strength Potato Dextrose Broth. The culture is allowed to grown in the Potato Dextrose Broth at room temperature under 24-hour light for three days. On the day of seedling inoculation, the hyphal ball is retrieved from the medium, weighed, and ground in a blender with water (50 ml/gm tissue). After grinding, the mycelial suspension is filtered through two layers of cheesecloth and the resulting suspension is diluted 1:5 in water. Plants are inoculated by spraying to run-off with the mycelial suspension using a Preval aerosol sprayer.

*Botrytis* inoculum preparation. *Botrytis* inoculum is prepared on the day of inoculation. Spores from a 14- to 21-day old plate (on PDA) are resuspended in a solution of 0.05% glucose, 0.03M $KH_2PO_4$ to a final concentration of $10^4$ spores/ml. Seedlings are inoculated with a Preval aerosol sprayer, as with *Sclerotinia* inoculation.

Resistance to *Erysiphe cichoracearum* is assessed in a soil-based assay. *Erysiphe cichoracearum* is propagated on a pad4 mutant line in the Col-0 background, which is highly susceptible to *Erysiphe* (Reuber et al. (1998), or on squash plants, since this particular species of *Erysiphe* also parasitizes squash. Inocula are maintained by using a small paintbrush to dust conidia from a 2-3 week old culture onto 4-week old plants. For the assay, seedlings are grown on plates for one week under 24-hour light in a germination chamber, then transplanted to soil and grown in a walk-in growth chamber under a 12-hour light/12-hour dark light regimen, 70% humidity. Each line is transplanted to two 13 cm square pots, nine plants per pot. In addition, three control plants are transplanted to each pot, for direct comparison with the test line. Approximately 3.5 weeks after transplanting, plants are inoculated using settling towers, as described by Reuber et al., 1998. Generally, three to four heavily infested leaves are used per pot for the disease assay. Level of fungal growth is evaluated eight to ten days after inoculation.

Screening Method for Compounds that Increase Plant Performance or Yield with Different Promoters Low nutrient availability-inducible and disease-inducible promoters. After screening a collection of compounds or natural products (n>2,000), randomly selected prior to determining biological activity (unbiased), the Tukey method for outlier detection was used, in some cases, to establish the minimum ratio threshold (i.e. Tukey fence) that was considered a compound hit (i.e. statistical outlier) for each GFP reporter line as shown in Table 1.

treatment when compared to a mock treatment (negligible activity). The qualitative visual assay (staining) was followed by a quantitative 4-methylumbelliferyl-beta-D-glucuronide (MUG) expression assay (FIG. 12) in which multiple independent homozygous seedlings from representative T3 lines V, W, X, Y and Z (where Z=line Z458603-1) were evaluated for GUS activity using the MUG turnover assay. Induced GUS activity, shown as level of 4-MU (nmols/min/mg protein) produced, is compared to a known positive control genotype J containing a different DBD-AD fusion, J12121 (35S::LexA:GAL4:GR_opLexA:: GUS). The mock treatment values were below levels that would appear in this graph.

It is expected that the same methods may be applied to identify other useful and valuable promoter sequences, and the sequences may be derived from a diverse range of species.

TABLE 1

Identification of compounds or natural products involved in diverse biological processes

| Promoter Name | Locus Code | Strain Code | Seed ID | Growth Regime Code | Average Activity Ratio | Tukey Fence |
|---|---|---|---|---|---|---|
| prAtPT2 | AT2G38940 | MB-282 | S516424 | D259385 | 6.6 | 4.0 |
|  | AT2G38940 | " | S516424 | D238206 | 4.1 | 4.0 |
| prPDF1.2 | AT5G44420 | " | S421544 | D238206 | 6.9 | 5.2 |
|  | AT5G44420 | " | S516664 | D259385 | 7.6 | 7.3 |
| prAtPT2 | AT2G38940 | MB-424 | S516424 | D259385 | 9.2 | 4.0 |
|  | AT2G38940 | " | S516424 | D238206 | 4.8 | 4.0 |
| prPDF1.2 | AT5G44420 | " | S421544 | D259385 | 6.8 | 5.2 |
|  | AT5G44420 | " | S421544 | D238206 | 9.0 | 5.2 |
| prAtPT2 | AT2G38940 | MB-464 | S516424 | D259385 | 6.8 | 4.0 |
|  | AT2G38940 | " | S516424 | D238206 | 4.6 | 4.0 |
| prPDF1.2 | AT5G44420 | " | S421544 | D238206 | 8.5 | 5.2 |

Notes for Table 1:
The promoters in column 1 include low-phosphate inducible (prAtPT2) and disease-inducible (prPDF1.2) promoter types.
Locus Codes in column 2 are unique public identifiers for the genetic locus from which the promoters were derived.
The Strain Codes in column 3 represent internal identifiers for unique microbial strain exudates.
The Seed IDs in column 4 represent internal identifiers for specific seed stocks for a given GFP reporter, which are important to track because the possibility that epigenetic differences could affect the sensitivity or specificity of the promoter in the GFP reporter transgene (e.g. prAtPT2 or prPDF1.2).
Growth Regime Codes in column 5 represent internal identifiers corresponding to a specific set of parameters (such as media, temperature, etc.) used to cultivate the microbial strain during the production of an exudate, extract or other microbially-derived natural product.

Desiccation inducible promoters. As shown in Example 5 of the specification, Seeds from *Arabidopsis* lines transformed with a prTARGET (promoter fragment from prAT1G71520, SEQ ID NO: 48)-GFP direct fusion reporter system, or prTARGET::LexA:Ga14_oplexA::GFP (two component reporter system), or a prTARGET::LexA: Ga14_oplexA::LUC:GFP translational reporter gene fusion were used in a primary screen of 30,000 diverse compounds to identify and select compounds that surprisingly can induce the prTARGET promoter. Desiccation tolerance assays were performed with such selected compounds, and four of these compounds were confirmed to have conferred significant tolerance to desiccation stress to *Arabidopsis* seedlings relative to the control DMSO treatment.

Data were collected with different DNA binding domains (DBDs) and activation domains (ADs), including a dexamethasone-inducible "driver" system using the DBD of GAL4 fused to the AD of VP16 as a "transcriptional activator" and beta-glucuronidase (GUS) as a reporter.

In the experiment shown in FIG. 12, homozygous plant lines of the genotype: 35S::GAL4(DBD):VP16(AD):GR_6 xUAS::GUS were developed that showed a clear and strong induction of GUS expression in response to dexamethasone Embodiments of the Instant Description Embodiment 1

One or more reporter gene constructs comprising (a) a target promoter sequence that is capable of being recognized by a transcription factor, (b) a polynucleotide sequence that encodes a DNA sequence-specific transactivator, and (c) a reporter polynucleotide, wherein the target promoter sequence and the DNA sequence-specific transactivator cooperatively regulate expression of the reporter polynucleotide.

Embodiment 2

The one or more reporter gene constructs of Embodiment 1, wherein the sequence specific transactivator is capable of binding a regulatory region of the reporter polynucleotide.

Embodiment 3

The one or more reporter gene constructs of Embodiment 1, wherein the sequence specific transactivator is capable of binding a regulatory region of a polynucleotide that encodes the transcription factor.

Embodiment 4

The one or more reporter gene constructs of Embodiment 1, wherein the transcription factor is capable of binding a regulatory region of the reporter polynucleotide.

Embodiment 5

The one or more reporter gene constructs of Embodiment 1, wherein the DNA sequence-specific transactivator is DBD:AD;
wherein AD comprised at least one sequence selected from the group consisting of SEQ ID NOs: 20, and 22-26; and
wherein DBD comprised at least one sequence selected form the group consisting of SEQ ID NOs: 16 and 18.

Embodiment 6

The one or more reporter gene constructs of Embodiment 1, wherein the DNA sequence-specific transactivator is a steroid-inducible transactivator, which regulates transcription of the transcription factor when bound by a steroid.

Embodiment 7

The one or more reporter gene constructs of Embodiment 6, wherein the steroid-inducible transactivator is DBD:AD:GR;
wherein AD comprises at least one sequence selected from the group consisting of SEQ ID NOs: 20, and 22-26;
wherein DBD comprises at least one sequence selected from the group consisting of SEQ ID NOs: 16 and 18;
wherein GR comprises SEQ ID NO: 14; and
wherein the steroid is dexamethasone.

Embodiment 8

The one or more reporter gene constructs of Embodiment 6, wherein the one or more reporter gene constructs further comprise a polynucleotide sequence that encodes an additional DNA sequence-specific transactivator,
wherein the additional DNA sequence-specific transactivator regulates transcription of the reporter gene through binding of its cognate sequence that is operably linked to the reporter polynucleotide.

Embodiment 9

The one or more reporter gene constructs of Embodiment 8, wherein the transcription factor is capable of binding a regulatory region of a polynucleotide encoding the additional DNA sequence-specific transactivator.

Embodiment 10

The one or more reporter gene constructs of Embodiment 8, wherein the steroid-inducible transactivator is DBD:AD:GR;
wherein AD is selected from the group consisting of SEQ ID NOs: 20, and 22-26;
wherein DBD is selected form the group consisting of SEQ ID NOs: 16 and 18;
wherein GR comprises SEQ ID NO: 14; and
wherein the steroid is dexamethasone.

Embodiment 11

One or more reporter gene constructs comprising a polynucleotide encoding a DNA sequence-specific transactivator and a polynucleotide encoding a translational fusion of a reporter gene molecule and a polypeptide of interest,
wherein the DNA sequence-specific transactivator regulates expression of the translational fusion.

Embodiment 12

The one or more reporter gene constructs of Embodiment 11, wherein the DNA sequence-specific transactivator is DBD:AD:GR;
wherein AD is selected from the group consisting of SEQ ID NOs: 20, and 22-26;
wherein DBD is selected form the group consisting of SEQ ID NOs: 16 and 18; and
wherein GR comprises SEQ ID NO: 14.

Embodiment 13

A transgenic cell comprising (a) a target promoter sequence that is capable of being recognized by a transcription factor, (b) a polynucleotide sequence that encodes a DNA sequence-specific transactivator, and (c) a reporter polynucleotide,
wherein the target promoter and the DNA sequence-specific transactivator cooperatively regulates expression of the reporter gene.

Embodiment 14

The transgenic cell of Embodiment 13, wherein the sequence specific transactivator is capable of binding a regulatory region of the reporter polynucleotide.

Embodiment 15

The transgenic cell of Embodiment 13, wherein the sequence specific transactivator is capable of binding a regulatory region of a polynucleotide that encodes the transcription factor.

Embodiment 16

The transgenic cell of Embodiment 13, wherein the transcription factor is capable of binding a regulatory region of the reporter polynucleotide.

Embodiment 17

The transgenic cell of Embodiment 13, wherein the DNA sequence-specific transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18; and
wherein GR comprises SEQ ID NO: 14.

Embodiment 18

The transgenic cell of Embodiment 13, wherein the DNA sequence-specific transactivator is a steroid-inducible transactivator, which regulates transcription of the transcription factor when bound by a steroid.

Embodiment 19

The transgenic cell of Embodiment 18, wherein the steroid-inducible transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18;
wherein GR comprises SEQ ID NO: 14; and
wherein the steroid is dexamethasone.

Embodiment 20

The transgenic cell of Embodiment 18, further comprises a polynucleotide sequence that encodes an additional DNA sequence-specific transactivator and is located at 3' relative to the steroid-inducible transactivator and 5' relative to the reporter gene,
wherein the additional DNA-sequence-specific transactivator regulates transcription of the reporter gene through binding of its cognate sequence that is operably linked to the reporter polynucleotide.

Embodiment 21

The transgenic cell of Embodiment 19, wherein the transcription factor is capable of binding a regulatory region of a polynucleotide encoding the additional DNA sequence-specific transactivator.

Embodiment 22

The transgenic cell of Embodiment 19, wherein the steroid-inducible transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18;
wherein GR comprises SEQ ID NO: 14; and
wherein the steroid is dexamethasone.

Embodiment 23

A transgenic cell comprising a polynucleotide encoding a DNA sequence-specific transactivator and a polynucleotide encoding a translational fusion of a reporter gene molecule and a polypeptide of interest,
wherein the DNA sequence-specific transactivator regulates expression of the translational fusion.

Embodiment 24

The transgenic cell of Embodiment 23, wherein the DNA sequence-specific transactivator is DBD:AD:GR;
wherein AD comprises at least one sequence selected from the group consisting of SEQ ID NOs: 20, and 22-26;
wherein DBD comprises at least one sequence selected from the group consisting of SEQ ID NOs: 16 and 18; and
wherein GR comprises SEQ ID NO: 14.

Embodiment 25

The transgenic cell of Embodiment 13, wherein the transgenic cell is a cell derived from plants, mammals, microbes, *Drosophila, Caenorhabditis*, or yeast.

Embodiment 26

A method of screening for useful compounds comprising the steps of:
(a) contacting at least one test compound with a transgenic cell comprising a target promoter sequence that is capable of being recognized by a transcription factor, a polynucleotide sequence that encodes a DNA sequence-specific transactivator, and a reporter polynucleotide,
    wherein the target promoter and the DNA sequence-specific transactivator cooperatively regulate expression of the reporter gene; and
(b) selecting a compound that alters the reporter gene activity relative to controls.

Embodiment 27

The method of Embodiment 26, wherein the sequence specific transactivator is capable of binding a regulatory region of the reporter polynucleotide.

Embodiment 28

The method of Embodiment 26, wherein the sequence specific transactivator is capable of binding a regulatory region of a polynucleotide that encodes the transcription factor.

Embodiment 29

The method of Embodiment 26, wherein the transcription factor is capable of binding a regulatory region of the reporter polynucleotide.

Embodiment 30

The method of Embodiment 26, wherein the DNA sequence-specific transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18; and
wherein GR comprises SEQ ID NO: 14.

Embodiment 31

The method of Embodiment 26, wherein the DNA sequence-specific transactivator is a steroid-inducible transactivator, which regulates transcription of the transcription factor when bound by a steroid.

Embodiment 32

The method of Embodiment 31, wherein the steroid-inducible transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18;
wherein GR comprises SEQ ID NO: 14; and
wherein the steroid is dexamethasone.

Embodiment 33

The method of Embodiment 31, wherein the transgenic cell further comprises a polynucleotide sequence that encodes an additional DNA sequence-specific transactivator,
wherein the additional DNA-sequence-specific transactivator regulates transcription of the reporter gene through binding of its cognate sequence that is operably linked to the reporter polynucleotide.

Embodiment 34

The method of Embodiment 33, wherein the transcription factor is capable of binding a regulatory region of a polynucleotide encoding the additional DNA sequence-specific transactivator.

Embodiment 35

The method of Embodiment 33, wherein the dexamethasone steroid-inducible transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18;
wherein GR comprises SEQ ID NO: 14; and
wherein the steroid is dexamethasone.

Embodiment 36

A method of screening for useful compounds comprising the steps of:
(a) contacting at least one test compound with a transgenic cell comprising a polynucleotide encoding a DNA sequence-specific transactivator and a polynucleotide encoding a translational fusion of a reporter gene molecule and a polypeptide of interest,
    wherein the DNA sequence-specific transactivator regulates expression of the translational fusion; and
(b) selecting a compound that alters the reporter gene activity relative to controls.

Embodiment 37

The method of Embodiment 36, wherein the DNA sequence-specific transactivator is DBD:AD:GR;
wherein AD comprises at least one sequence selected from the group consisting of SEQ ID NOs: 20, and 22-26;
wherein DBD comprises at least one sequence selected form the group consisting of SEQ ID NOs: 16 and 18; and
wherein GR comprises SEQ ID NO: 14.

Embodiment 38

The method of Embodiment 26 further comprising the step of:
(c) contacting a plant with the selected compound and detecting a modified trait in the plant relative to controls.

Embodiment 39

The method of Embodiment 36 further comprising the step of:
(c) contacting a plant with the selected compound and detecting a modified trait in the plant relative to controls.

REFERENCES

Aoyama et al. (1995) *Plant Cell* 7:1773-1785
Altschul et al. (1990) *J. Mol. Biol.* 215:403-410
Altschul et al. (1994) *Nature Genetics* 6: 119-129
Bohmert et al. (1998) *EMBO J.* 17:170-80
Bruce et al. (2000) *Plant Cell* 12: 65-79
Borevitz et al. (2000) *Plant Cell* 12: 2383-2393
Bowman et al. (1999) *Development* 126:2387-96
Bustin and Reeves (1996) *Prog. Nucl. Acids Res. Mol. Biol.* 54:35-100
Chao et al. (1997) *Cell* 89:1133-44
da Costa e Silva et al. (1993) *Plant J.* 4:125-135
Dehesh et al. (1990) *Science* 250:1397-1399
Di Laurenzio et al. (1996) *Cell* 86:423-433
Duboule (1994) *Guidebook to the Homeobox Genes*, Oxford University Press
Foster et al. (1994) *FASEB J.* 8:192-200
Forsburg and Guarente (1989) *Genes Dev.* 3:1166-1178)
Fraley et al. (1983) *Proc. Natl. Acad. Sci. USA* 80:4803
Gilmour et al. (1998) *Plant J.* 16: 433-442
Giraudat et al. (1992) *Plant Cell* 4:1251-1261
Giniger E; Ptashne M (1987) *Nature* 330(6149):670-2
Gill and Ptashne (1987) *Cell* 51:121-126, Estruch et al (1994) *Nucl. Acids Res.* 22:3983-3989
Haake et al. (2002) *Plant Physiol.* 130: 639-648
Hall et al. (1998) *Plant Cell* 10:925-936
Horsch et al. (1984) *Science* 233:496-498.
Ishiguro and Nakamura (1994) *Mol. Gen. Genet.* 244:563-571
Kennison (1995) *Annu. Rev. Genet.* 29:289-303
Kim et al. (1997) *Plant J.* 11:1237-1251
Klein et al. (1996) *Mol. Gen. Genet.* 1996 250:7-16
Klug and Schwabe (1995) *FASEB J.* 9: 597-604
Klein et al. (1987) *Nature* 327: 70-73
Littlewood et al. (1994) *Prot. Profile* 1:639-709
Lu and Ferl (1995) *Plant Physiol.* 109:723
Luo et al. (1996) *Nature* 383:794-799
Ma J; Ptashne M. Cell 1987; 50(1):137-42
Martin and Paz-Ares, (1997) *Trends Genet.* 13:67-73
Moore et al. (1998) *Proc. Natl. Acad. Sci. USA* 95: 376-381
Paszkowski et al. (1984) *Embo J.* 3:2717-2722
Reeves and Nissen (1990) *Journal of Biological Chemistry* 265:8573-8582
Reuber et al. (1998) *Plant J.* 16: 473-485
Rieger et al. (1976) *Glossary of Genetics and Cytogenetics: Classical and Molecular*, 4th ed., Springer, Verlag, Berlin
Riechmann and Meyerowitz (1998) *J. Biol. Chem.* 379:633-646
Riechmann and Meyerowitz (1997) *J. Biol. Chem.* 378: 1079-1101

Rouse et al. (1998) *Science* 279:1371-1373
Souer et al. (1996) *Cell* 85:159-170
Tucker et al. (1994) *EMBO J.* 13:2994-3002
Wu et al. (1997) *Plant Physiol.* 114:1421-1431
Zhang et al. (1992) *Plant Cell* 4:1575-1588
Zhou et al. (1995) *Nucleic Acids Res.* 23:1165-1169

All publications and patent applications mentioned in this specification are herein incorporated by reference to the same extent as if each individual publication or patent application was specifically and individually indicated to be incorporated by reference.

The present description is not limited by the specific embodiments described herein. The instant description now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A method of screening for a hit compound that increases a plant performance-related or yield-related trait in a plant, said method comprising the steps of:
   (a) contacting at least one test compound with a transgenic plant cell comprising: (i) a target inducible promoter sequence that is operably linked to a polynucleotide sequence that encodes a DNA sequence-specific transactivator; and (ii) a reporter polynucleotide that is operably linked to a promoter sequence that can be recognized by the DNA sequence-specific transactivator;
   wherein the target inducible promoter sequence can be recognized by a transcriptional regulatory polypeptide that modulates a signaling pathway and said modulation results in increased plant performance or increased yield in a plant;
   (b) identifying a test compound that alters the reporter gene activity relative to controls and selecting a hit compound so identified; and
   (c) in a secondary screen, said hit compound is applied to the plant and said hit compound increases the plant performance or yield of the plant.

2. The method of claim 1, wherein the DNA sequence-specific transactivator is a translational fusion of a DNA binding domain (DBD) and a transcriptional activation domain (AD);
   wherein the AD comprises SEQ ID NO: 20; and
   wherein the DBD comprises SEQ ID NO: 16.

3. The method of claim 1, wherein the reporter polynucleotide encodes green fluorescent protein.

4. The method of claim 1, wherein the target inducible promoter sequence is a desiccation- or drought-inducible promoter located in the promoter region of AT1G71520, At5g52310, At5g52300, AT1G16850, At3g46230, AT1G52690, At2g37870, AT5G43840, At5g66780, At3g17520, or At4g09600 (SEQ ID NO: 48, 38, 30, 29, 31, 32, 33, 34, 35, 36, or 37, respectively), or a functional part thereof having a promoter function.

5. The method of claim 1, wherein the transgenic cell further comprises a polynucleotide sequence that encodes an additional DNA sequence-specific transactivator,
   wherein transcription of the polynucleotide sequence encoding the additional DNA sequence-specific transactivator is under the control of a promoter sequence that is recognized by the first DNA sequence-specific transactivator; and wherein the additional DNA sequence-specific transactivator regulates transcription of the reporter gene through binding of its cognate sequence that is operably linked to the reporter polynucleotide.

6. The method of claim 1, further comprising the step of:
   (d) contacting a plant with the hit compound and detecting the increased performance or yield in the plant relative to controls.

7. The method of claim 1, wherein the at least one test compound is obtained from a combinatorial chemical library, a natural product library, an exudate of a microbial culture, an extract of a microbial culture, or a microbially-derived natural product.

8. A method for increasing a performance-related or yield-related trait of a plant, said method comprising the steps of:
   (a) contacting at least one test compound with a transgenic plant cell comprising: (i) a target inducible promoter sequence that is operably linked to a polynucleotide sequence that encodes a DNA sequence-specific transactivator; and (ii) a reporter polynucleotide that is operably linked to a promoter sequence that can be recognized by the DNA sequence-specific transactivator;
   wherein the target inducible promoter sequence can be recognized by a transcriptional regulatory polypeptide that modulates specific signaling pathways and said modulation results in increased plant performance or yield in the plant;
   (b) identifying a test compound that produces a level of induction of the reporter polynucleotide greater than the level of induction in a control plant and selecting a hit compound so identified; and
   (c) in a secondary screen, contacting the plant with the hit compound and detecting increased performance or yield in the plant relative to a control plant.

9. The method of claim 8, wherein the level of induction of the reporter polynucleotide is at least 2.5 fold.

10. The method of claim 8, wherein the DNA sequence-specific transactivator is a translational fusion of a DBD comprising a sequence encoded by SEQ ID NO: 1 and an AD comprising SEQ ID NO: 20.

11. The method of claim 8, wherein the reporter polynucleotide encodes green fluorescent protein.

12. The method of claim 8, wherein the target inducible promoter sequence is a desiccation- or drought-inducible promoter located in the promoter region of AT1G71520, At5g52310, At5g52300, AT1G16850, At3g46230, AT1G52690, At2g37870, AT5G43840, At5g66780, At3g17520, or At4g09600 (SEQ ID NO: 48, 38, 30, 29, 31, 32, 33, 34, 35, 36, or 37, respectively), or a functional part thereof having a promoter function.

13. The method of claim 8, wherein the at least one test compound is obtained from a combinatorial chemical library, a natural product library, an exudate of a microbial culture, an extract of a microbial culture, or a microbially-derived natural product.

14. A method of screening for a hit compound that increases a plant performance-related or yield-related trait in a plant, said method comprising the steps of:
   (a) contacting at least one test compound with a transgenic plant cell comprising: (i) a target inducible promoter sequence that is operably linked to a polynucleotide sequence that encodes a DNA sequence-specific transactivator; and (ii) a reporter polynucleotide that is operably linked to a promoter sequence that can be recognized by the DNA sequence-specific transactivator;

wherein said at least one test compound is obtained from an exudate of a microbial culture, an extract of a microbial culture, or a microbially-derived natural product;

wherein the target inducible promoter sequence can be recognized by a transcriptional regulatory polypeptide that modulates a signaling pathway and said modulation results in increased plant performance or increased yield in a plant;

(b) identifying a test compound that alters the reporter gene activity relative to controls and selecting a hit compound so identified; and (c) in a secondary screen, said hit compound is applied to the plant and said hit compound increases the plant performance or yield of the plant.

15. The method of claim 1, wherein the target inducible promoter sequence is a disease-inducible promoter located in the promoter region of AT1G15125 or AT5G44420 (SEQ ID NO: 44 or 46, respectively), or a functional part thereof having a promoter function.

16. The method of claim 1, wherein the target inducible promoter sequence is a promoter inducible by a change of nitrogen status located in the promoter region of AT1G13300, AT2G48080, AT3G25790, AT5G10210, AT5G19970, AT5G44420, or AT5G24770 (SEQ ID NO: 39, 40, 41, 42, 43, 46, or 47, respectively), or a functional part thereof having a promoter function.

17. The method of claim 1, wherein the target inducible promoter sequence is a promoter inducible by low phosphate availability located in the promoter region of At2g38940 (SEQ ID NO: 45), or a functional part thereof having a promoter function.

18. The method of claim 8, wherein the target inducible promoter sequence is a disease-inducible promoter located in the promoter region of AT1G15125 or AT5G44420 (SEQ ID NO: 44 or 46, respectively), or a functional part thereof having a promoter function.

19. The method of claim 8, wherein the target inducible promoter sequence is a promoter inducible by a change of nitrogen status located in the promoter region of AT1G13300, AT2G48080, AT3G25790, AT5G10210, AT5G19970, AT5G44420, or AT5G24770 (SEQ ID NO: 39, 40, 41, 42, 43, 46, or 47, respectively), or a functional part thereof having a promoter function.

20. The method of claim 8, wherein the target inducible promoter sequence is a promoter inducible by low phosphate availability located in the promoter region of At2g38940 (SEQ ID NO: 45), or a functional part thereof having a promoter function.

* * * * *

UNITED STATES PATENT AND TRADEMARK OFFICE
CERTIFICATE OF CORRECTION

PATENT NO. : 10,677,785 B2
APPLICATION NO. : 15/097339
DATED : June 9, 2020
INVENTOR(S) : Armstrong et al.

Page 1 of 1

It is certified that error appears in the above-identified patent and that said Letters Patent is hereby corrected as shown below:

In the Specification

Column 4, Line 50: Please correct "(reported)" to read -- (reporter1) --

Column 21, Line 48: Please correct "("reported")" to read -- ("reporter1") --

Column 26, Line 1: Please correct "100nE" to read -- 100µE --

Signed and Sealed this
Twenty-seventh Day of October, 2020

Andrei Iancu
*Director of the United States Patent and Trademark Office*